(12) United States Patent
Strober et al.

(10) Patent No.: US 11,648,301 B2
(45) Date of Patent: *May 16, 2023

(54) TUMOR VACCINATION IN COMBINATION WITH HEMATOPOIETIC CELL TRANSPLANTATION FOR CANCER THERAPY

(71) Applicant: The Board of Trustees of the Leland Stanford Junior University, Stanford, CA (US)

(72) Inventors: Samuel Strober, Stanford, CA (US); Alexander Filatenkov, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 992 days.

This patent is subject to a terminal disclaimer.

(21) Appl. No.: 16/360,678

(22) Filed: Mar. 21, 2019

(65) Prior Publication Data

US 2019/0201514 A1 Jul. 4, 2019

Related U.S. Application Data

(63) Continuation of application No. 14/921,862, filed on Nov. 9, 2015, now Pat. No. 10,286,049, which is a continuation of application No. 13/935,251, filed on Jul. 3, 2013, now Pat. No. 9,192,627, which is a continuation of application No. 12/592,752, filed on Dec. 1, 2009, now Pat. No. 8,506,954.

(51) Int. Cl.
| | |
|---|---|
| *A61K 39/00* | (2006.01) |
| *A61K 41/00* | (2020.01) |
| *A61K 35/17* | (2015.01) |
| *A61K 35/14* | (2015.01) |

(52) U.S. Cl.
CPC .......... *A61K 39/0011* (2013.01); *A61K 35/14* (2013.01); *A61K 35/17* (2013.01); *A61K 41/00* (2013.01); *A61K 2039/5152* (2013.01); *A61K 2039/55522* (2013.01); *A61K 2039/55561* (2013.01); *A61K 2039/80* (2018.08)

(58) Field of Classification Search
CPC .. A61K 35/17; A61K 35/28; A61K 2035/124; A61K 2039/5152; A61K 2039/80; A61K 2300/00; A61K 45/06
See application file for complete search history.

(56) References Cited

U.S. PATENT DOCUMENTS

| | | | |
|---|---|---|---|
| 4,720,386 A * | 1/1988 | McCollester | A61K 39/0011 424/277.1 |
| 5,484,596 A | 1/1996 | Hanna et al. | |
| 7,553,661 B2 * | 6/2009 | Galipeau | A61K 35/35 435/325 |
| 2002/0018767 A1 | 2/2002 | Lee et al. | |
| 2002/0172987 A1 | 11/2002 | Terstappen et al. | |

FOREIGN PATENT DOCUMENTS

| | | | | |
|---|---|---|---|---|
| WO | WO-2005003321 A2 * | 1/2005 | | A61K 35/28 |
| WO | WO-2006109300 A1 * | 10/2006 | | A61K 2300/00 |

OTHER PUBLICATIONS

Kato et al (Bone Marrow Transplantation, 2001, vol. 28, pp. 587-595) (Year: 2001).*
Gannage et al (The Journal of Immunology, 2005, vol. 174, pp. 8210-8218) (Year: 2005).*
Filantenkov et al., "Ineffective Vaccination against Solid Tumors Can Be Enhanced by Hematopoietic Cell T ransplantation", The Journal of Immunology, Dec. 1, 2009, pp. 7196-7203, 183 (11), The American Association of Immunologists, Inc., Rockville, MD.
Anderson et al., "Enhancement of graft-versus-tumor activity and graft-versus-host disease by pretransplant Immunization of allogeneic bone marrow donors with a recipient-derived tumor cell vaccine", Cancer Research, Apr. 1999, pp. 1525-1530, vol. 59, Issue 7, American Association for Cancer Research, Philadelphia, PA.
Anderson et al., "Immunization of allogeneic bone marrow transplant recipients with tumor cell vaccines enhances graft-versus-tumor activity without exacerbating graft-versus-host disease", Blood, Apr. 1, 2000, pp. 2426-2433, 95(7), American Society of Hematology, Washington, DC.
ATCC Catalog (listing for "A20" cells, downloaded from the Web on Jul. 1, 2012).
Berd et al., "Induction of Cell-mediated Immunity to Autologous Aelanoma Cells and Regression of Metastases after Treatment with a Melanoma Cell Vaccine Preceded by Cyclophosphamide", Cancer Res., May 1986, pp. 2572-2577, 46(5), American Association for Cancer Research, Philadelphia, PA.
Brody et al., "Immunotransplantation preferentially expands T-effector cells over T-regulatory cells and cures large lymphoma tumors", Blood, Jan. 1, 2009, pp. 85-94, 113(1), American Society of Hematology, Washington, DC.
June, "Adoptive T cell therapy for cancer in the clinic", J Clin Invest, Jun. 1, 2007, pp. 1466-1476, 117(6), American Society for Clinical Investigation, Ann Arbor, MI.
Klebanoff et al., "Sinks, suppressors and antigen presenters: how lymphodepletion enhances T cell-mediated tumor immunotherapy", Trends Immunol., Feb. 2005, pp. 111-117, vol. 26, Issue 2, Elsevier, Amsterdam, Netherlands.

(Continued)

Primary Examiner — Karen A. Canella
(74) Attorney, Agent, or Firm — Pamela J. Sherwood; Bozicevic, Field & Francis LLP

(57) ABSTRACT

In one aspect, the present invention provides a method for treating cancer comprising tumor cell vaccination in combination with hematopoietic and immune cell transplantation. In some embodiments, the method involves autologous tumor cell vaccination prior to autologous hematopoietic and immune cell transplantation. In another aspect, the present invention provides a method of purifying tumor cells from a subject in preparation for vaccination.

16 Claims, 10 Drawing Sheets

Specification includes a Sequence Listing.

(56) References Cited

OTHER PUBLICATIONS

Maesawa et al., "Sensitive Detection of p53 Gene Mutations in Esophageal Endoscopic Biopsy Specimens by Cell Sorting Combined with Polymerase Chain Reaction Single-strand Conformation Polymorphism Analysis", Cancer Res Dec. 1992, pp. 1253-1256, vol. 83, Issue 12, Wiley, Hoboken, NJ.

Salgia et al., "Vaccination With Irradiated Autologous Tumor Cells Engineered to Secrete Granulocyte-Macrophage Colony-Stimulating Factor Augments Antitumor Immunity in Some Patients With Metastatic Non-Small-Cell Lung Carcinoma", J Clin Oncol., Sep. 21, 2016, pp. 624-630, 21(4), American Society of Clinical Oncology, Alexandria, VA.

Schlag et al., "Active specific immunotherapy with Newcastle-disease-virus-modified autologous tumor cells following resection of liver metastases in colorectal cancer. First evaluation of clinical response of a phase II-trial", Cancer Immunol Immunother., 1992, pp. 325-330, 35(5), Springer Nature, Basingstoke, United Kingdom.

Simons et al., "Induction of Immunity to Prostate Cancer Antigens: Results of a Clinical Trial of Vaccination with Irradiated Autologous Prostate Tumor Cells Engineered to Secrete Granulocyte-Macrophage Colony-Stimulating Factor Using ex Vivo Gene Transfer", Cancer Res., Oct. 1999, pp. 5160-5168, vol. 59, Issue 20, American Association for Cancer Research, Philadelphia, PA.

Wei et al., "Dendritoma vaccination combined with low dose interleukin-2 in metastatic melanoma patients induced Immunological and clinical responses", Int J Oncol., Oct. 17, 2005, pp. 585-593, 28(3), Spandidos Publications, London, United Kingdom.

Kemmner et al., "Separation of tumor cells from a suspension of dissociated human colorectal carcinoma tissue by means of monoclonal antibody-coated magnetic beads", Journal of Immunological Methods, Mar. 4, 1992, pp. 197-200, vol. 147, Issue 2, Elsevier, Amsterdam, Netherlands.

Wrzesinski et al., "Hematopoietic stem cells promote the expansion and function of adoptively transferred antitumor CD8+T cells", Journal of Clinical Investigation, Feb. 1, 2007, pp. 492-501, vol. 117, American Society for Clinical Investigation, Ann Arbor, MI.

DeAngelo et al. "Posttransplant Immunotherapy with a GM-CSF-Based Tumor Vaccine (GVAX®) Following Autologous Stem Cell Transplant (ASCT) for Acute Myeloid Leukemia (AML)", Blood, 2004, p. 441-445, vol. 104, American Society of Hematology, Washington, DC.

Michael et al., "Delayed Disease Progression after Allogeneic Cell Vaccination in Hormone-Resistant Prostate Cancer and Correlation with Immunologic Variables", Clinical Cancer Research, Jun. 15, 2005, pp. 4469-4478, vol. 11, American Association for Cancer Research, Philadelphia, PA.

Borrello et al., "Granulocyte-macrophage colony-stimulating factor (GM-CSF)-secreting cellular immunotherapy in combination with autologous stem cell transplantation (ASCT) as postremission therapy for acute myeloid leukemia (AML)", Blood, Aug. 27, 2009, pp. 1736-1745, vol. 114, No. 9, American Society of Hematology, Washington, DC.

\* cited by examiner

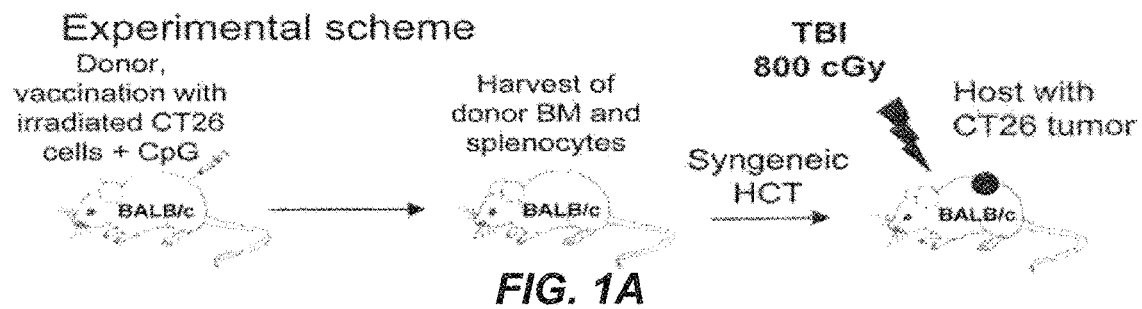
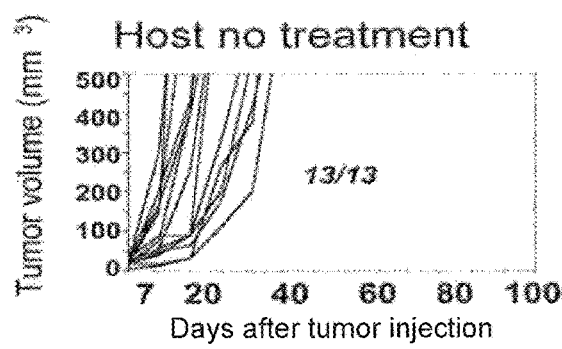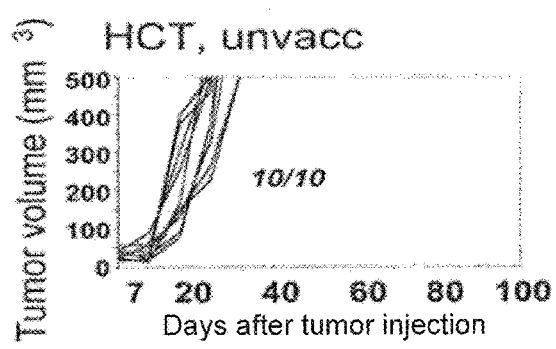
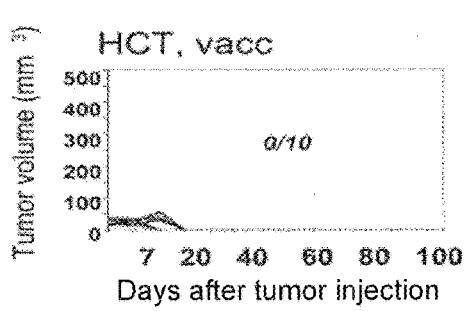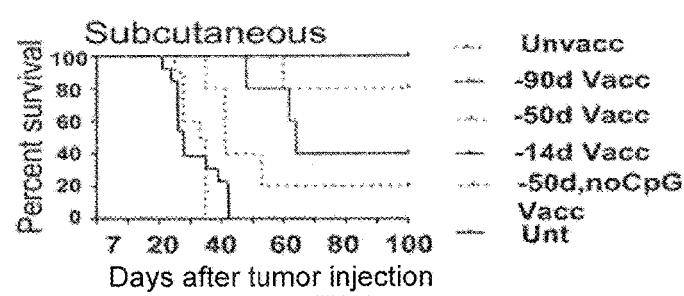
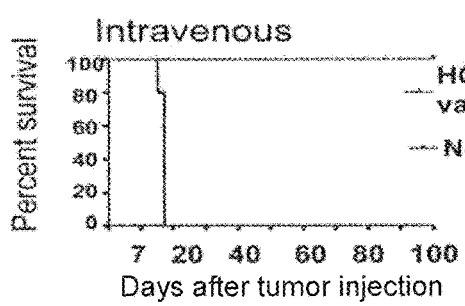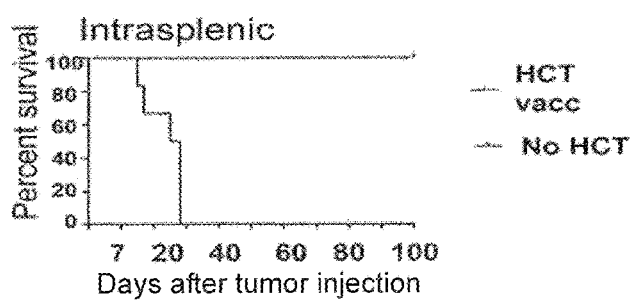

TUMOR VACCINATION IN COMBINATION WITH HEMATOPOIETIC CELL TRANSPLANTATION FOR CANCER THERAPY

CROSS REFERENCE

This application claims benefit and is a Continuation of application Ser. No. 14/921,862 filed Nov. 9, 2015, which is a Continuation of application Ser. No. 13/935,251 filed Jul. 3, 2013, now patent, U.S. Pat. No. 9,192,627 issued Nov. 24, 2015, which is a Continuation of application Ser. No. 12/592,752 filed Dec. 1, 2009, now patent, U.S. Pat. No. 8,506,954 issued Aug. 13, 2013, which applications are incorporated herein by reference in their entirety.

FEDERALLY SPONSORED RESEARCH AND DEVELOPMENT

This invention was made with Government support under contract CA049605 awarded by the National Institutes of Health. The Government has certain rights in the invention.

BACKGROUND OF THE INVENTION

Cancer, also known as malignant neoplasm, is characterized by an abnormal growth of cells that display uncontrolled cell division, invasion and destruction of adjacent tissues, and sometimes metastasis to other locations in the body. There are more than 100 types of cancer, including breast cancer, skin cancer, lung cancer, colon cancer, prostate cancer, and lymphoma. Cancer is the second leading cause of death in America and it causes about 13% of all deaths. Cancer may affect people at all ages, even fetuses, but the risk for most types of cancer increases with age. Cancers can affect all animals.

Chemotherapy has become the standard of care for many cancers. Chemotherapy refers to antineoplastic drugs used to treat cancer or the combination of these drugs into a cytotoxic standardized treatment regimen. Most commonly, chemotherapy acts by killing cells that divide rapidly, one of the main properties of cancer cells. This means that it also harms cells that divide rapidly under normal circumstances: cells in the bone marrow, digestive tract and hair follicles; this results in the most common side effects of chemotherapy—myelosuppression (decreased production of blood cells), mucositis (inflammation of the lining of the digestive tract) and alopecia (hair loss). Newer anticancer drugs act directly against abnormal proteins in cancer cells; this is termed targeted therapy.

Despite these new agents and improved combinations, the current treatment is still not effective for many types of cancers or cancers at different stages. Improved regimens and treatments are greatly needed for cancer therapy.

SUMMARY OF THE INVENTION

In one aspect, the present invention provides a method for treating cancer comprising: (a) obtaining purified tumor cells; (b) vaccinating a subject with cancer with their purified tumor cells that have been irradiated and combined with an adjuvant; (c) collecting immune and hematopoietic cells from the vaccinated subjects; and (d) injecting the collected immune and hematopoietic cells from the subject intravenously after total body irradiation of the recipient. In some embodiments, the tumor cells are purified from a tumor tissue in a tumor-bearing subject. In some embodiments, the tumor cells are purified away from stromal cells. In some embodiments, the tumor cells are purified away from immunosuppressive cells. In some embodiments, the purified tumor cells are irradiated and stimulated prior to vaccination. In some embodiments, the purified tumor cells are combined with an adjuvant. The adjuvant can be CpG or GM-CSF or other immunostimulants. In some embodiments, the donor subject is tumor-bearing. In some embodiments, the immune cells contain T cells. In some embodiments, the immune cells are added to hematopoietic progenitor cells, for example, $CD34^+$ cells. In some embodiments, the hematopoietic cells are mobilized in the vaccinated subject and enriched prior to transplantation. In some embodiments, the recipient receives a single or several doses of total body irradiation prior to transplantation with or without local irradiation of the tumor. In some embodiments, the subject is a patient diagnosed with cancer. In a preferred embodiment, the transplantation is an autologous transplantation of T cells and hematopoietic progenitor cells. In some embodiments, the subject method further comprises vaccinating the subject with irradiated tumor cells and adjuvant before the transplantation of immune and hematopoietic cells. In some embodiments, the cancer is a solid tumor. Examples of solid tumors that can be treating using the subject methods of the present invention include but are not limited to colorectal cancer, lung cancer, breast cancer, pancreatic cancer, liver cancer, prostate cancer, and ovarian cancer. In some embodiments, the tumor cells are from a primary or metastatic tumor. In some embodiments, the cancer is primary or metastatic.

In another aspect, the present invention provides a method for purifying tumor cells from vaccination comprising: (a) obtaining a tumor tissue from a subject; (b) making cell suspension of the tumor tissue; (c) separating tumor cells from the cell suspension; and (d) obtaining purified tumor cells with a purity of at least 30%. In some embodiments, the tumor is a primary tumor or a metastatic tumor. In some embodiments, the tumor is a solid tumor. The solid tumor can be a colorectal tumor, breast tumor, lung tumor, liver tumor, pancreatic tumor, prostate tumor, or ovarian tumor. In some embodiments, the subject is a patient diagnosed with cancer. In some embodiments, the tumor cells are separated from other components in the cell suspension. In some embodiments, the tumor cells are purified from immunosuppressive cells and factors present in the cell suspension. In some embodiments, the tumor cell purity is greater than 30%, 40%, 50%, 55%, 60%, 65%, 70%, 75%, 80%, 85%, 90%, 95%, or more. In some embodiments, the tumor cell purity is greater than 90%. In some embodiments, the purified tumor cells are subsequently used for vaccinating the subject from whom the tumor tissue is originally obtained. In some embodiments, the purified tumor cells are irradiated and stimulated with an adjuvant. The adjuvant can be CpG or GM-CSF or other immunostimulants.

In another aspect, the present invention provides a composition comprising purified and irradiated tumor cells from a subject. In some embodiments, the tumor cells are purified from stromal cells. In some embodiments, the tumor cells are purified from immunosuppressive cells. In some embodiments, the purified and irradiated tumor cells are stimulated prior to vaccination. In some embodiments, the purified tumor cells are combined with an adjuvant. The adjuvant can be CpG or GM-CSF or other immunostimulant. In some embodiments, the subject is a patient diagnosed with cancer. In some embodiments, the purified and irradiated tumor cells are used to vaccinate the subject. In some embodiments, the purified and irradiated tumor cells are from a solid tumor. The solid tumor includes but is not limited to colorectal tumor, lung tumor, breast tumor, pancreatic tumor, liver tumor, prostate tumor, and ovarian tumor. In some embodiments, the purified and irradiated tumor cells are from a primary or metastatic tumor. In some embodiments, the purified tumor cells have a purity greater than 30%, 40%, 50%, 60%, 70%, 80%, 90%, or 95%.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows the experimental scheme, which uses HCT from tumor-vaccinated donors to treat CT26 colon tumors in syngeneic mice. In all instances, normal BALB/c donor mice were vaccinated subcutaneously (s.c.) with 10 irradiated CT26 tumor cells mixed with 30 μg CpG, an adjuvant that stimulates antigen presenting cell via TLR-9 (12,13). After 90 days, spleen and bone marrow cells were harvested, and transplanted intravenously (i.v.) into tumor-bearing BALB/c host mice following a single dose of total body irradiation (TBI). Seven days prior to TBI, hosts had been given live tumor cells via s.c. ($2.5 \times 10^4$), i.v. ($2 \times 10^5$) or intrasplenic ($5 \times 10^5$) routes.

Figure 1H:
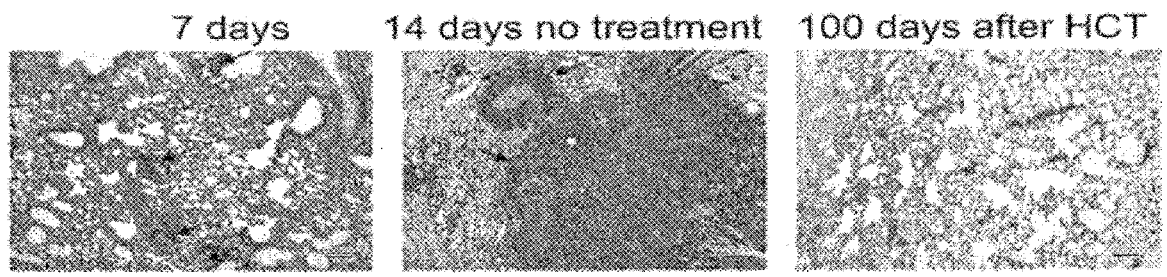
FIG. 1A-1.
FIG. 1B shows the progressive growth of s.c. tumors in all untreated mice. Similarly, tumor bearing recipients of 50×10 bone marrow cells and 60×10 spleen cells from unvaccinated donors had uniformly progressive tumors (FIG. 1C). In contrast, after HCT from vaccinated donors, tumor bearing mice displayed a steady regression of tumor volume over a 100 day observation period (FIG. 1D), which remained stable until the end of study (day 180; data not shown). Shortening the time interval between immunization of the donor and harvesting the graft from 90 to 14 days, but not to 50 days, resulted in lower anti-tumor effect (p=0.005 and p=0.3, respectively; log rank test.
FIG. 1E). Omission of CpG from the donor vaccine resulted in a further loss of efficacy (p=0.01), and only 20% of hosts survived 100 days.
Figure 1I:
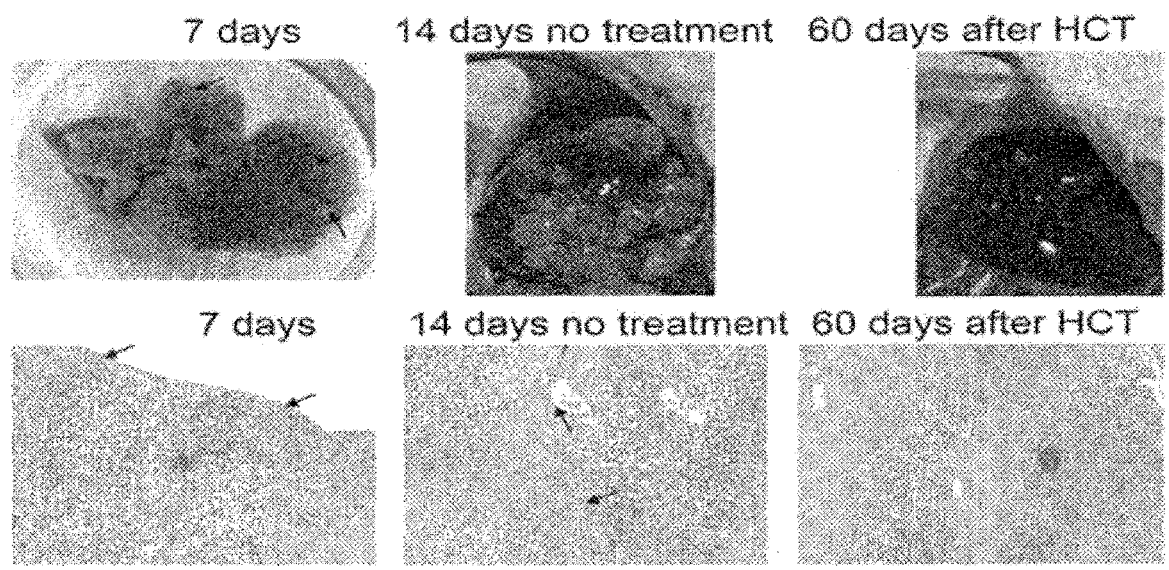

The same HCT strategy was also successful in recipients given tumor cells by i.v. administration. By day 7, tumor cells had disseminated into the lungs and formed multiple tumor clusters (FIG. 1H). By day 20 all untreated control mice succumbed to progressive disease with large, nearly confluent tumor nodules (FIGS. 1F and 1H). In contrast, recipients of HCT from vaccinated donors all survived at least 100 days, with no histologic evidence of residual tumor (FIG. 1H). Accordingly, improvement of survival was significant as compared to untreated mice (p<0.01) (FIG. 1F). When tumor cells were injected into the spleen, by day 7 tumor nodules became established in the parenchyma of the liver (FIG. 1I), and by day 14 there was evidence of blood vessel invasion (arrows, FIG. 1I). All untreated animals died by day 30 (FIG. 1G) with multiple visible, as well as microscopic, tumors. Treated mice survived beyond day 100 (FIG. 1G), easily exceeding the survival of untreated mice (p=0.001). The liver of treated mice displayed no abnormalities and also no histologic evidence of residual tumor at day 60 (FIG. 1I). HCT from vaccinated donors also cured peritoneal carcinomatosis, which had been created by intraperitoneal injection of 5×10 tumor cells and which displayed multiple peritoneal nodules and ascites by the time of transplant (data not shown). All untreated mice died by day 20, and all transplanted mice survived at least 100 days without any peritoneal tumor growth.

Figure 2A:
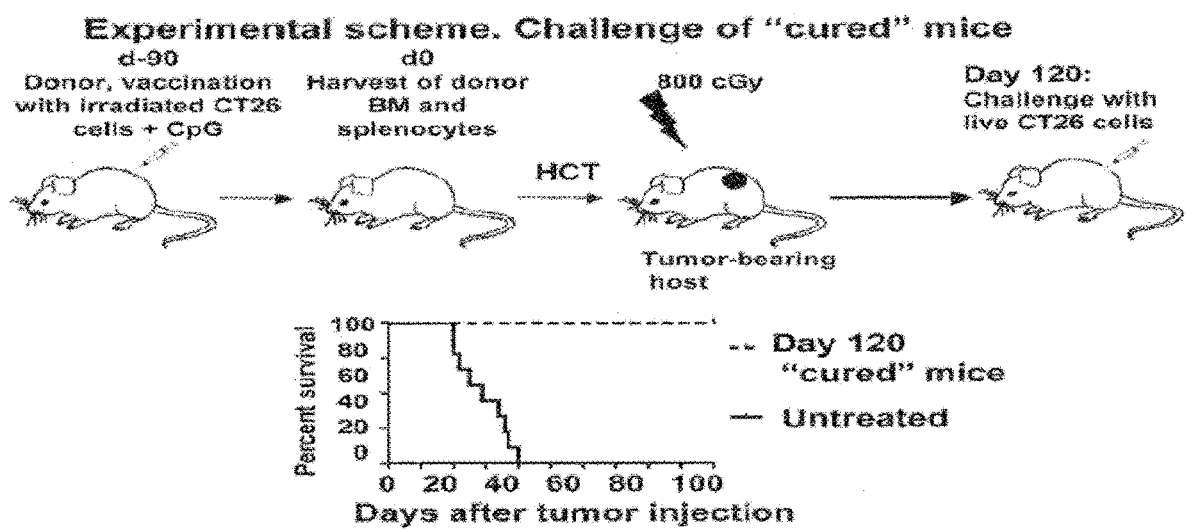
Figure 2B:
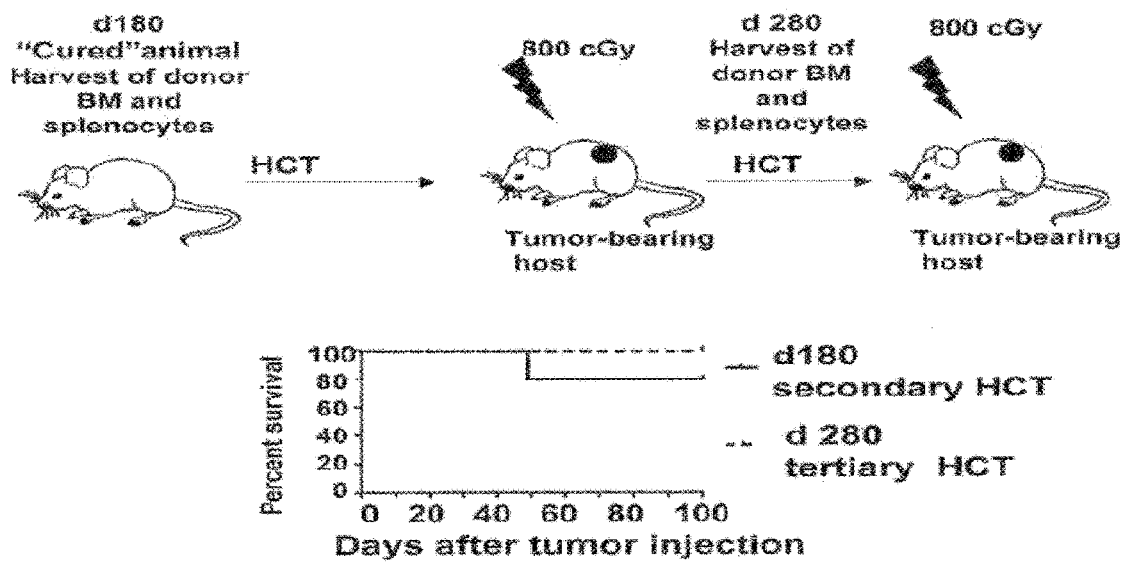

FIG. 2A-2B shows that "cured" animals are protected from tumor challenge and can serve as donors of immune cells for HCT into syngeneic tumor-bearing hosts. FIG. 2A shows the animals with a single subcutaneous nodules cured by HCT from vaccinated animals were challenged at day 24 with live tumor cells subcutaneously. p<0.001 for "cured" animals (n=5) vs untreated controls (n=9). FIG. 2B shows the bone marrow and splenocytes from "cured" animals were harvested at day 180 and transferred into lethally irradiated tumor-bearing hosts. 100 days after bone marrow and splenocytes were harvested from secondary hosts and transferred into lethally irradiated tumor-bearing hosts. p<0.001 for transplanted animals (n=5) vs untreated (n=9) controls.

To assess the duration of effect of vaccination combined with HCT, "cured" animals from the experiment in FIG. 1D were challenged with $2.5 \times 10^4$ live tumor cells at day 24 as shown in the experimental scheme in FIG. 2A. The results show that these animals were completely protected and survived for at least 100 days (FIG. 2A). Moreover, harvesting of spleen and bone marrow cells from "cured" recipients at day 180 after HCT, and secondary transfer resulted in 80% of the new recipients surviving for more than 100 days (FIG. 2B). At least 100 days later those secondary recipients were used as donors for another HCT into irradiated tumor-bearing tertiary hosts which was also effective since all tertiary hosts survived more than 100 days (FIG. 2B). Thus, anti-tumor immunity generated by a single vaccination could eradicate tumors 370 days later (FIG. 2B).

Figure 3A:
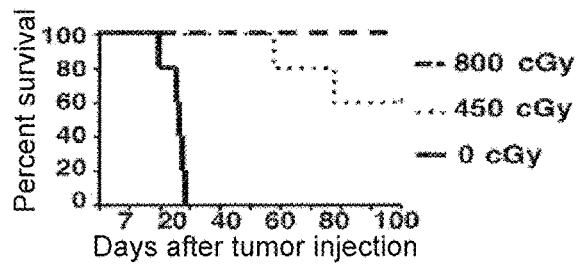
Figure 3B:
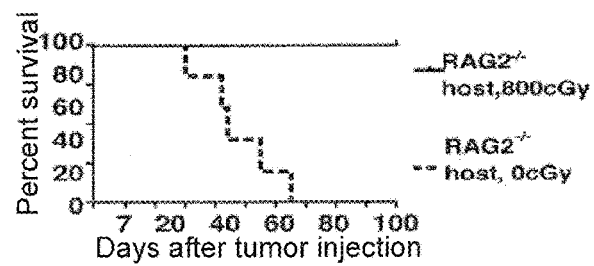
Figure 3C:
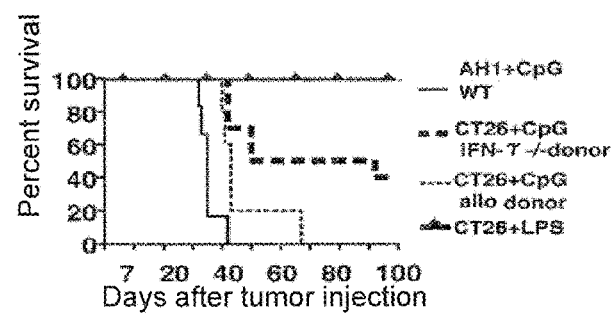
Figure 3D:
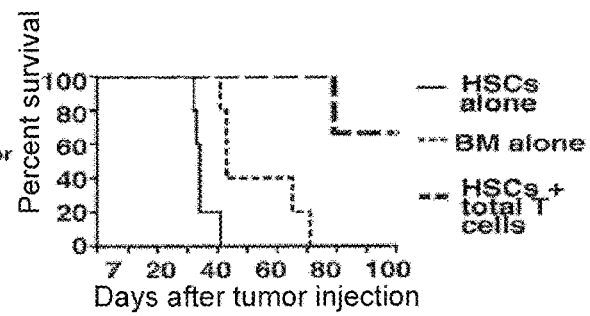
Figure 3E:
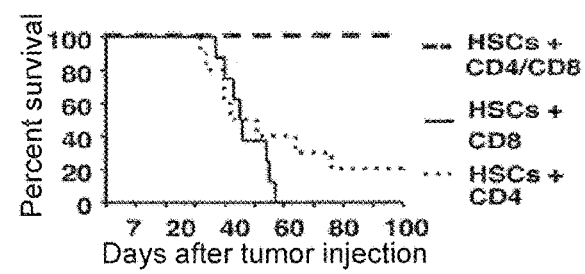
Figure 3F:
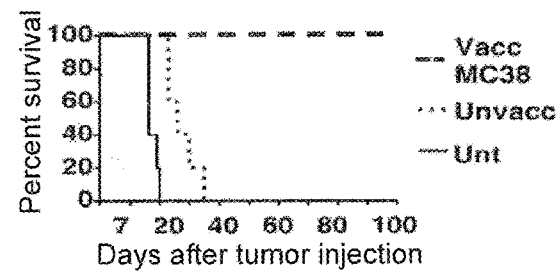
Figure 3G:
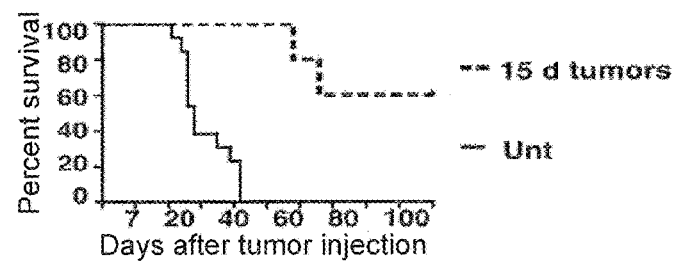

FIG. 3A-3G shows requirements for host irradiation and donor T cells in transplants. FIG. 3A shows the survival of BALB/c hosts that received either 800 cGy TBI (n=5), 450 cGy TBI (n=5) or no conditioning (n=5) before transplantation. p<0.05 for 800 cGy vs 450 cGy and p<0.0001 for 800 cGy vs 0 cGy. FIG. 3B shows the Rag $2^{-/-}$ BALB/c hosts received transplants after either 800 cGy TBI (n=5) or no irradiation (n=5). p=0.001 for irradiated RAG2$^{-/-}$ vs unirradiated. FIG. 3C shows the BALB/c hosts received transplants from BALB/c IFN-γ donors (n=10)(p=0.004), DBA/2J donors (n=5)(p<0.001) or BALB/c donors vaccinated with either AH-1 peptide and CpG (n=6)(p<0.0001) or irradiated tumor cells and lipopolysaccharide (LPS) instead of CpG (n=5) (p=1.0). (Survival compared with 90 day CpG group from FIG. 1E). FIG. 3D shows the hosts were given either donor whole bone marrow cells (n=5), or c-kit$^+$Sca-1$^+$ HSCs alone (n=5), or HSCs and purified splenic T cells (n=6) (p=0.008). FIG. 3E shows the hosts received HSCs with either CD4$^+$ (n=10) or CD8$^+$ (n=8) T cells, or transplants containing a mixture of CD4$^+$ and CD8$^+$ T cells (n=5) (p<0.008). FIG. 3F shows the survival of C57BL/6 mice with MC38 subcutaneous colon tumor nodules given TBI and transplants from C57BL/6 donors that had been vaccinated with irradiated MC38 tumor cells and CpG (n=10) as compared with untreated control mice (n=5). (p<0.008). FIG. 3G shows the survival of hosts (n=5) with large subcutaneous tumors established for 15 days after HCT from vaccinated donors compared with survival of untreated animals (p=0.0005).

FIG. 3A illustrates the significant role of the host conditioning regimen in our vaccine strategy. All tumor bearing recipients of bone marrow and splenocytes from vaccinated donors were cured when conditioned with myeloablative TBI (800 cGy). In contrast, only 60% of hosts survived 100 days with a non-myeloablative radiation dose (450 cGy) (p<0.05), while none survived more than 40 days without irradiation (p<0.0001). Radiation causes lymphodepletion which might deplete host regulatory T cells that suppress anti-tumor immune responses. In order to test whether radiation mediates tumor eradication through such a mechanism, we studied unirradiated tumor-bearing RAG2$^{-/-}$ recipients that lack T cells. Rag 2$^{-/-}$ BALB/c hosts were given myeloablative radiation or no radiation immediately before transplantation of cells from vaccinated donors. FIG. 3B shows that although there was a significant delay in mortality in non-irradiated Rag 2–/– mice as compared to non-irradiated wild type mice (p=0.001), all mice died by day 65. Conditioning of the Rag 2$^{-/-}$ mice with 800 cGy resulted in significant improvement in survival as compared to the non-irradiated mice (p=0.001), and all hosts survived at least 100 days (FIG. 3B).

When IFNγ$^{-/-}$ BALB/c mice were vaccinated and used as bone marrow and splenocyte donors, the survival of hosts was decreased as compared to wild type syngeneic donors (p=0.004) (FIG. 2C). Likewise, survival was reduced in all five mice given grafts from vaccinated MHC-matched, minor antigen-mismatched DBA/2J donors (H-2$^d$) (p<0.001) (FIG. 3C). While 4/5 animals had progressive tumor growth, one mouse displayed tumor regression, but succumbed due to GVHD. Substitution of whole tumor cells with the tumor-associated immunodominant AH-1 peptide (4) for vaccination of donors resulted in decreased survival (p<0.0001) (FIG. 3C). Use of lipopolysaccharide (30 µg) as an adjuvant for vaccination was just as effective as CpG, based on survival of hosts post-HCT (p=1.0) (FIG. 3C). Grafts from vaccinated donors consisting of bone marrow or FACS-purified c-kit$^+$Sca1$^{high}$lin$^-$ hematopoietic stem cells (HSC) failed to prevent tumor progression (FIG. 3D). Addition of 5×10 splenic T cells to the HSCs increased survival (p=0.008) such that the majority of hosts were alive at 100 days without detectable tumors (FIG. 3D). When HSC grafts were supplemented with both CD4$^+$ (3.5×10) plus CD8$^+$ T cells (1.8×10), survival was improved (p<0.008) as compared to supplementation with CD4$^+$ or CD8$^+$ T cells only (FIG. 3E).

The utility of HCT from vaccinated donors was further validated in studies of another colon cancer, MC38, which grows only in C57BL/6 (H-2$^b$) mice (8). For these experiments, donor mice were vaccinated with 1×10 MC38 tumor cells (FIG. 3F). Again, while syngeneic recipients of grafts from vaccinated donors were cured, recipients of transplants from unvaccinated donors did not survive beyond 35 days (p<0.0001). HCT from tumor-vaccinated donors could also significantly improve survival of animals with large (>10 mm) tumors established for 15 days (p=0.0005) (FIG. 3G). After 100 days, 60% of treated animals were completely tumor free.

Figure 4A:
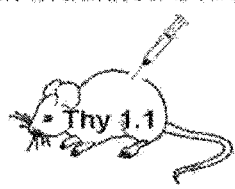
Figure 4A:
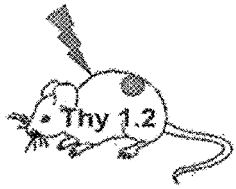
Figure 4B:
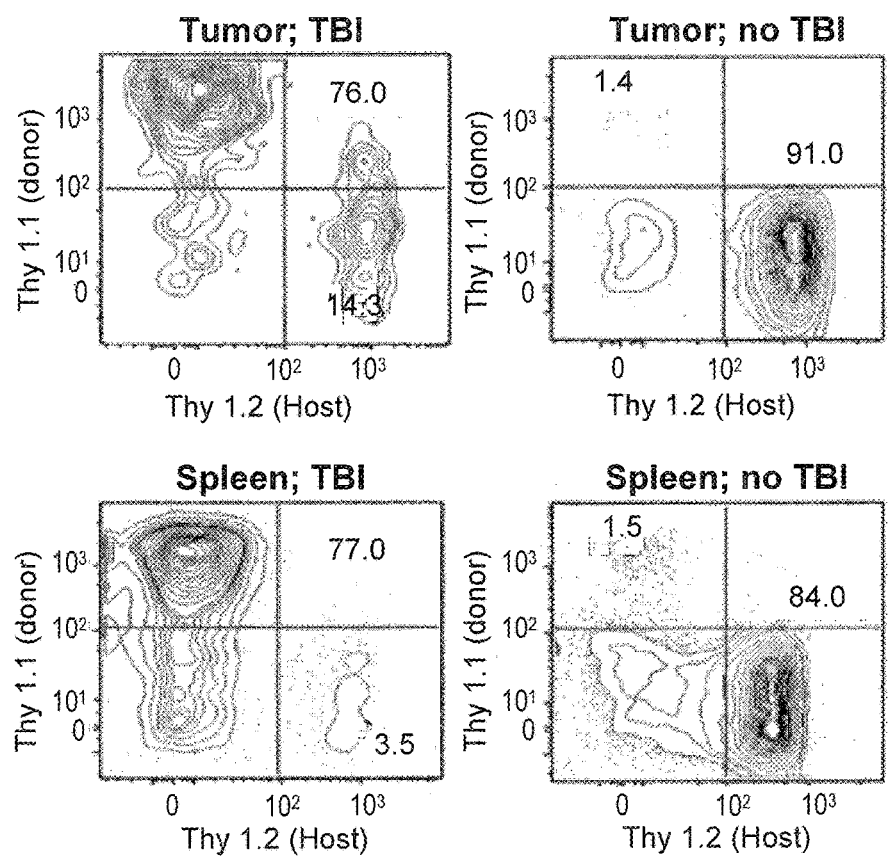
Figure 4C:
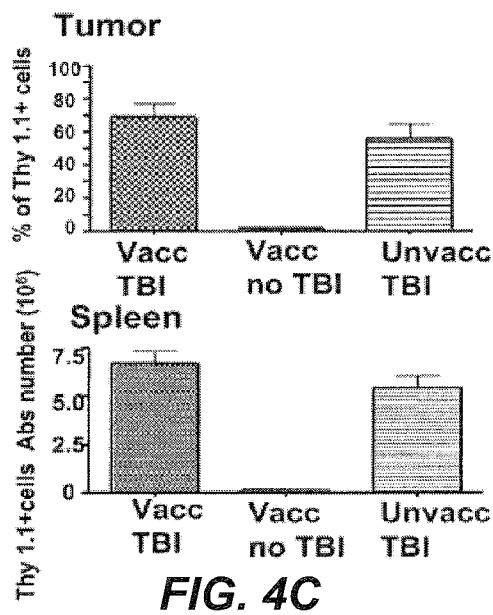
Figure 4D:
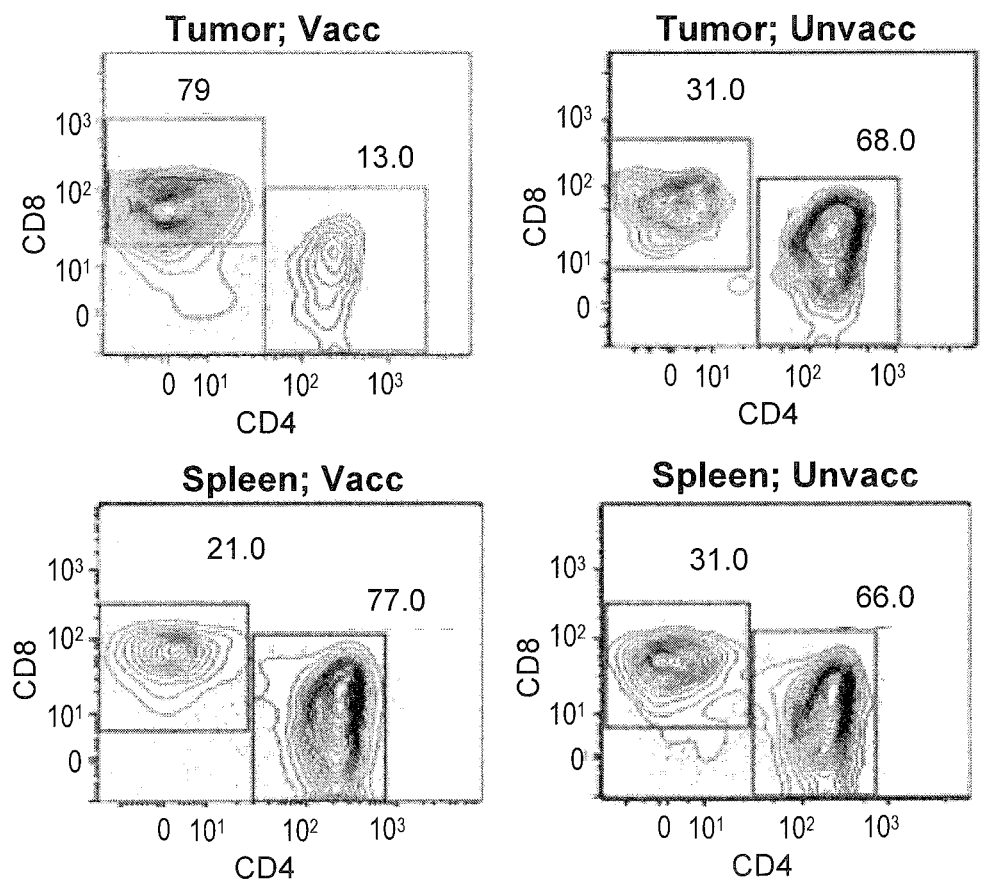
Figure 4E:
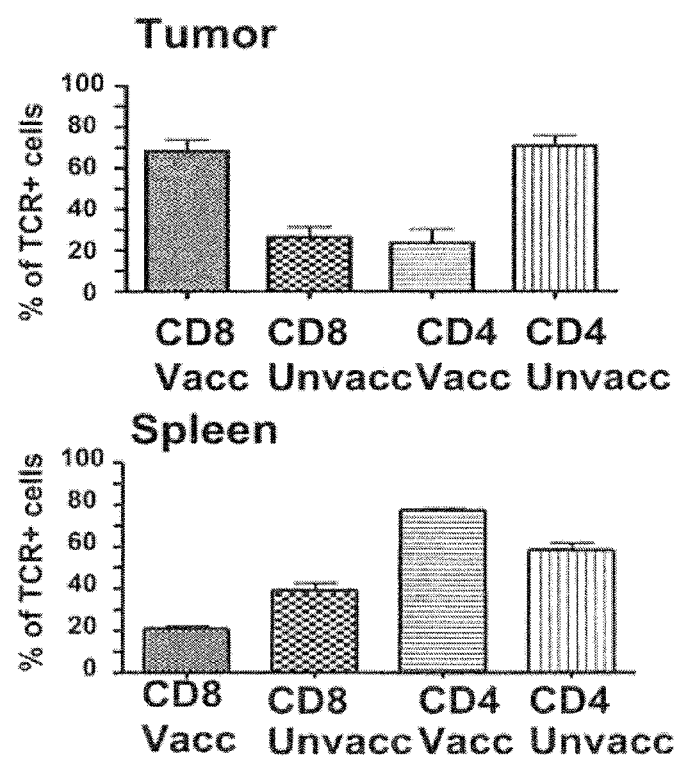

FIG. 4A-4E shows that donor T cells accumulate in host tumors after transplantation. FIG. 4A shows the experimental scheme. FIG. 4B shows the Thy 1.1 and Thy 2.2 analysis of single cell suspensions of the tumors and spleens obtained on day 28 from tumor-bearing hosts given unvaccinated or vaccinated donor transplants with or without TBI. FIG. 4C shows the mean percentages and SE of tumor-infiltrating Thy1.1$^+$ cells at day 28 in top panel (n=5 in each group). Mean absolute numbers of Thy1.1$^+$ cells in the host spleen in bottom panel (n=5). (p<0.001 for differences between TBI and no TBI, and p>0.05 for unvaccinated donors vs vaccinated after TBI). FIGS. 4D and 4E show the analysis of CD4$^+$ and CD8$^+$ T cells among Thy1.1+ cells. Vaccinated donors are compared with unvaccinated donors (n=5 in each group) (p<0.001 for tumors and p<0.001 for spleens).

To delineate the donor-derived cell populations involved in the anti-tumor response, bone marrow and spleen cells were transplanted from BALB/c Thy1.1 donors into tumor bearing BALB/c Thy 1.2 hosts, as depicted in FIG. 4A. To assure that there would be sufficient donor cells for analysis at day 28, HCT was performed in animals bearing tumors that had been established for 14 instead of 7 days. In irradiated recipients of vaccinated donor grafts approximately 70% of T cells infiltrating the tumors were of donor origin (FIGS. 4B and 4C), while donor T cells accounted for <2% of tumoral T cells when hosts were not irradiated (p<0.001). A similar facilitation of donor cell accumulation in the spleen was observed in irradiated versus non-irradiated hosts (p<0.01) (FIGS. 4B and 4C). Differences in accumulation of total T cells from vaccinated and unvaccinated donors were not significant (p>0.05). However, the majority of tumor T cells from vaccinated donors were CD8$^+$, whereas most of the tumoral T cells from unvaccinated donors were CD4+(p=0.01) (FIGS. 4D and 4E). CD4$^+$ T cells were in the majority in the spleens with both vaccinated and unvaccinated donors (p<0.001).

Figure 5A:
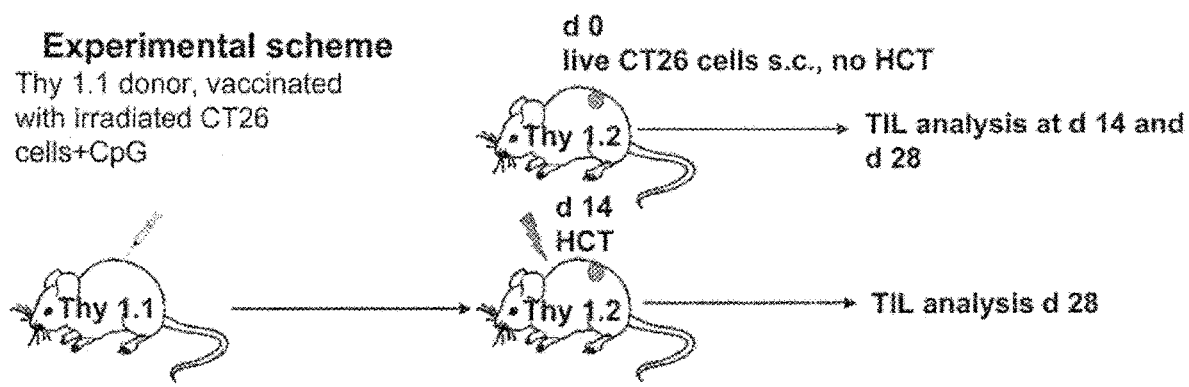
Figure 5B:
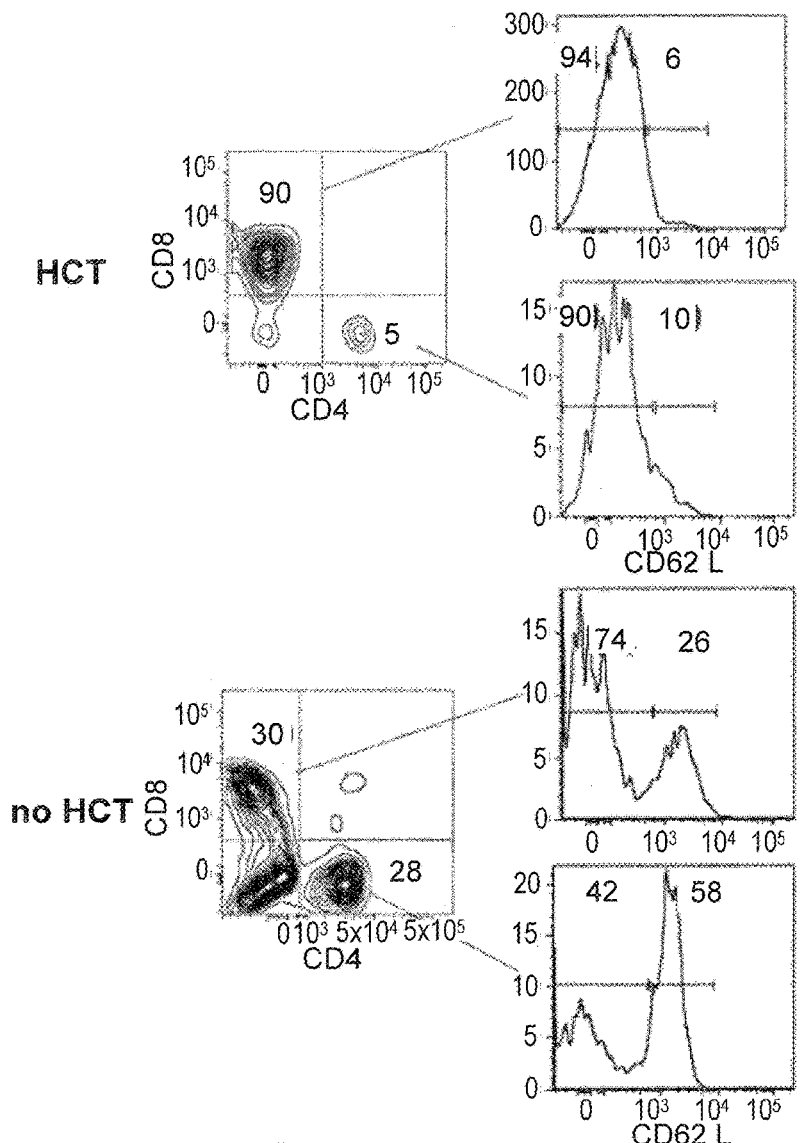

FIG. 5A-5E shows that the effector/regulatory T cell ratios changes in favor of CD8 effector memory cells as a result of vaccination and HCT. FIG. 5A shows the experimental scheme. Syngeneic Thy 1.1 donors were vaccinated with 10 irradiated CT26 cells and CpG. Bone marrow and splenocytes were transplanted into lethally irradiated Thy 1.2 hosts with s.c. tumors established for 14 days. Tumor-infiltrating cells and host spleens were analyzed d 14 after HCT (28 days after tumors were induced). Control tumor-bearing animals did not receive irradiation and HCT. FIG. 5B shows the analysis of CD62L expression on CD8$^+$ and CD4$^+$ tumor-infiltrating T cells form irradiated hosts that received HCT (gated Thy1.1$^+$ cells) or untreated control animals (no HCT)(gated Thy1.2$^+$ cells) at day 28. The data are representative for the group of animals (n=5).

Figure 5C:
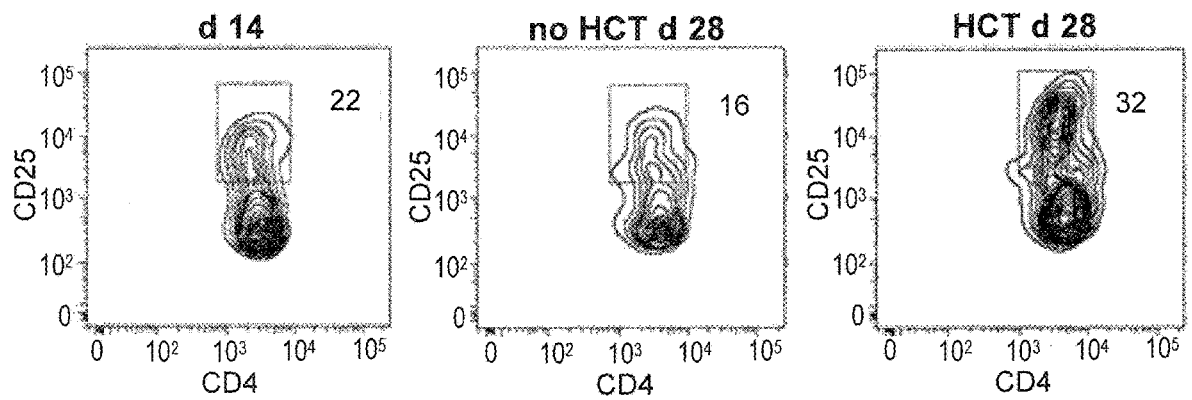
Figure 5D:
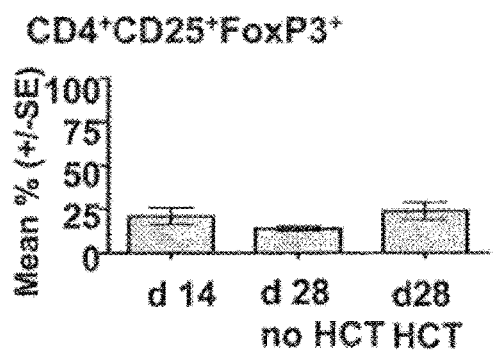
Figure 5E:
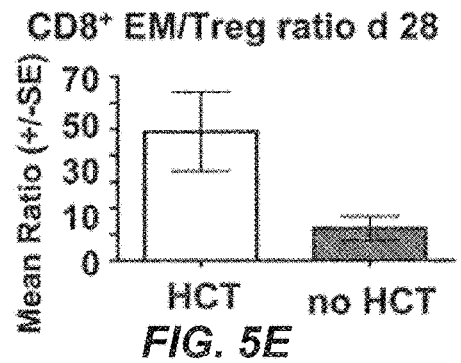

FIGS. 5C and 5D show the CD25 expression of tumor-infiltration CD4$^+$ T cells and analysis of CD4+CD25+Foxp3$^+$ T cells in tumors obtained from untreated animals on day 14, untreated animals on day 28 as well as tumor-bearing animals that received HCT (day 28). Mean percentages and SE are shown (n=5 in each group). FIG. 5E shows the CD8$^+$ effector memory/Treg ratio in tumors in animals receiving HCT versus untreated animals on day 28. Mean percentages and SE are shown (n=5 in each group) (p<0.05).

Previous studies have shown that CD4$^+$CD25$^+$FoxP3$^+$ Treg cells can suppress tumor immunity (14). Moreover, this suppression was mediated at the tumor site and was lost after intra-tumoral depletion of Tregs (14). It is shown above (FIG. 3B) that conditioning and HCT was required to cure tumors in RAG2$^{-/-}$ mice lacking T regulatory cells. Thus, the requirement for irradiation is not based on host Treg depletion.

However, regulatory T cells of donor or host origin may be capable of infiltrating tumors when wild-type hosts are used. Host and donor T cell subsets infiltrating CT26 subcutaneous tumor nodules were examined in wild-type BALB/c mice before and after HCT, and in controls without HCT as shown in the experimental scheme in FIG. 5A. Control Thy1.2 mice given CT26 cells subcutaneously were euthanized 14 or 28 days later, and single cell suspensions from tumors were analyzed for tumor infiltrating T lymphocytes (TIL) subsets.

Experimental mice were lethally irradiated and given HCT from vaccinated Thy 1.1 donors after 14 days of tumor growth, and tumor cell suspension were analyzed 14 days after HCT. FIG. 5B shows the representative staining patterns for CD4$^+$ and CD8$^+$ T cells in cell suspensions using gated Thy1.2$^k$ T cells from control mice and gated Thy1.1$^+$ from mice given HCT at 28 days after the subcutaneous injection of tumor cells (14 days after HCT).

Whereas CD8$^+$ and CD4$^+$ cells accounted for about 90% and 5% respectively of Thy1.1$^+$ cells in mice given HCT, the CD8$^+$ and CD4$^+$ cells accounted for 30% and 28% respectively of Thy1.2$^+$ cells in mice without HCT. Almost all of the CD8$^+$ and CD4$^+$ T cells in mice given HCT were CD62L$^{lo}$ (FIG. 5B). The staining pattern indicates that few naïve or central memory cells were found in these tumors, almost all were effector memory cells, since the CD8$^+$ and CD4$^+$ cells were almost all CD44$^{hi}$.

In contrast, the gated CD8$^+$ and CD4$^+$ cells from tumors in control mice contained discrete subsets of both CD62 L$^{low}$ and CD62 L$^{hi}$ cells. The CD62 L$^{hi}$ cells accounted for 26% of CD8$^+$ cells and 58% of CD4$^+$ cells (FIG. 5 B). Staining of gated CD4$^+$ tumor cells from control mice and those given HCT for CD4 versus CD25 showed that about 16% of CD4$^+$ cells were CD25$^+$ in controls, and 32% were CD25$^+$ in those given HCT at the day 28 time point (FIG. 5C). At day 14, 22% of CD4$^+$ cells were CD25$^+$. The results of additional staining for intracellular FoxP3$^+$ showed that the mean percentage of CD4$^+$CD25$^+$FoxP3$^+$ Treg cells among gated CD4+ cells in the tumors of all 3 groups of mice varied from about 15% to 25% (FIG. 5D).

The differences in the means were not statistically significant (p>0.05) as judged by the Student t test. Despite the similar percentages of Treg cells among total CD4$^+$ T cells in the tumor cell infiltrate, there was a marked difference in the balance of CD8$^+$CD62 L$^{lo}$CD44$^{hi}$ effector memory T cells versus Treg cells. Whereas, day 28 tumors from control mice showed a mean ratio of about 5:1 CD8$^+$ effector memory to Treg cells in the infiltrate, the day 28 tumors from mice given HCT showed mean ratio of about 50:1. The differences in ratios were statistically significant (p<0.05). Thus, while HCT did not deplete Tregs at the tumor site, the balance of tumor infiltrating cells was altered to favor CD8$^+$ effector memory T cells as compared to Treg cells.

Figure 6A:
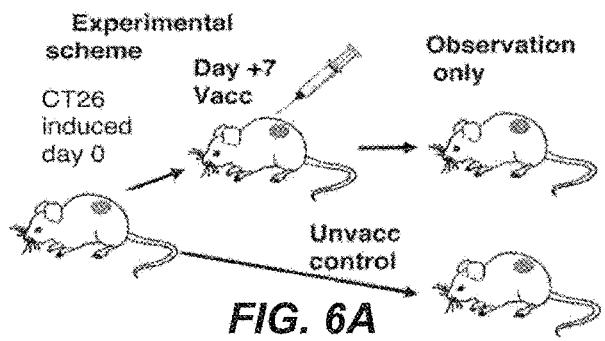
Figure 6B:
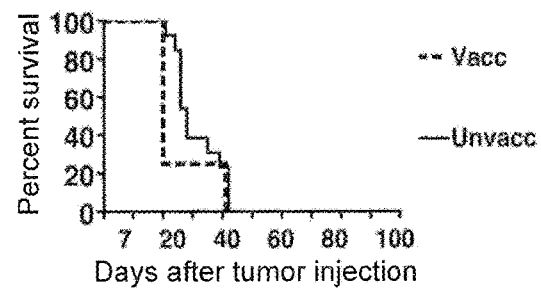
Figure 6C:
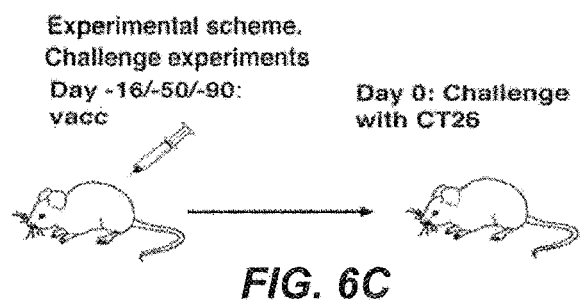
Figure 6D:
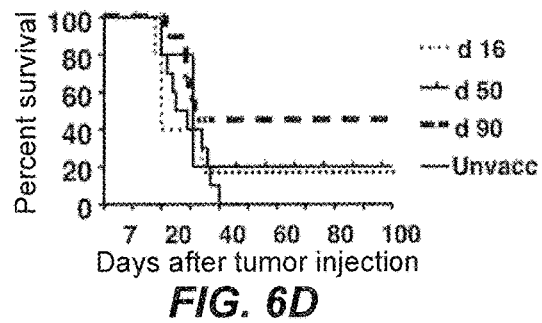
Figure 6E:
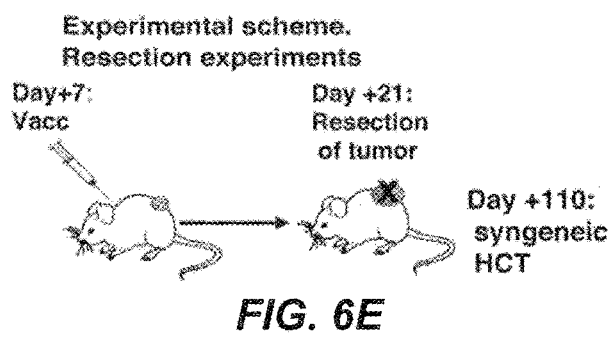
Figure 6F:
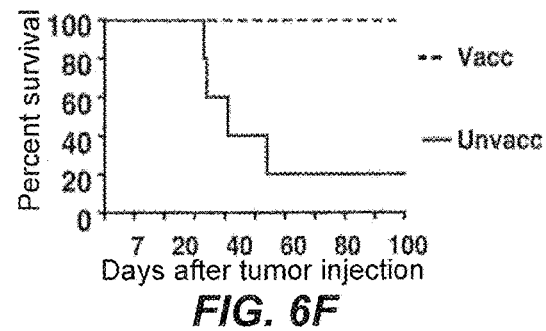
Figure 6G:
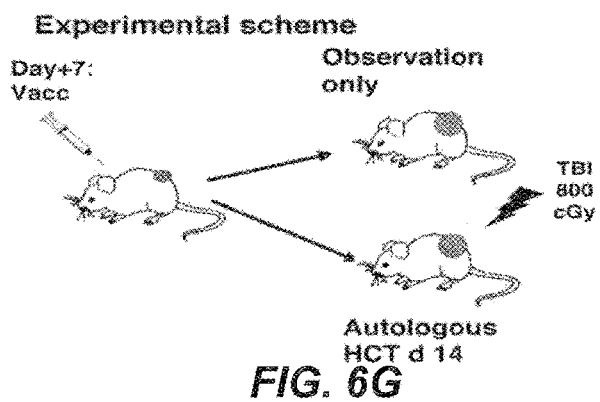
Figure 6H:
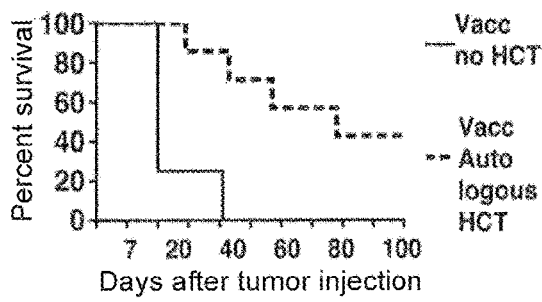

FIG. 6A-6H shows that tumor vaccination without HCT is not effective, but vaccination combined with HCT is highly effective, even in the presence of growing tumor. FIG. 6A shows the experimental scheme. Tumors were induced subcutaneously at day 0. Animals were unvaccinated or vaccinated at day 7 with irradiated tumor cells and CpG. FIG. 6B shows the survival of vaccinated versus unvaccinated mice (n=8). FIG. 6C shows the non tumor-bearing animals were vaccinated with irradiated tumor cells and CpG, and challenged with live tumor cells 16 (n=5), 50 (n=5) or 90(n=10) days after vaccination. p=0.03 for 90 days vaccination vs control. FIG. 6D shows the survival of vaccinated mice after tumor challenge. FIG. 6E shows the experimental scheme. Mice with subcutaneous tumors were vaccinated at day 7 after tumor was induced. Tumors were resected at day 21. At day 110 after tumor induction, bone marrow and splenocytes were harvested and transferred into lethally irradiated tumor-bearing hosts, FIG. 6F shows the survival of hosts given bone marrow and spleen cell transplants from vaccinated or unvaccinated donors (n=5 each group) (p<0.05). FIG. 6G shows the donors were injected with tumor cells on day 0, vaccinated on day 7 and splenectomized on day 14. Splenectomized donors had their abdominal incisions closed with surgical sutures before receiving a single dose of 800 cGy TBI. Within 6 hours of TBI, the donors were given an autotransplant of all harvested spleen cells injected intravenously. FIG. 6H shows the survival of hosts with (n=7) and without (n=8) autologous HCT (p<0.001).

FIG. 6A shows the experimental scheme used to determine the effect of vaccination alone on survival of tumor-bearing mice. FIG. 6B shows that the survival of vaccinated, but not HCT treated, animals with 7-day tumors did not improve as compared to unvaccinated tumor-bearing animals and all animals died by day 40. Moreover, when vaccinated non tumor-bearing animals were challenged with as few as 2.5×10$^4$ CT26 cells 16 and 50 days after vaccination (FIG. 6C), only 20% of mice survived 100 days (FIG. 6D). Some degree of protection developed in animals vaccinated given the tumor challenge 90 days after vaccination, as indicated by the observation that 50% of animals remained tumor free (p=0.03) (FIG. 6D). Next, to assess the potential effect of larger tumors on the response to vaccination, we vaccinated mice with tumors growing for 7 days and then waited 14 additional days before resecting the growing tumors at day 21 (FIG. 6E). Bone marrow and splenocytes were harvested from donors on day 110 and transferred into lethally irradiated tumor-bearing hosts. All hosts survived with complete tumor regression for at least 100 days (FIG. 6F). Only 20% of hosts given transplants from unvaccinated donors survived 100 days, and the difference using vaccinated versus unvaccinated donors was significant (p<0.05) (FIG. 6F). Thus, HCT from vaccinated animals into syngeneic tumor bearing hosts resulted in cure of tumors, indicating that growing tumors in donors do not prevent the development of potent anti-tumor effector cells in adoptive hosts.

A model of autolous HCT was studied as shown in FIG. 6G. In this scheme a group of donors was vaccinated 7 days after live tumor cell injection, splenectomized 7 days later, conditioned with TBI immediately after recovery from surgery, and spleen cells were injected intravenously within 6 hours after TBI. Bone marrow cells were not required for rescue of these myeloablated hosts, since mouse spleen cells contain both immune cells and HSCs. Donors that received the autologous transplants had significantly improved survival as compared to those without transplants, and about 40% survived at least 100 days with complete tumor regression (p<0.001) (FIG. 6H). Thus, large 14 day tumors were either cured or their growth significantly delayed after autologous HCT.

DETAILED DESCRIPTION OF THE INVENTION

The present invention provides methods for treating cancer comprising the steps of a) obtaining purified tumor cells; b) vaccinating a donor subject with the purified tumor cells;

c) collecting immune cells from the vaccinated donor; and d) transplanting the collected hematopoietic cells and immune cells from the donor into a tumor-bearing recipient following total body irradiation of the recipient. Also provided by the present invention is a method for purifying tumor cells from vaccination comprising: a) obtaining a tumor tissue from a subject; b) making cell suspension of the tumor tissue; and c) separating tumor cells from the cell suspension; and d) obtaining purified tumor cells with a purity of at least 30%, 35%, 40%, 45%, 50%, 55%, 60%, 65%, 70%, 75%, 80%, 85%, 90%, 95%, 2%, 3%, 98%, 99% or more.

In some embodiments, the tumor cells are purified from a tumor tissue in a tumor-bearing subject. In some embodiments, the tumor cells are purified by density gradients using Ficoll or Percoll—followed by centrifugation. In some embodiments, the tumor cells are purified by staining for cell surface markers that recognize tumor cells, and subsequent separation of positive staining cells. Following purification, tumor cells are irradiated and then stimulated with an adjuvant. Examples of adjuvant that can be used in the subject methods of the present invention include but are not limited to various toll-like receptor (TLR) stimulants such as CpG, Lipopolysaccharide (LPS), poly-IC, and cytokines such as granulocyte-macrophage colony-stimulating factor (GM-CSF).

In some embodiments, the present invention provides a method of treating cancer comprising obtaining purified tumor cells from a cancer patient; vaccinating the patient with the tumor cells mixed with an adjuvant; collecting hematopoietic cells and immune cells from the vaccinated patient; and performing autologous transplantation of the collected hematopoietic cells and immune cells back into the patient following total body irradiation of the patient. In some embodiments, the immune cells are T cells. In some embodiments, the hematopoietic cells are CD34$^+$ progenitor cells. Examples of cancer that can be treated by the subject methods of the present invention include but are not limited to solid tumors such as colorectal cancer, lung cancer, pancreatic cancer, breast cancer, prostate cancer, liver cancer, and ovarian cancer. The tumor can be primary or metastatic.

Cancer Immunotherapy

In one aspect, the present invention discloses a method for treating cancer via tumor vaccination followed by autologous hematopoietic and immune cell transplantation. The method comprises a) obtaining purified tumor cells; b) vaccinating a donor subject with the purified tumor cells; c) collecting immune cells from the vaccinated donor; and d) transplanting the collected immune cells from the donor into a tumor-bearing recipient following total body irradiation of the recipient.

Cancer immunotherapy is the use of the immune system to reject cancer. The main premise is stimulating the patient's immune system to attack the malignant tumor cells that are responsible for the disease. This can be either through immunization of the patient, in which case the patient's own immune system is trained to recognize tumor cells as targets to be destroyed, or through the administration of therapeutic antibodies as drugs, in which case the patient's immune system is recruited to destroy tumor cells by the therapeutic antibodies.

Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control. In spite of this fact, however, many kinds of tumor cells display unusual antigens that are either inappropriate for the cell type and/or its environment, or are only normally present during the organisms' development (e.g. fetal antigens). Examples of such antigens include but are not limited to the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. Other kinds of tumor cells display cell surface receptors that are rare or absent on the surfaces of healthy cells, and which are responsible for activating cellular signal transduction pathways that cause the unregulated growth and division of the tumor cell. Examples include ErbB2, a constitutively active cell surface receptor that is produced at abnormally high levels on the surface of breast cancer tumor cells.

Vaccines have been tested to be able to induce integrated immune responses composed of target-specific antibodies and CD4+ and CD8+T lymphocytes, all of which are held to be essential for effective long-term control of cancer. Insights from these studies have generated a strong framework for the selection of components that will likely comprise an ideal therapeutic cancer vaccine, including: multiple cancer-antigens in various forms delivered with potent adjuvants and all administered in a prime-boost setting in conjunction with a modulator of cancer immunosuppression. In one example, a skin cancer patient has been treated using immune cells cloned from his own immune system, i.e. autologous cells, which were then re-injected into the patient. The term "autologous" in the context of transplantation typically refers to the situation in which the donor and recipient are the same person. An autologous graft is providing a graft, for example of skin, to the same person from which the graft is obtained. The patient, who was suffering from advanced skin cancer, was free from tumors within eight weeks of being injected with autologous immune cells. This result implicates that autologous transplantation can be an effective treatment of cancer in general.

Another approach to therapeutic anti-cancer vaccination is to generate the immune response in situ in the patient. One example is OncoVEX GM-CSF. OncoVEX GM-CSF is a version of herpes simplex virus which has been engineered to replicate selectively in tumor tissue and also to express the immune stimulatory protein GM-CSF. This enhances the anti-tumor immune response to tumor antigens released following lytic virus replication providing an in situ, patient specific anti-tumor vaccine as a result. Effective cancer vaccines seek to target an antigen specific to the tumor and distinct from self-proteins. Selection of the appropriate adjuvant, molecules that activate antigen-presenting cells to stimulate immune responses, is required; at the present time, only BCG, aluminum-based salts and a squalene-oil-water emulsion are approved worldwide for clinical use. The effective vaccine also should seek to provide long term memory to prevent tumor recurrence. Preferably, both the innate and adaptive immune systems should be activated (Pejawar-Gaddy S, Finn O. (2008) *Critical Reviews in Oncology Hematology.* 67: 93-102).

Tumor antigens have been divided into two broad categories: shared tumor antigens; and unique tumor antigens. Shared antigens are expressed by many tumors. Unique tumor antigens result from mutations induced through physical or chemical carcinogens; they are therefore expressed only by individual tumors.

In one approach, vaccines contain whole tumor cells, though these vaccines have been less effective in eliciting immune responses in spontaneous cancer models. Defined tumor antigens decrease the risk of autoimmunity but because the immune response is directed to a single epitope, tumors can evade destruction through antigen loss variance. A process called "epitope spreading" or "provoked immunity" may mitigate this weakness, as sometimes an immune response to a single antigen will lead to development of immunity against other antigens on the same tumor. Most of the cancer vaccines in development are addressing specific cancer types and are therapeutic vaccines. Several cancer vaccines are currently in development by companies such as Antigenics Inc. (Oncophage), Geron Corporation (GRN-VAC1), Dendreon Corp (Provenge), BN ImmunoTherapeutics (PROSTVAC), GlobeImmune (Tarmogens), Advaxis, Inc (Lovaxin C), Accentia Biopharmaceuticals majority owned subsidiary Biovest International [BiovaxID], GeneMax Corp (GMXX), (Apthera, Inc. (NeuVax).

Despite the potency and specificity of the immune system, vaccination with tumor antigens generally fails to eradicate cancer in mice and humans (1,2). Currently, the most successful form of immunotherapy is adoptive cell therapy, which includes ex-vivo activation of tumor-infiltrating lymphocytes (TILs) and re-infusion of these cells along with high doses of cytokines. This approach is limited by cytokine toxicity and by the limited range of tumors from which sufficient TILs can be obtained (melanoma) (3).

Bone marrow transplantation has become well established in the treatment of malignant disorders. High-dose chemotherapy with hematopoietic stem cell support is widely used for most hematological malignancies, as well as for some solid tumors. In light of recent developments in blood progenitor cell harvest, in particular, the availability of large numbers of blood stem cells, mobilized by granulocyte colony-stimulating factor and collected by leukapheresis, it is possible to overcome histocompatibility barriers in HLA-mismatched patients. Other recent developments including but not limited to new methods for blood progenitor cells mobilization and ex vivo expansion of progenitor cells and immune cells, the use of umbilical cord blood as an alternative source of stem cells, and other molecular techniques, support an effective treatment of cancer via autologous transplantation of hematopoietic and immune cells.

In one aspect, the present invention provides a method for treating cancer comprising: a) obtaining purified tumor cells; b) vaccinating a donor subject with the purified tumor cells; c) collecting immune cells from the vaccinated donor; and d) transplanting the collected immune cells from the donor into a tumor-bearing recipient following total body irradiation of the recipient. In some embodiments, the method of the present invention combines vaccinating the donor with stimulated tumor cells and transplantation of hematopoietic and immune cells collected from the donor to a tumor-bearing recipient. In some embodiments, the subject method comprises autologous tumor vaccination followed by autologous transplantation of hematopoietic and immune cells, wherein the subject is vaccinated with its own tumor cells, for example, tumor cells stimulated with one or more adjuvants, and then transplanted with its own hematopoietic and immune cells collected after tumor vaccination. The subject typically receives total body irradiation before transplantation of hematopoietic and immune cells.

In one example, the present invention shows that mice that have developed disseminated tumors or bulky primary tumors established for 2 weeks following inoculation with the CT26 colon carcinoma cells can be cured, when treated with a combination of tumor vaccination and hematopoetic cell transplantation (HCT), without ex-vivo T cell activation or use of TILs. Prior attempts at effective treatment by vaccination of mice with unmodified CT26 cells have failed due presumably to the low immunogenicity of this tumor (4). Several strategies have been used to overcome this problem including vaccination with GM-CSF transfected CT26 cells as well as with altered ligands with heteroclitic activity (4-7). In the present invention, by combining vaccination with HCT, a strong immune response to unmodified CT26 tumor cells is induced.

Tumor Cell Purification for Vaccination

In one aspect, the present invention provides a method for treating cancer comprising: a) obtaining purified tumor cells; b) vaccinating a donor subject with the purified tumor cells; c) collecting immune cells from the vaccinated donor; and d) transplanting the collected immune cells from the donor into a tumor-bearing recipient following total body irradiation of the recipient. In another aspect, the present invention provides a method for purifying tumor cells from vaccination comprising: a) obtaining a tumor tissue from a subject; b) making cell suspension of the tumor tissue; c) separating tumor cells from the cell suspension; and d) obtaining purified tumor cells with a purity of at least 30%, 35%, 40%, 45%, 50%, 55%, 60%, 65%, 70%, 75%, 80%, 85%, 90%, 91%, 1%, 93%, 94%, 95%, 2%, 3%, 98%, 99% or more.

In some embodiments, tumor cells are purified by Ficoll gradient. Ficoll is a neutral, highly branched, high-mass, hydrophilic polysaccharide which dissolves readily in aqueous solutions. Ficoll radii range from 2-7 nm. It is prepared by reaction of the polysaccharide with epichlorohydrin. Ficoll is part of Ficoll-Paque which is used in biology laboratories to separate blood to its components (erythrocytes, leukocytes etc.) Ficoll-Paque is normally placed at the bottom of a conical tube, and blood is then slowly layered above Ficoll-Paque. After being centrifuged, the following layers will be visible in the conical tube, from top to bottom: plasma and other constituents, a layer of mono-nuclear cells called buffy coat (PBMC/MNC), Ficoll-Paque, and erythrocytes & granulocytes which should be present in pellet form. This separation allows easy harvest of PBMC's. Note that some red blood cell trapping (presence of erythrocytes & granulocytes) may occur in the PBMC or Ficoll-Paque layer. Major blood clotting may sometimes occur in the PBMC layer. Ethylene diamine tetra-acetate (EDTA) and heparin are commonly used in conjunction with Ficoll-Paque™ to prevent clotting. Ficoll can also be used to separate islets of Langerhans from pancreatic tissue. The separated islets can then be used for transplantation into patients with type 1 diabetes.

Separation of viable from non-viable human tumor cells can be performed by differential flotation on Ficoll-Hypaque specific density solution. In some embodiments, Ficoll-Hypaque is used to separate tumor cells from necrotic tissue. Ficoll gradient or filtration can also be used to separate tumor cells from normal blood cells.

In some embodiments, tumor cells are purified by Percoll. Percoll is a tool for efficient density separation. It is used for the isolation of cells, organelles, and/or viruses by density centrifugation. Percoll consists of colloidal silica particles of 15-30 nm diameter (23% w/w in water) which have been coated with polyvinylpyrrolidone (PVP). Percoll is well suited for density gradient experiments because it possesses a low viscosity compared to alternatives, a low osmolarity and no toxicity towards cells and their constituents.

In some embodiments, tumor cells are purified from other components in the tumor tissue suspension based on their cell surface markers. Tumor markers are substances that can be found in the body when cancer is present. They are most often found in the blood or urine, but they can also be found in tumors and other tissue. They can be products of the cancer cells themselves, or made by the body in response to cancer or other conditions. Most tumor markers are proteins. There are many different tumor markers. Some are seen only in a single type of cancer, while others can be found in many types of cancer. Examples of tumor cell surface markers that can be used to isolate tumor cells include but are not limited to prostate specific membrane antigen (PSMA) on prostate cancer cells, MAGE, GAGE and BAGE in ovarian cancer and melanoma tissues, PLAC1 (PLACenta-specific 1) in human hepatocellular cancer (HCC) tissues, and epithelial tumor antigen (ETA), e.g. MUC1 on breast cancer cells.

The purity of tumor cells purified from the tumor tissue and suspension by the subject methods of the present invention is at least 70%, 75%, 80%, 85%, 86%, 87%, 88%, 89%, 90%, 91%, 1%, 93%, 94%, 95%, 2%, 3%, 98%, 99% or more. The other components that are removed from the tumor cells during the purification process of the present invention may include but are not limited to stromal cells, immunoregulatory cells such as regulatory T cells, myeloid suppressor cells, and immunosuppressive cytokines.

In some embodiments, the purified tumor cells are irradiated prior to vaccination. For example, the tumor cells can be washed and irradiated at 5,000-20,000 rads.

In some embodiments, the purified irradiated tumor cells are stimulated with an adjuvant to increase immunogenecity. An adjuvant is an agent that may stimulate the immune system and increase the response to a vaccine, without having any specific antigenic effect in itself. An immunologic adjuvant is defined as any substance that acts to accelerate, prolong, or enhance antigen-specific immune responses when used in combination with specific vaccine antigens, and thus providing increased immunity to a particular disease. Adjuvants accomplish this task by mimicking specific sets of evolutionarily conserved molecules, so called PAMPs, which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA (Gavin A, et al. (2006) Science 314 (5807): 1936-8). Because immune systems have evolved to recognize these specific antigenic moieties, the presence of an adjuvant in conjunction with the vaccine can greatly increase the innate immune response to the antigen by augmenting the activities of dendritic cells (DCs), lymphocytes, and macrophages by mimicking a natural infection. Furthermore, because adjuvants are attenuated beyond any function of virulence, they pose little or no independent threat to a host organism.

The ability of immune system to recognize molecules that are broadly shared by pathogens is, in part, due to the presence of special Immune receptors called TLRs that are expressed on leukocyte membranes. The binding of ligand—either in the form of adjuvant used in vaccinations or in the form of invasive moieties during times of natural infection—to the TLR marks the key molecular events that ultimately lead to innate immune responses and the development of antigen-specific acquired immunity (Medzhitov R, Preston-Hurlburt P, Janeway C (193) Nature 388 (6640): 394-7). Examples of adjuvant that can be used in the subject methods of the present invention include but are not limited to CpG, LPS, polyIC, imiquimod, and GM-CSF. Stimulation of tumor cells in the presence of an adjuvant is well known to one skilled in the art.

Storing the Purified Tumor Cells

It may be advantageous to store purified tumor cells prior to, during, or after use of the cells for vaccination. For example, the purified tumor cells can be stored upon acquisition to facilitate transport, or to wait for the results of other analyses. In another embodiment, purified tumor cells are provided to physicians for appropriate treatment of cancer. In another embodiment, purified tumor cells are stored while awaiting instructions from a physician or other medical professional. In some cases, a portion of the purified tumor cells are stored while another portion of the purified tumor cells is further manipulated. Such manipulations can include but are not limited to molecular profiling, cytological staining, gene or gene expression product extraction, fixation, and examination.

The purified tumor cells may be placed in a suitable medium, excipient, solution, or container for short term or long term storage. Said storage may require keeping the cells in a refrigerated, or frozen environment. The tumor cells may be quickly frozen prior to storage in a frozen environment. The frozen sample may be contacted with a suitable cryopreservation medium or compound including but not limited to: glycerol, ethylene glycol, sucrose, or glucose. A suitable medium, excipient, or solution may include but is not limited to: hanks salt solution, saline, cellular growth medium, or water. The medium, excipient, or solution may or may not be sterile.

The medium, excipient, or solution may contain preservative agents to maintain the sample in an adequate state for subsequent diagnostics or manipulation, or to prevent coagulation. Said preservatives may include citrate, ethylene diamine tetraacetic acid, sodium azide, or thimersol. The sample may be fixed prior to or during storage by any method known to the art such as using glutaraldehyde, formaldehyde, or methanol. The container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile. In some cases, the sample may be stored in a commercial preparation suitable for storage of cells for subsequent cytological analysis such as but not limited to Cytyc ThinPrep, SurePath, or Monoprep.

Business Method

Also provided by the present invention is a business method of providing purified tumor cells of the present invention to a third party. As described herein, the term customer or potential customer refers to individuals or entities that may utilize methods or services of the tumor cell purification business. Potential customers for the tumor cell purification methods and services described herein include for example, patients, subjects, physicians, cytological labs, health care providers, researchers, insurance companies, government entities such as Medicaid, employers, or any other entity interested in achieving more economical or effective system for diagnosing, monitoring and treating cancer.

Such parties can utilize the purified tumor cells obtained from the tumor cell purification method of the present invention, for example, to vaccinate patients having such cancer for treatment.

Tumor Vaccination and Hematopoietic Cell Transplantation (HCT) as Cancer Therapy In some embodiments, the purified irradiated tumor cells are mixed with adjuvant and injected into a subject for vaccination. In some embodiments, the subject is bearing a tumor. In some embodiments, the vaccination is autologous tumor vaccination wherein the tumor cells are injected into the subject from whom the tumor cells were originally obtained. The tumor cells can be obtained from a primary tumor, a disseminated tumor, or a metastatic tumor. In some embodiments, the tumor is a solid tumor. In some embodiments, tumor cells are administered to the subject parenterally, including intramuscular, intraarterial, intrathecal, intradermal, intraperitoneal, intrasplenic, subcutaneous, and intravenous administration. In some embodiments the adjuvant is injected directly into the tumor.

After vaccination with the purified tumor cells of the present invention, peripheral blood immune cells are collected. In some embodiments, the immune cells are T lymphocytes, i.e. T cells.

The immune cells can be collected several weeks after tumor cell vaccination, for example, peripheral blood T cells can be collected 6 weeks after tumor vaccination. In some embodiments, hematopoietic progenitor cells, such as $CD34^+$ cells, are mobilized with granulocyte colony-stimulating factor (G-CSF). G-CSF is a colony-stimulating factor hormone. It is a glycoprotein, growth factor or cytokine produced by a number of different tissues to stimulate the bone marrow to produce granulocytes and stem cells. G-CSF then stimulates the bone marrow to release them into the blood. G-CSF is also a potent inducer of HSCs mobilization from the bone marrow into the bloodstream, although it has been shown that it does not directly affect the hematopoietic progenitors that are mobilized. Therefore, G-CSF is used to increase the number of hematopoietic stem cells in the blood of the donor before collection by leukapheresis for use in hematopoietic stem cell transplantation. It may also be given to the receiver, to compensate for conditioning regimens.

In some embodiments, $CD34^+$ hematopoietic progenitor cells are enriched. CD34 molecule is a cluster of differentiation molecule present on certain cells within the human body. It is a cell surface glycoprotein and functions as a cell-cell adhesion factor. It may also mediate the attachment of stem cells to bone marrow extracellular matrix or directly to stromal cells. Known methods in the art can be used to enrich $CD34^+$ hematopoietic progenitor cells. For example, CD34+ cells may be isolated from blood samples using immunomagnetic or immunofluorescent methods. Antibodies are used to quantify and purify hematopoietic progenitor stem cells for research and for clinical bone marrow transplantation. In one embodiment, iso-osmolar Percoll density gradient is used to enrich CD34+ cells. In another embodiment, an immunomagnetic separation technique using anti-CD34 antibody or magnetic beads coated with anti-CD34 antibody is used to enrich $CD34^+$ cells.

In some embodiments, both $CD34^+$ progenitor cells and peripheral T cells are collected from the vaccinated subject for subsequent transplantation into the tumor-bearing recipient. In some embodiments, such transplantation is autologous wherein the $CD34^+$ progenitor cells and peripheral immune cells are collected from a vaccinated cancer patient and subsequently injected back into the same patient following total body irradiation of the patient. Transplantation is typically performed parenterally, for example, via intravenous infusion.

In some embodiments, the recipient receives a total body irradiation (TBI) prior to receiving hematopoietic and immune cell transplantation. In some embodiments, the patient receives TBI before autologous transplantation. Total body irradiation (TBI) is a form of radiotherapy used primarily as part of the preparative regimen for hematopoietic stem cell (or bone marrow) transplantation. TBI involves irradiation of the entire body, though in modern practice the lungs are often partially shielded to lower the risk of radiation-induced lung injury. Total body irradiation in the setting of bone marrow transplantation serves to destroy or suppress the recipient's immune system, preventing immunologic rejection of donor bone marrow or blood stem cells. Additionally, high doses of total body irradiation can eradicate residual cancer cells in the transplant recipient, increasing the likelihood that the transplant will be successful.

Doses of total body irradiation used in bone marrow transplantation typically range from 10 to >12 Gy. For reference, a dose of 4.5 Gy is fatal in 50% of exposed individuals without aggressive medical care. At these doses, total body irradiation both destroys the patient's bone marrow (allowing donor marrow to engraft) and kills residual cancer cells. Non-myeloablative bone marrow transplantation uses lower doses of total body irradiation, typically about 2 Gy, which do not destroy the host bone marrow but do suppress the host immune system sufficiently to promote donor engraftment.

In some embodiments, total body irradiation is fractionated. That is, the radiation is delivered in multiple small doses rather than one large dose. It has been demonstrated that delivering TBI through multiple smaller doses resulted in lower toxicity and better outcomes than delivering a single, large dose (Thomas E D, Buckner C D, Clift R A, et al. (139) N. Engl. J. Med. 301 (11): 53-9). In other embodiments, TBI is delivered in one single dose.

Following total body irradiation, the recipient typically receives hematopoietic and immune cell transplantation, in a preferred embodiment, autologous transplantation. Hematopoietic stem cell transplantation (HSCT) is the transplantation of blood stem cells derived from the bone marrow or blood. Stem cell transplantation is a medical procedure in the fields of hematology and oncology, most often performed for people with diseases of the blood, bone marrow, or certain types of cancer. With the availability of the stem cell growth factors GM-CSF and G-CSF, most hematopoietic stem cell transplantation procedures are now performed using stem cells collected from the peripheral blood, rather than from the bone marrow.

Autologous HSCT requires the extraction (apheresis) of hematopoietic stem cells (HSC) from the patient and storage of the harvested cells in a freezer. The patient is typically treated with high-dose chemotherapy with or without radiotherapy with the intention of eradicating the patient's malignant cell population at the cost of partial or complete bone marrow ablation (destruction of patient's bone marrow function to grow new blood cells). The patient's own stored stem cells are then returned to his/her body, where they replace destroyed tissue and resume the patient's normal blood cell production. Autologous transplants have the advantage of lower risk of infection during the immune-compromised portion of the treatment since the recovery of immune function is rapid. Also, the incidence of patients experiencing rejection (graft-versus-host disease) is very rare due to the donor and recipient being the same individual. These advantages have established autologous HSCT as one of the standard second-line treatments for such diseases as lymphoma (Canellos, George (193) *The Oncologist* 2 (3): 181-183).

In some embodiments, the subject method further comprises vaccinating the recipient with the purified tumor cells of the present invention after the transplantation. For example, the recipient can be vaccinated with the purified tumor cells one more time after having received the transplantation.

Clinical Efficacy

Tumor growth and disease progression is monitored during and after treatment of cancer via the subject methods of the present invention. Clinical efficacy can be measured by any method known in the art. In some embodiments, clinical efficacy of the subject treatment method is determined by measuring the clinical benefit rate (CBR).

The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+ PR+SD≥6 months. In some embodiments, CBR for the subject treatment method is at least about 50%. In some embodiments, CBR for the subject treatment method is at least about 55%, 60%, 65%, 70%, 75%, 80%, 85%, 90%, 95% or more.

In the present invention, the preclinical data show for the first time that it is possible to eradicate primary, metastatic, or disseminated solid tumors by treating tumor bearing hosts with HCT containing sensitized T cells from vaccinated donors. While there is growing evidence that hematologic cancers can be effectively treated with a combination of tumor vaccination and HCT (15,16), the effect of such treatment on solid tumors has not been tested. Our outcome measure for tumor immunity in the present invention was eradication of the CT26 or MC38 colon tumors.

An important limitation of allogeneic HCT is the development of graft versus host disease (GVHD), which occurs in a severe form in about 30-50% of humans who receive this therapy (19-21). GVHD is likely to be aggravated by vaccinating donors with tumors expressing host alloantigens. By combining tumor vaccination of the donor with syngeneic HCT for the treatment of primary and metastatic colon cancer in mice, not only GVHD is avoided but also a potent and durable anti-tumor response is achieved. The results demonstrate a powerful synergy between tumor vaccination and HCT in two genetically distinct mouse strains with two different colon tumors.

In the subject methods, a robust anti-tumor immune response can be transferred to tumor bearing mice without ex-vivo T cell expansion or treatment of the mice with cytokines. Without being bound by any theory, the finding that $CD4^+$ and $CD8^+$ T cells needed to be included in the transplant to achieve cures indicates that effective vaccination requires epitopes recognized by both types of T cells. Such epitopes were lacking in a vaccine consisting of the immunodominant AH-1 peptide and CpG, which may explain why this vaccine was ineffective, in contrast to vaccines containing whole tumor cells, which are a source of multiple CD4 and CD8 epitopes. $CD4^+$ T cells provide help to memory $CD8^+$ T cells by enhancing their immune potency, expansion, and persistence after exposure to antigen (24).

Without being bound by any theory, the subject methods indicate that irradiation of tumor bearing hosts was also required for tumor cures, and markedly augmented the expansion of transplanted T cells in the spleen and their infiltration into tumors. Since lethal irradiation was considerably more effective than sublethal irradiation, hematopoetic stem cells had to be included in the transplants to rescue hosts from marrow aplasia in the present invention. Previous studies indicate that the hematopoetic stem cells injected into irradiated mice not only prevented marrow aplasia, but also facilitated the expansion of $CD8^+$ T cells directed to melanoma tumor antigens by enhancing IL-7 and IL-15 production (22).

In the present invention, we found that irradiation and HCT altered the balance of T cell subsets infiltrating the tumors rather than simply depleting T regulatory cells at the tumor site. Since $CD4^+CD25^+FoxP3^+$ Treg cells can suppress tumor immunity (14), and $CD8^+$ effector memory T cells can mediate tumor cell killing, the balance of the subsets was determined in tumor bearing mice with or without HCT. Mice given irradiation and HCT had a 10 fold higher ratio of $CD8^+$ effector memeory T cells:Treg cells in the tumors as compared to control mice without HCT. Thus, the HCT procedure not only increases the absolute number of T cells that infiltrated the tumors, but also favors the T cell subsets that kill tumor cells versus the subset that suppresses tumor immunity.

Tumor vaccination without HCT was not effective against established tumors. However, the subject methods demonstrate that vaccination of tumor-bearing animals provided long-term, transferable immunity, which can be enhanced by HCT. These data suggest that patients whose primary tumors are resected but remain at high risk for relapse, can benefit from early vaccination combined with HCT in the event of relapse.

Methods of Treatment: Anti-Cancer Therapy

One aspect of the present invention relates to a method for treating cancer comprising: a) obtaining purified tumor cells; b) vaccinating a donor subject with the purified tumor cells; c) collecting immune cells from the vaccinated donor; and d) transplanting the collected immune cells from the donor into a tumor-bearing recipient following total body irradiation of the recipient. The term "subject" as used herein includes humans as well as other mammals. The term "treating" as used herein includes achieving a therapeutic benefit and/or a prophylactic benefit. By therapeutic benefit is meant eradication or amelioration of the cancer. Also, a therapeutic benefit is achieved with the eradication or amelioration of one or more of the physiological symptoms associated with cancer such that an improvement is observed in the animal subject, notwithstanding the fact that the animal subject may still be afflicted with that cancer.

The types of cancer that can be treated using the subject methods of the present invention include but are not limited to adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squarnous cell or epidermoid carcinoma, bronchial adenoma, choriocarinoma, head and neck cancers, teratocarcinoma, or Waldenstrom's macroglobulinemia.

In a preferred embodiment, the subject method is used to treat a solid tumor, for example, colorectal cancer, lung cancer, liver cancer, breast cancer, prostate cancer, ovarian cancer or pancreatic cancer.

Combination Therapy

In some embodiments, the subject method further comprises administering to a subject in need thereof an anti-tumor agent, or a pharmaceutically acceptable salt or prodrug thereof. In some embodiments, the anti-tumor agents include but are not limited to antitumor alkylating agents, antitumor antimetabolites, antitumor antibiotics, plant-derived antitumor agents, antitumor organoplatinum compounds, antitumor campthotecin derivatives, antitumor tyrosine kinase inhibitors, monoclonal antibodies, interferons, biological response modifiers, and other agents having anti-tumor activities, or a pharmaceutically acceptable salt thereof.

In some embodiments, the subject method further comprises treating a subject in need thereof one or more of the following therapies in combination with the subject method disclosed herein.

Antineoplastic Chemotherapeutic Agents

Suitable antineoplastic anti-tumor agents to be used in the present invention include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Antineoplastic Agents

Natural antineoplastic agents comprise antimitotic agents, antibiotic antineoplastic agents, camptothecin analogues, and enzymes. Antimitotic agents suitable for use herein include, but are not limited to, *vinca* alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 12134, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

Nanotherapy

Nanometer-sized particles have novel optical, electronic, and structural properties that are not available from either individual molecules or bulk solids. When linked with tumor-targeting moieties, such as tumor-specific ligands or monoclonal antibodies, these nanoparticles can be used to target cancer-specific receptors, tumor antigens (biomarkers), and tumor vasculatures with high affinity and precision. The formuation and manufacturing process for cancer nanotherapy is disclosed in U.S. Pat. No. 7,179,484, and article M. N. Khalid, P. Simard, D. Hoarau, A. Dragomir, J. Leroux, Long Circulating Poly(Ethylene Glycol)Decorated Lipid Nanocapsules Deliver Docetaxel to Solid Tumors, *Pharmaceutical Research*, 23(4), 2006, all of which are herein incorporated by reference in their entireties.

RNA Therapy

RNA including but not limited to siRNA, shRNA, microRNA may be used to modulate gene expression and treat cancers. Double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides known in the art all have a common feature in that each strand of the duplex has a distinct nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence.

MicroRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents can be used to prevent initial occurrences of cancer, or to prevent recurrence or metastasis. In some embodiments, treatment of cancer with the subject methods is accompanied with the use of chemopreventative agents. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoic acid, 13-cis-retinoic acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in the present invention is cancer vaccines. These can be created through immunizing a patient with all or part of a cancer cell type that is targeted by the vaccination process.

Side-Effect Limiting Agents

In some embodiments, treatment of cancer with the subject methods is accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

EXAMPLES

The following materials and methods apply to Examples 1-6.

Wild-type male BALB/c ($H-2^d$) mice, male BALB/c $Rag2^{-/-}$ mice, wild-type male DBA2/J ($H-2^d$) mice, and wild-type female C57BL/6 mice were purchased from Jackson Laboratories (Bar Harbor, Me., USA). Mice were 5-8 weeks old. The Stanford University Committee on Animal Welfare (Administration Panel of Laboratory Animal Care) approved all mouse protocols used in this study.

The CT26 cell line (an N-nitro-N-methylurethane-induced BALB/c murine colon carcinoma) was purchased from ATCC (Manassas, Va.). The MC38 cell line (dimethylhydrazine induced C57BL/6 colon adenocarcinoma) was kindly provided by Dr. David Bartlett of the University of Pittsburgh (8). Cell lines were maintained in RPMI-1640 complete medium supplemented with 10% fetal calf serum, L-glutamine, 2 mercaptoethanol, streptomycin and penicillin. For intrasplenic injection, animals were anesthetized with ketamine/xylazine. Laparotomy was performed, and $5 \times 10^5$ CT26 cells were injected in the spleen. Abdominal wall was closed with surgical sutures.

In terms of vaccination, five-week-old male BALB/c mice were immunized by subcutaneous injection of 1×10 irradiated (10,000 cGy) CT26 cells and 30 μg of CpG. Five-week-old female C57BL/6 mice were immunized by subcutaneous injection of 1×10 irradiated (10,000 cGy) MC38 cells and 30 μg of CpG. AH-1 peptide (300 μg per vaccination) used in this study was obtained from Sigma-Genosys. The peptide was >95% pure as indicated by analytical HPLC. Lyophilized peptide was diluted in DMSO and stored at −20° C. until use. Oligonucleotide containing unmethylated CG motifs (CpG) (TCCATGACGTTCCTGACGTT (SEQ ID NO: 1)) was synthesized and phosphorothioate-stabilized by Oligos, Etc. The oligonucleotide was reconstituted in sterile pyrogen-free water and then diluted in PBS for in vivo injections. 30 μg of ultrapure LPS (Invivogen) was used in some experiments instead of CpG.

Irradiation was performed with a Philips X-ray unit (200 kV, 10 mA; Philips Electronic Instruments Inc., Rahway, N.J., USA) at a rate of 84 cGy/min with a 0.5 mm Cu filter.

For donor cell preparation, single cell suspensions of bone marrow and spleen prepared according to previously described procedures (9). Some samples were enriched either for CD4+ cells, CD8+ T cells or Thy1.2+ cells with anti-CD4, anti-CD8 magnetic microbeads (Miltenyi Biotech) or anti-Thy1.2-biotin monoclonal antibodies (mAb) (5a-8; Caltag, Burlingame, Calif.) and streptavidin-magnetic beads (Miltenyi Biotech) respectively using the MidiMACS system (Miltenyi Biotech, Auburn, Calif.). Enriched cells were stained with anti-TCR-allophycocyanin (APC) and anti-CD4 or anti-CD8-fluorescein isothiocyanate (FITC) mAbs to check for purity, and preparations were uniformly at least 95% pure.

Purified HSCs were obtained by modification of the methods described by Spangrude et all (10). Thy-1lolin-/loSca-1+ c-Kit+ cells were sorted on a dual laser FACS (Becton Dickinson, Mountain View, Calif.) made available through the FACS shared-user group at Stanford University using FlowJo software (TreeStar, Ashland, Oreg.) for data analysis. After sorting cells were checked by FACS reanalysis and determined to be >99% pure.

For histopathologic analysis, animals were killed when moribund as per Stanford Animal Welfare protocol guidelines, or at 100 days after transplantation if they survived without morbidity. Histopathological specimens were obtained from lungs and livers of hosts. Tissues were fixed in 10% formalin, stained with hematoxylin and eosin and images were obtained using an Eclipse E1000M microscope (Nikon, Melville, N.Y., USA) as described before (11).

For analysis of donor cell accumulation in host spleens and tumor nodules, single-cell suspensions were prepared from spleens and tumor nodules of BALB/c recipients. The following reagents were used for flow cytometric analysis: unconjugated anti-CD16/32 (2.4G2 BD Biosciences), anti-CD4-FITC (RM4-5 BD Biosciences), anti-TCR-APC (H57-53 BD Biosciences), anti-CD8-APC-Cy7, (53-6.7 BD Biosciences), anti-Thy1.1 PE-Cy7 (HIS51, eBioscience), anti-Thy1.2-biotin (5a-8; Caltag) mAbs, and streptavidin-PE (SAv-phycoerythin, BecktonDickenson). All stainings were performed in PBS/1% calf serum in the presence of purified anti-CD16/32 mAbs.

For statistical analysis, Kaplan-Meier survival curves were generated using Prism software (SAS Institute Inc., Cary, N.C., USA), and statistical differences were analyzed using the log-rank (Mantel-Cox) test. Statistical significance in differences between mean percentage of donor cells in host spleens and tumors was analyzed using the two-tailed Student's t-test of means. For all tests, P<0.05 was considered significant.

Example 1

Hematopoietic Cell Transplantation (HCT) from Vaccinated BALB/c Donor Mice Cures Established CT26 Colon Tumors FIG. 1A shows the experimental scheme, which uses HCT from tumor-vaccinated donors to treat CT26 colon tumors in syngeneic mice. In all instances, normal BALB/c donor mice were vaccinated subcutaneously (s.c.) with 10 irradiated CT26 tumor cells mixed with 30 µg CpG, an adjuvant that stimulates antigen presenting cell via TLR-9 (12,13). After 90 days, spleen and bone marrow cells were harvested, and transplanted intravenously (i.v.) into tumor-bearing BALB/c host mice following a single dose of total body irradiation (TBI). Seven days prior to TBI, hosts had been given live tumor cells via s.c. ($2.5 \times 10^4$), i.v. ($2 \times 10^5$) or intrasplenic ($5 \times 10^5$) routes. FIG. 1B shows the progressive growth of s.c. tumors in all untreated mice. Similarly, tumor bearing recipients of $50 \times 10$ bone marrow cells and $60 \times 10$ spleen cells from unvaccinated donors had uniformly progressive tumors (FIG. 1C). In contrast, after HCT from vaccinated donors, tumor bearing mice displayed a steady regression of tumor volume over a 100 day observation period (FIG. 1D), which remained stable until the end of study (day 180; data not shown). Shortening the time interval between immunization of the donor and harvesting the graft from 90 to 14 days, but not to 50 days, resulted in lower anti-tumor effect (p=0.005 and p=0.3, respectively; log rank test; FIG. 1E). Omission of CpG from the donor vaccine resulted in a further loss of efficacy (p=0.01), and only 20% of hosts survived 100 days.

The same HCT strategy was also successful in recipients given tumor cells by i.v. administration. By day 7, tumor cells had disseminated into the lungs and formed multiple tumor clusters (FIG. 1H). By day 20 all untreated control mice succumbed to progressive disease with large, nearly confluent tumor nodules (FIGS. 1F and 1H). In contrast, recipients of HCT from vaccinated donors all survived at least 100 days, with no histologic evidence of residual tumor (FIG. 1H). Accordingly, improvement of survival was significant as compared to untreated mice (p<0.01) (FIG. 1F). When tumor cells were injected into the spleen, by day 7 tumor nodules became established in the parenchyma of the liver (FIG. 1I), and by day 14 there was evidence of blood vessel invasion (arrows, FIG. 1I). All untreated animals died by day 30 (FIG. 1G) with multiple visible, as well as microscopic, tumors. Treated mice survived beyond day 100 (FIG. 1G), easily exceeding the survival of untreated mice (p=0.001). The liver of treated mice displayed no abnormalities and also no histologic evidence of residual tumor at day 60 (FIG. 1I). HCT from vaccinated donors also cured peritoneal carcinomatosis, which had been created by intraperitoneal injection of $5 \times 10$ tumor cells and which displayed multiple peritoneal nodules and ascites by the time of transplant (data not shown). All untreated mice died by day 20, and all transplanted mice survived at least 100 days without any peritoneal tumor growth.

Example 2

Vaccination and HCT Induces Long-Term Anti-Tumor Immunity

To assess the duration of effect of vaccination combined with HCT, "cured" animals from the experiment in FIG. 1D were challenged with $2.5 \times 10^4$ live tumor cells at day 24 as shown in the experimental scheme in FIG. 2A. The results show that these animals were completely protected and survived for at least 100 days (FIG. 2A). Moreover, harvesting of spleen and bone marrow cells from "cured" recipients at day 180 after HCT, and secondary transfer resulted in 80% of the new recipients surviving for more than 100 days (FIG. 2B). At least 100 days later those secondary recipients were used as donors for another HCT into irradiated tumor-bearing tertiary hosts which was also effective since all tertiary hosts survived more than 100 days (FIG. 2B). Thus, anti-tumor immunity generated by a single vaccination could eradicate tumors 370 days later (FIG. 2B).

Example 3

Tumor Eradication Requires Lethal Irradiation of Hosts, as Well as Transfer of CD4$^+$ and CD8$^+$ T Cells from Vaccinated Donors FIG. 3A illustrates the significant role of the host conditioning regimen in our vaccine strategy. All tumor bearing recipients of bone marrow and splenocytes from vaccinated donors were cured when conditioned with myeloablative TBI (800 cGy). In contrast, only 60% of hosts survived 100 days with a non-myeloablative radiation dose (450 cGy) (p<0.05), while none survived more than 40 days without irradiation (p<0.0001). Radiation causes lymphodepletion which might deplete host regulatory T cells that suppress anti-tumor immune responses. In order to test whether radiation mediates tumor eradication through such a mechanism, we studied unirradiated tumor-bearing RAG2$^{-/-}$ recipients that lack T cells. Rag 2$^{-/-}$ BALB/c hosts were given myeloablative radiation or no radiation immediately before transplantation of cells from vaccinated donors. FIG. 3B shows that although there was a significant delay in mortality in non-irradiated Rag 2–/– mice as compared to non-irradiated wild type mice (p=0.001), all mice died by day 65. Conditioning of the Rag 2$^{-/-}$ mice with 800 cGy resulted in significant improvement in survival as compared to the non-irradiated mice (p=0.001), and all hosts survived at least 100 days (FIG. 3B).

When IFNγ$^{-/-}$ BALB/c mice were vaccinated and used as bone marrow and splenocyte donors, the survival of hosts was decreased as compared to wild type syngeneic donors (p=0.004) (FIG. 2C). Likewise, survival was reduced in all five mice given grafts from vaccinated MHC-matched, minor antigen-mismatched DBA/2J donors (H-2$^d$) (p<0.001) (FIG. 3C). While 4/5 animals had progressive tumor growth, one mouse displayed tumor regression, but succumbed due to GVHD. Substitution of whole tumor cells with the tumor-associated immunodominant AH-1 peptide (4) for vaccination of donors resulted in decreased survival (p<0.0001) (FIG. 3C). Use of lipopolysaccharide (30 μg) as an adjuvant for vaccination was just as effective as CpG, based on survival of hosts post-HCT (p=1.0) (FIG. 3C). Grafts from vaccinated donors consisting of bone marrow or FACS-purified c-kit$^+$Sca1$^{high}$lin$^-$ hematopoietic stem cells (HSC) failed to prevent tumor progression (FIG. 3D). Addition of 5×10 splenic T cells to the HSCs increased survival (p=0.008) such that the majority of hosts were alive at 100 days without detectable tumors (FIG. 3D). When HSC grafts were supplemented with both CD4$^+$ (3.5×10) plus CD8$^+$ T cells (1.8×10), survival was improved (p<0.008) as compared to supplementation with CD4$^+$ or CD8$^+$ T cells only (FIG. 3E).

The utility of HCT from vaccinated donors was further validated in studies of another colon cancer, MC38, which grows only in C57BL/6 (H-2$^b$) mice (8). For these experiments, donor mice were vaccinated with 1×10 MC38 tumor cells (FIG. 3F). Again, while syngeneic recipients of grafts from vaccinated donors were cured, recipients of transplants from unvaccinated donors did not survive beyond 35 days (p<0.0001). HCT from tumor-vaccinated donors could also significantly improve survival of animals with large (>10 mm) tumors established for 15 days (p=0.0005) (FIG. 3G). After 100 days, 60% of treated animals were completely tumor free.

Example 4

Analysis of Donor T Cells in Host Tumors and Spleens after Transplantation: Irradiation Promotes T Cell Accumulation in Tumors To delineate the donor-derived cell populations involved in the anti-tumor response, bone marrow and spleen cells were transplanted from BALB/c Thy1.1 donors into tumor bearing BALB/c Thy 1.2 hosts, as depicted in FIG. 4A. To assure that there would be sufficient donor cells for analysis at day 28, HCT was performed in animals bearing tumors that had been established for 14 instead of 7 days. In irradiated recipients of vaccinated donor grafts approximately 70% of T cells infiltrating the tumors were of donor origin (FIGS. 4B and 4C), while donor T cells accounted for <2% of tumoral T cells when hosts were not irradiated (p<0.001). A similar facilitation of donor cell accumulation in the spleen was observed in irradiated versus non-irradiated hosts (p<0.01) (FIGS. 4B and 4C). Differences in accumulation of total T cells from vaccinated and unvaccinated donors were not significant (p>0.05). However, the majority of tumor T cells from vaccinated donors were CD8$^+$, whereas most of the tumoral T cells from unvaccinated donors were CD4$^+$ (p=0.01) (FIGS. 4D and 4E). CD4$^+$ T cells were in the majority in the spleens with both vaccinated and unvaccinated donors (p<0.001).

Example 5

HCT Alters the Balance Between Regulatory and Effector Cells at the Tumor Site

Previous studies have shown that CD4$^+$CD25$^+$FoxP3$^+$ Treg cells can suppress tumor immunity (14). Moreover, this suppression was mediated at the tumor site and was lost after intra-tumoral depletion of Tregs (14). It is shown above (FIG. 3 B) that conditioning and HCT was required to cure tumors in RAG2$^{-/-}$ mice lacking T regulatory cells. Thus, the requirement for irradiation is not based on host Treg depletion.

However, regulatory T cells of donor or host origin may be capable of infiltrating tumors when wild-type hosts are used. Host and donor T cell subsets infiltrating CT26 subcutaneous tumor nodules were examined in wild-type BALB/c mice before and after HCT, and in controls without HCT as shown in the experimental scheme in FIG. 5A. Control Thy1.2 mice given CT26 cells subcutaneously were euthanized 14 or 28 days later, and single cell suspensions from tumors were analyzed for tumor infiltrating T lymphocytes (TIL) subsets.

Experimental mice were lethally irradiated and given HCT from vaccinated Thy 1.1 donors after 14 days of tumor growth, and tumor cell suspension were analyzed 14 days after HCT. FIG. 5B shows the representative staining patterns for CD4$^+$ and CD8$^+$ T cells in cell suspensions using gated Thy1.2$^+$ T cells from control mice and gated Thy1.1$^+$ from mice given HCT at 28 days after the subcutaneous injection of tumor cells (14 days after HCT).

Whereas CD8$^+$ and CD4$^+$ cells accounted for about 90% and 5% respectively of Thy1.1$^k$ cells in mice given HCT, the CD8$^+$ and CD4$^+$ cells accounted for 30% and 28% respectively of Thy1.2$^+$ cells in mice without HCT. Almost all of the CD8$^+$ and CD4$^+$ T cells in mice given HCT were CD62L$^{lo}$ (FIG. 5B). The staining pattern indicates that few naïve or central memory cells were found in these tumors, almost all were effector memory cells, since the CD8$^+$ and CD4$^+$ cells were almost all CD44$^{hi}$.

In contrast, the gated CD8$^+$ and CD4$^+$ cells from tumors in control mice contained discrete subsets of both CD62 L$^{low}$ and CD62 L$^{hi}$ cells. The CD62 L$^{hi}$ cells accounted for 26% of CD8$^+$ cells and 58% of CD4$^+$ cells (FIG. 5B). Staining of gated CD4$^+$ tumor cells from control mice and those given HCT for CD4 versus CD25 showed that about 16% of CD4$^+$ cells were CD25$^+$ in controls, and 32% were CD25$^+$ in those given HCT at the day 28 time point (FIG. 5C). At day 14, 22% of CD4$^+$ cells were CD25$^+$. The results of additional staining for intracellular FoxP3$^+$ showed that the mean percentage of CD4$^+$CD25$^+$FoxP3$^+$ Treg cells among gated CD4+ cells in the tumors of all 3 groups of mice varied from about 15% to 25% (FIG. 5D).

The differences in the means were not statistically significant (p>0.05) as judged by the Student t test. Despite the similar percentages of Treg cells among total CD4+ T cells in the tumor cell infiltrate, there was a marked difference in the balance of $CD8^+CD62 L^{lo}CD44^{hi}$ effector memory T cells versus Treg cells. Whereas, day 28 tumors from control mice showed a mean ratio of about 5:1 CD8+ effector memory to Treg cells in the infiltrate, the day 28 tumors from mice given HCT showed mean ratio of about 50:1. The differences in ratios were statistically significant (p<0.05). Thus, while HCT did not deplete Tregs at the tumor site, the balance of tumor infiltrating cells was altered to favor CD8+ effector memory T cells as compared to Treg cells.

Example 6

Tumor Vaccination Becomes Effective when Combined with HCT and Vaccine Induced Anti-Tumor Immunity is not Prevented by the Presence of Growing Tumors FIG. 6A shows the experimental scheme used to determine the effect of vaccination alone on survival of tumor-bearing mice. FIG. 6B shows that the survival of vaccinated, but not HCT treated, animals with 7-day tumors did not improve as compared to unvaccinated tumor-bearing animals and all animals died by day 40. Moreover, when vaccinated non tumor-bearing animals were challenged with as few as $2.5 \times 10^4$ CT26 cells 16 and 50 days after vaccination (FIG. 6C), only 20% of mice survived 100 days (FIG. 6D). Some degree of protection developed in animals vaccinated given the tumor challenge 90 days after vaccination, as indicated by the observation that 50% of animals remained tumor free (p=0.03)(FIG. 6D). Next, to assess the potential effect of larger tumors on the response to vaccination, we vaccinated mice with tumors growing for 7 days and then waited 14 additional days before resecting the growing tumors at day 21 (FIG. 6E). Bone marrow and splenocytes were harvested from donors on day 110 and transferred into lethally irradiated tumor-bearing hosts. All hosts survived with complete tumor regression for at least 100 days (FIG. 6F). Only 20% of hosts given transplants from unvaccinated donors survived 100 days, and the difference using vaccinated versus unvaccinated donors was significant (p<0.05) (FIG. 6F). Thus, HCT from vaccinated animals into syngeneic tumor bearing hosts resulted in cure of tumors, indicating that growing tumors in donors do not prevent the development of potent anti-tumor effector cells in adoptive hosts.

Example 7

Autologous HCT Enhances Tumor Immunity after Vaccination

A model of autolous HCT was studied as shown in FIG. 6G. In this scheme a group of donors was vaccinated 7 days after live tumor cell injection, splenectomized 7 days later, conditioned with TBI immediately after recovery from surgery, and spleen cells were injected intravenously within 6 hours after TBI. Bone marrow cells were not required for rescue of these myeloablated hosts, since mouse spleen cells contain both immune cells and HSCs. Donors that received the autologous transplants had significantly improved survival as compared to those without transplants, and about 40% survived at least 100 days with complete tumor regression (p<0.001) (FIG. 6H). Thus, large 14 day tumors were either cured or their growth significantly delayed after autologous HCT.

Example 8

Clinical Study to Assess the Safety and Feasibility of Autologous Tumor Cell-TLR9 Agonist Vaccination Prior to Autologous Hematopoietic and Immune Cell Rescue in Metastatic Colorectal Cancer Objectives
Primary Objectives
To assess the feasibility of using an autologous tumor cell vaccine in combination with standard chemotherapy followed by investigational autologous hematopoietic and immune cell rescue in terms of acceptable clinical toxicity.
Secondary Objectives
To assess the clinical and immunologic efficacy of this vaccine and autologous transplant regimen by measuring the following:
Ex vivo assessment of immune response
Response
Time to progression (TTP)

BACKGROUND

As the third most common cancer in incidence and second in mortality, colorectal cancer (CRC) significantly impacts the lives of many Americans (25). In 2008, it is estimated that 148,810 cases will be diagnosed and 49,20 patients will die from this disease. Approximately 20% of patients present with metastatic disease at diagnosis. The introduction of more effective chemotherapy regimens and biologically targeted agents over the last few years has led to considerable improvement in treatment options for metastatic CRC yet median survival approximates only 2 years. Resection of the primary tumor when clinically indicated followed by combinations of oxaliplatin or irinotecan with intravenous or oral 5-FU, leucovorin, and bevacizumab for first-line therapy of metastatic CRC is standard of care.

In 2004, Goldberg and colleagues established FOLFOX4 as the standard of care chemotherapy regimen in metastatic CRC when they demonstrated its superiority over two older regimens, IFL (bolus 5-FU/leucovorin/irinotecan) and IROX (irinotecan/oxaliplatin), in terms of prolonging median overall survival (OS), progression-free survival (PFS), and increased response (26). FOLFOX4 increased median survival time to 19.5 months compared to 15 months and 17.4 months for IFL and IROX respectively (p=0.0001; HR 0.66, 95% CI 0.54-0.82). Time to progression was also significantly increased to 8.7 months compared to 6.9 and 6.5 months (p=0.0014). Furthermore FOLFOX-4 effected a 45% overall response rate compared to 31% (p=0.002) and 35% (p=0.03) for IFL and IROX respectively. It also induced significantly less associated grade ≥3 nausea, vomiting, diarrhea, febrile neutropenia, and dehydration than the other two regimens.

Hoping to improve this regimen further, capecitabine, an oral pro-drug of 5-FU, was introduced. It has significant advantages over infusional 5-FU including ease of administration with its oral formulation, lack of infusion-related toxicities, and decreased duration of hospitalization and clinic time. Multiple trials have pitted capecitabine-based therapies against infusional 5-FU regimens and have shown comparable efficacy (27-32). Overall toxicity profiles are also comparable between the two regimens with the exception of less myelosuppression and more hand-foot syndrome with capecitabine compared to the infusional-5-FU-based regimens. Thus, in clinical practice, CAPDX (capecitabine-oxaliplatin) is largely considered to be a comparable regimen to FOLFOX, with significantly more convenient administration.

The addition of targeted therapies that inhibit vascular endothelial growth factor (VEGF) and endothelial growth factor receptor (EGFR) to the 5-FU/LV regimens have further increased survival. Bevacizumab, a monoclonal antibody against VEGF, was approved for metastatic CRC in 2004 after the pivotal phase III trial, AVF2107g, showed a significant improvement in OS from 15.6 months to 20.3 months (HR for death, 0.66, p<0.001) with the addition of bevacizumab to IFL (33). PFS and response were also significantly increased from 6.2 months to 10.6 months (p<0.001) and 34.8% to 44.8% (p=0.004) respectively. The first phase III trial to evaluate the combination of bevacizumab with oxaliplatin-based chemotherapy (FOLFOX-4 or CAPDX), NO1626, demonstrated that the addition of bevacizumab improved PFS by 1.4 months (9.4 vs. 8.0 months, HR 0.83, p=0.0023) but overall response rates were similar (34). Median OS also increased from 19.9 months in the placebo group to 21.3 months in the bevacizumab arm but was not statistically significant (HR 0.89, p=0.077).

Cetuximab, a mouse/human chimeric monoclonal antibody to EGFR, has also shown promise in metastatic CRC (35, 36). The BOND trial, a multicenter randomized phase II trial showed a significant doubling of response rate and a 2.6 month increase in PFS with the combination of irinotecan-cetuximab over cetuximab alone in the second line setting, but no difference in median OS (35). These results led the FDA to approve cetuximab in February 2004 for second-line treatment either as a monotherapy in those who cannot tolerate irinotecan or in combination with irinotecan in those who do not have a response to irinotecan alone. The CRYSTAL trial, a phase III multicenter randomized trial also demonstrated that cetuximab holds promise in the first line setting (37). In this trial (n=1217), the addition of cetuximab to FOLFIRI significantly increased response rate by 6% (46.9% vs. 38.7%, p=0.005) and PFS by 1.9 months (p=0.036). Trials evaluating the first line use of cetuximab with oxaliplatin-based regimens appear promising and are ongoing (38, 39).

When using cetuximab, the presence of K-RAS mutations must be considered. Activating mutations in the K-RAS gene are present in 40-45% of colorectal cancer patients (40). The presence of these mutations correlates with a worse outcome and a lack of response to cetuximab in patients with advanced chemotherapy-refractory CRC (41, 42).

Even with these new agents and improved combinations, median survival for metastatic CRC patients remains less than 2 years with less than 5% surviving to 5 years (43). Furthermore, one can expect 20% of patients to progress within 4-6 months (34). Better regimens and treatments are greatly needed to impact this pervasive and fatal disease.

Preclinical Data:

As shown in Examples 1-7, HCT from in vivo-immunized syngeneic donors can cure solid tumors in mice, most likely due to peripheral memory T cell response against the tumor antigen. Specific timing and priming conditions are critical, while the effect appears to be independent from allo-immune reactivity. By combining this vaccine system with autologous hematopoietic cell transplantation, complete response was achieved in 60-100% of mice. The response percentage depended on tumor burden.

Rationale

In summary, preclinical data demonstrate that HCT from in vivo-immunized syngeneic donors can cure solid tumors, most likely due to peripheral memory T cell response against the tumor antigen. Specific timing and priming conditions are critical, while the effect appears to be independent from allo-immune reactivity. By combining this vaccine system with autologous hematopoietic cell transplantation, complete response was achieved in 60-100%. The response percentage depended on tumor burden and sufficient time for priming. Given these data and results from the discovery and the present invention, it is expected that the preclinical studies discovery can be translated to humans with metastatic CRC using the patients own tumor cells, processing the tumor cells to increase antigenicity, and by combining this vaccine and autologous hematopoietic and immune cell rescue with standard of care resection and, when needed, chemotherapy.

The preclinical data suggest that by selecting appropriate patients (e.g., those with a reasonable amount of tumor burden) and providing sufficient time for immunologic response, one can have effective treatment and potentially a cure in metastatic colon cancer patients using immunotherapy in conjunction with standard chemotherapy. This translational endeavor may significantly impact the prognosis of metastatic colon cancer patients, who currently face a median overall survival of about 2 years from diagnosis.

Tumor Processing

Based on prior reports and the pre-clinicial data of resected tumor specimens prepared as cell suspensions, approximately 1 cc of resected tumor yields $1 \times 10^7$ viable tumor cells (49, 51-58). Sufficient tumor will be collected to allow recovery of $\geq 5 \times 10^7$ viable cells after cryopreservation and thawing. Vaccines are prepared and formulated as described in section 4.1.5 using validated methodologies.

CpG

The term CpG denotes regions of DNA where a cytosine nucleotide exists next to a guanine nucleotide. A phosphate (p) separates the two nucleotides. Unmethylated CpG dinucleotides occur more frequently in bacteria and viral genomes than those of vertebrates. The human immune system has evolved to detect these immunostimulatory motifs as a marker of infection. Krieg and colleagues first identified that bacterial DNA and synthetic oligodeoxynucleotides (ODNs) containing unmethylated CpG dinucleotides induced murine B cells to proliferate and secrete immunoglobulins in vitro and in vivo (59).

The immune system utilizes germline-encoded receptors to detect infection via recognition of conserved molecular patterns associated with microbial pathogens (60). One class of these receptors is the Toll-like receptors (TLRs). Bacterial CpG DNA is the natural ligand for TLR-9. Today, synthetic CpG ODN's are an established method to study innate immunity. When TLR-9 recognizes this immunostimulatory DNA containing unmethylated CpG motifs, innate immune responses are activated that subsequently amplify the adaptive-immune response (61). Furthermore, when given in the presence of an antigen, CpG ODNs can trigger predominantly Th-1 type immune responses (60). Th 1 immune activation is desired as it involves activation of NK cells and cytotoxic T lymphocytes (CTLs) that can kill tumor cells, much like they lyse cells infected by viruses and bacteria (62). Numerous animal models have demonstrated that synthetic CpG is an effective adjuvant that enhances both humoral and cellular immune responses in diverse indications, ranging from infectious disease to cancer and allergy, and to date, clinical testing has largely affirmed the potency and safety of ISS-adjuvanted vaccines (61).

Its therapeutic potential in human studies is further advanced by its ease of synthesis, relatively inexpensiveness, and minimal toxicity (63). To date, CpG has been studied as an adjuvant to treatment in a variety of human cancers including lymphoma and non-small cell lung cancer. Various lymphoma and viral vaccine studies incorporating CpG as an adjuvant including doses of 6 mg and greater have shown minimal toxicity (61, 64-67).

Correlative Studies Background

Interleukin-7 (IL-7) & Interleukin-15 (IL-15)

IL-7, a cytokine produced by the bone marrow and thymic stroma, is a non-redundant cytokine essential for thymopoiesis as well as T cell survival, proliferation, and cytotoxic function in the peripheral circulation (76). Expanding on IL-7's known function of inducing proliferation of B cell progenitors in vitro and in vivo, Bolotin and colleagues also demonstrated that administration of IL-7 significantly enhanced immune recovery after T cell-depleted bone marrow transplantation (BMT) in a murine model (77). In another study, the same group explored the relationship between IL-7 and lymphocyte recovery after BMT (78). Lymphopenic patients with severe combined immune deficiency (SCID) or acute lymphoblastic leukemia (ALL) and control patients less than 1 year old had higher serum levels of IL-7 by ELISA. Levels rose in response to further lymphopenia in post-transplant period. These findings underscore IL-7 as a likely regulator of de novo production of T lymphocytes after BMT. The authors assert the increased IL-7 levels observed in the lymphopenic patients were due to altered consumption as these patients likely have decreased numbers of IL-7 receptor (R)-bearing cells with resultant abnormal clearance of IL-7 as opposed to direct upregulation of IL-7 production in response to lymphopenia. They further propose that the binding of the IL-7R is a homeostatic mechanism that regulates circulating levels of IL-7. Further investigation into regulation of IL-7 is needed. It is unclear if IL-7 gene expression by stromal cells is up-regulated by any external stimuli, but it may be negatively regulated by TGF-β, IL-1, and IFN-γ (78, 79). The degree of IL-7 production and resultant serum levels are also likely a function of the age-dependent decline in thymic function (78, 80).

IL-15 is an important cytokine in the proliferation and survival of naïve, effector, and memory T cells. While enhancing the homeostatic proliferation of naïve T cells that require IL-7 and TCR interaction, crucial components of its receptor are not expressed until after naïve T cells begin homeostatic proliferation in response to IL-7 (81). In addition to promoting the maturation and survival of naïve cells, a considerable body of work suggests that IL-15's primary role is regulation of the CD8+ T cell compartment as it induces proliferation of memory cells with cytolytic function (81, 82).

Cytokines that signal through receptors containing the common γ-chain (γc) such as 11-7 and IL-15 are crucial for T-cell development, survival, expansion, and activation (81). Furthermore, IL-7 and IL-15 are vital to the homeostatic response to T cell depletion in the setting of hematopoietic cell transplantation (76, 78). IL-7 appears to be more essential for survival of memory T cells while IL-15 promotes proliferation of those same cells (82). In order to assess IL-7- and IL-15-associated homeostatic expansion of T cells, serum levels of these cytokines will be measured at serial times before and after hematopoietic and immune cell rescue.

Proliferation Assays

The combination of plasma assays for IL-7 and IL-15 with proliferation assays such as Ki67-labeling in T lymphocytes and TCR rearrangement excision circles (TREC) analysis will be utilized to assess T cell expansion.

Ki-67

Ki-67 is a well established intracellular method for detection of T cell proliferation in peripheral blood and will be performed serially before and after hematopoietic and immune cell rescue (82, 83).

TCR Rearrangement Excision Circles

During thymocyte development, rearrangement of the T-cell-receptor (TCR) gene results in excision of circular DNA fragments from genomic DNA (84). Douek and colleagues developed an assay that estimates thymic output more accurately by measuring the numbers of these TREC (85). TRECs are unique to T cells and diluted out with each cellular division, making them useful markers of developmental proximity to the thymus, and thus, their concentrations in peripheral blood can be used to estimate thymic output (85, 86). This technique compares favorably to older techniques that used T cell surface molecules as markers for recent thymic emigration and likely underestimated thymic activity.

Two distinct mechanisms repopulate the total T cell pool after hematopoietic cell transplantation (86). An early rise especially in CD8+ cells after engraftment is mediated by the rapid expansion of limited subsets of pre-existing mature T cells. This occurs in the first 100 days and then declines. Conversely, the numbers of TREC which measure the production of new naïve T cells from hematopoietic stem cells or more committed progenitor cells continue to increase steadily until 1 year post-transplant. Doeuk and colleagues' data strongly suggest that it is residual thymic tissue that is the most likely source for the new TREC-positive naïve T cells that reconstitute the immune system after transplantation (86). Thus, the measurement of numbers of TREC in peripheral blood may serve as a clinical indicator of the potential for recovery of damaged immune system (86) and the technique will be utilized in this study to quantify the proliferation of new lymphocytes.

In Vitro Response to Recall Antigens

In vitro immune responses to recall antigens tetanus toxoid, herpes simplex virus, varicella virus, and cytomegalovirus will be performed (86) before and after vaccination as well as pre- and post-rescue.

Cell-Mediated Lympholysis (CML)

In most preclinical models of hematopoietic cell transplantation, eradication of tumor is mediated by CD8+ T cells using a direct cytolytic pathway. Using a standard CIVIL assay, CD8+ and CD4+ cytolytic function will be measured using the patient's purified blood T cells pre- and post-rescue.

Preclinical and early clinical work has shown that cytotoxic T lymphocytes (CTLs) generated against autologous tumor induce substantial anti-tumor activity. In the current clinical protocol, anti-tumor immune responses will be tested serially in vitro before and after vaccination and pre- and post-rescue. Purified total T cells or purified CD4+ and purified CD8+ T cells (and their memory subsets) will be used as responder cells ($50 \times 10^3$/well). Stimulator cells will be irradiated (5,000 cGy in vitro) single cell suspensions of tumor cells ($50 \times 10^3$) or purified dendritic cells (86) pulsed with the tumor cell lysate obtained by sonication and freeze/thaw. Measurements of responses will include proliferation ($^3$H-thymidine incorporation) and production of the cytokines IL-2, IFN-γ, TNF-α, and IL-10 assayed by intracellular staining or in triplicate culture well supernatants by ELISA (86).

Autoimmunity Panel

A wide range of autoimmune reactions have been seen with immunomodulatory agents such as IFN-α, IL-2, and anti-cytotoxic T-lymphocyte antigen 4 (CTLA-4) including thyroiditis, inflammatory bowel disease and enteritis, hepatitis, vitiligo, dermatitis, arthritis, vasculitis, hypophysitis, panhypopituitarism, and anti-phospholipid syndrome (87-90). In turn, these autoimmune responses often appear to be associated with antitumor responses (88, 90). Gogas and colleagues demonstrated that autoimmunity was an independent prognostic marker for improved relapse-free survival and overall survival in patients with melanoma who received adjuvant IFN-α-2β.[64] Autoimmunity was observed after a median of 3 months and in some cases after more than a year from IFN-α initiation (91). In the Gogas trial, serum was tested for anti-thyroid, antinuclear, anti-DNA, and anti-cardiolipin antibodies and patients were examined for vitiligo. As one of the goals of our investigational therapy is to induce an autoimmune response against the tumor, it is reasonable to assess for autoantibodies or clinical manifestations of autoimmunity. Serum will be assessed serially before and after hematopoietic and immune cell rescue for increased levels of autoantibodies including antithyroid antibodies (anti-thyroglobulin, anti-microsomal antibodies), antinuclear antibodies, anti-double stranded DNA antibodies, and anti-cardiolipin antibodies. Rheumatoid factor, thyroid stimulating hormone, thyroxine, and triiodothyronine levels will also be measured. Investigators will assess for symptoms of other autoimmune disorders during the history that might not be captured on these laboratories, and patients will be examined for the clinical manifestations such as vitiligo on a regular basis.

Participant Selection and Enrollment Procedures

Inclusion Criteria

Histologically confirmed Stage IV, TxNxM1 colon adenocarcinoma with a surgically accessible primary or metastatic site.

Estimated survival of 6 months or greater

Primary may be in place

Age 18-70

Must have an ECOG performance status of 0 or 1

Must have adequate organ and marrow function. Specifically:

Absolute neutrophil count (ANC)>1500/4,

Platelet count ≥100×10$^9$/L

Total bilirubin ≤2.0× the upper limit of normal (ULN)

Alkaline phosphatase, AST, and/or ALT<2.5× the ULN for patients without evidence of liver metastases; <5×ULN for patients with documented liver metastases Serum creatinine <2.0 mg/dL Hemoglobin >9 g/dL Patients may be transfused or receive epoetin alfa to maintain or exceed this level up to the hemoglobin level recommended on the current label for epoetin alfa. There is concern that hemoglobin levels greater than the level recommended by the current labeling have been associated with the potential increased risk of thrombotic events and increased mortality. Also, a rapid increase in hemoglobin may exacerbate hypertension (a concern in patients with pre-existing hypertension and if bevacizumab is administered).

Cardiac ejection fraction >40% by transthoracic echo or MUGA scan within 12 wks of transplant Adequate pulmonary function tests (PFTs) within 6 wks of transplant DLCO≥60% predicted Patients must be HIV negative No prior therapy which would preclude the use of total body irradiation Pathology must be reviewed and diagnosis confirmed by Stanford University Medical Center Ability to understand and the willingness to sign a written informed consent document.

Ability and capacity to comply with the study and follow-up procedures.

Exclusion Criteria

Disease-Specific Exclusions

Radiotherapy within 28 days prior to the day of tumor resection (Day 1).

No myelosuppressive chemotherapy within 28 days prior to the day of tumor resection History of brain metastases, regardless if treated.

Co-Morbid Diseases or Intercurrent Illness

Active infection or fever >38.5° C. within 3 days of starting treatment

History of other malignancies within 5 years prior to Day 1 except for tumors with a negligible risk for metastasis or death, such as adequately controlled basal cell carcinoma, squamous-cell carcinoma of the skin, carcinoma in situ of the cervix, early-stage bladder cancer, or low-grade endometrial cancer Malignancies that have undergone a putative surgical cure (i.e., localized prostate cancer post-prostatectomy) within 5 years prior to Day 1 may be discussed with the Medical Monitor.

History or presence of autoimmune disorders requiring treatment

Any other medical conditions (including mental illness or substance abuse) deemed by the clinician to be likely to interfere with a patient's ability to provide informed consent, cooperate, or participate in the study, or to interfere with the interpretation of the results.

Inadequately controlled hypertension (defined as systolic blood pressure >150 and/or diastolic blood pressure >100 mmHg on antihypertensive medications)

Any prior history of hypertensive crisis or hypertensive encephalopathy

New York Heart Association (NYHA) Grade II or greater congestive heart failure (see Appendix A)

History of myocardial infarction or unstable angina within 6 months prior to study enrollment History of stroke or transient ischemic attack within 6 months prior to study enrollment Significant vascular disease (e.g., aortic aneurysm, aortic dissection)

Symptomatic peripheral vascular disease

Evidence of bleeding diathesis or coagulopathy that is not intentionally pharmacologically-induced Serious, non-healing wound, ulcer, or bone fracture Proteinuria at screening as demonstrated by either:

Urine protein:creatinine (UPC) ratio ≥1.0 at screening OR

Urine dipstick for proteinuria ≥2+(patients discovered to have ≥2+ proteinuria on dipstick urinalysis at baseline should undergo a 24 hour urine collection and must demonstrate ≤1 g of protein in 24 hours to be eligible).

Radiation-Specific Exclusions

Prior radiation to >25% of the marrow

Pregnancy
Women who are pregnant or breast feeding, or women/men able to conceive and unwilling to practice an effective method of birth control.
Women of childbearing potential must have a negative urine or serum pregnancy test within 7 days of study entry.
Nursing patients will be excluded Treatment Plan
Investigational Agent Administration
We will undertake a pilot trial to assess the safety and feasibility of treating adult metastatic colorectal cancer patients who have a surgically accessible sterile primary or metastatic site with an autologous tumor cell/TLR9 agonist vaccine followed by autologous hematopoietic and immune cell rescue.

Screening

The patients of the gastrointestinal medical oncology and surgical oncology practices of physicians in a major Cancer Center will be screened for the inclusion and exclusion criteria described in sections 3.1 and 3.2. Basic eligibility requires adult (aged 18-70 years) metastatic colon cancer patients who have a life expectancy greater than 6 months as well as a surgically accessible sterile primary or metastatic site and an ECOG performance status of 0 or 1. The trial, its goals, risks and benefits will be extensively discussed with the patient and they will be given adequate time to review the written informed consent and ask questions. A written informed consent must be signed prior to trial entry.

During the screening period, patients will have a complete history and physical examination performed including demographics, vital signs, height, and weight.

Within 7 days of tumor resection, baseline labs including a CBC with differential, complete metabolic panel, CEA, CA 19-9, autoimmunity panel, thyroid stimulating hormone, thyroxine, and triiodothyronine levels will be obtained. Within 4 weeks of the baseline apheresis, all patients will have a baseline CT scan of the chest/abdomen/pelvis, pulmonary function testing with spirometry and diffusing capacity, transthoracic echo or MUGA scan, and additional laboratory analysis including: hepatitis panel (HepBsAgA, HepB total core Ab, Hep total Ab, Hep C Ab, qualitative Hep C PCR), HIV-1 Ag, HIV 1 &2 antibody, HIV PCR, HSV-1 &-2 Ab, HTLV-1 & -2 Ab, RPR, VZV Ab, CMV IgG & IgM, and baseline autoimmunity screen (ANA, anti-double stranded DNA, anti-microsomal antibodies, anti-thyroglobulin, anti-cardiolipin, rheumatoid factor).

Central Line Placement
Insertion of a 12 French Cook catheter will be done prior to the baseline apheresis.

Baseline Apheresis
Prior to metastectomy and if needed, primary tumor resection, patients will undergo a first apheresis to establish baseline immune markers. This apheresis will be performed in the blood bank in the standard manner. The goal of this apheresis is twofold: (1) to obtain >$10^8$ PBMCs and lymphocytes which will be frozen in aliquots of 1 to 10 million, and (2) to collect 100 mL of autologous plasma for use in tumor vaccine preparation and cryopreservation to avoid the use of allogeneic human serum. The apheresis will take approximately 1 hour and approximately 24 mL of blood will be removed which is roughly equivalent to 8 tablespoons.

Resection
Within 1 week (preferably days) of the baseline apheresis, the patient will be taken to the operating room for resection of tumor either in the form of metastatic disease or the primary when clinically indicated and using standard surgical procedures.

Tumor Cell Processing and Vaccine Creation

For vaccination, patients must have cryopreserved autologous tumor cells prepared as follows. The Surgical Pathology service will aseptically collect freshly resected colon cancer tissue for vaccine preparation. Tumor specimens will be placed in cold (2-8° C.) medium consisting of RPMI supplemented with 10% autologous plasma. In general, up to 5 g of tumor will be collected for vaccine preparation. Tumor samples will be maintained cold and transferred to the Stanford Blood & Marrow Transplant (BMT) Laboratory for processing. Freshly resected tumors will be dissociated under aseptic conditions into single-cell suspensions by mechanically mincing tumor into small pieces of approximately 5 mm$^3$, followed by enzymatic digestion in Dulbecco's phosphate-buffered saline (DPBS) with an enzyme mixture (Liberase, Roche, Indianapolis, Ind.) containing collagenase types I and II, and deoxyribonuclease (Pulmozyme, Genentech, South San Francisco, Calif.). The digestion will be performed at room temperature with gentle agitation until dissociation is complete. The resulting cell suspension will be filtered through nylon mesh (Nytek; TETKO Inc, Briarcliff Manor, N.Y.). After washing with DPBS ($Ca^{2+}$- and $Mg^{2+}$-free), the cells will be resuspended in autologous plasma. Samples will be removed for cell count and viability determination, sterility assessment and endotoxin measurement. The tumor cell suspension will be concentrated to yield aliquots of 2×$10^7$ cells in 90% autologous plasma plus 10% dimethylsulfoxide (DMSO Protide Pharmaceuticals, Lake Zurich, Ill.) for cryopreservation. Vaccine aliquots will be frozen and stored in vapor phase liquid nitrogen at or below −155° C. until released for immunization and immunologic assay (see Section 5.2.1 for release testing criteria). Storage freezers are continuously monitored and equipped with remote alarms.

For vaccination, cryopreserved tumor cells will be thawed and washed twice in DPBS. Ten to twenty million viable tumor cells in 1 ml will be transferred to the Stanford Blood Center and irradiated to a dose of 25 Gy. The cells will be returned to the BMT Laboratory and resuspended in 0.5-2 ml of DPBS containing 6 mg CpG to complete the vaccine formulation. Approximately 10% of the volume will be removed for look-back sterility assessment of the vaccine. A dose of 1×$10^7$ viable cells in up to 2 ml final volume will be loaded into a 2 cc syringe and released for vaccination as described below.

Vaccinations

All injections will be carried out at the GCRC or in the Stanford Cancer Center oncology clinic. Vaccinations will occur at weeks 1 and 2 after surgery (minimum of 7 days after surgery and 7 days between injections) and at a minimum of 7 days after autologous hematopoietic and immune cell rescue. Patients will be vaccinated subcutaneously at one site as per the vaccination schedule. Each dose of vaccine will consists of 1×$10^7$ autologous irradiated tumor cells and 6 mg CpG in DPBS.

Appropriate sites of vaccination include: the outer upper arm, abdomen, buttock, or outer thigh. The site of injection will be identified and should be free of skin irritation. The area will be cleansed with an alcohol or betadine swab. After the site dries, approximately 1-2 inches (2.5-5 cm) of skin will be held taut and the vaccine will be injected at a 45 degree angle using a 25-27 gauge ⅝" needle and a 2 mL syringe. After needle withdrawal, pressure will be held over the site with sterile gauze until hemostasis is achieved. The site of injection will be marked and the location will be recorded in the source documentation.

After each injection, the patient will be monitored for at least 1 hour. Vital signs will be taken 30 minutes after each injection.

Week 4 CT Scan of chest/abdomen/pelvis

If stable disease, patients will continue off chemotherapy.
  If patients have evidence of progressive disease, capecitabine monotherapy (1000 mg/m² twice daily for 14 days every 3 weeks) or other minimally myelosuppresive but effective agent at will be initiated. Patients will then continue with aphereses 2 and 3 at weeks 7 and 8 respectively.

Apheresis 2 (for Immune Cell Rescue)

At week 7, patients will undergo a second apheresis for a minimum collection goal of >3×10⁸ unstimulated PBMCs/kg patient weight. PBMCs will be cryopreserved in autologous plasma with 10% DMSO at a dose of at least 2×10⁸/kg for immune cell rescue. An additional 10 or more vials containing 1-10 million PBMCs will be cryopreserved for use in for future ex vivo experiments.

Apheresis 3 (for Hematopoietic Cell Rescue)

At 7-21 days after Apheresis 2, patients will receive G-CSF injections subcutaneously at a dose of 5-10 μg/kg/day for 4 days (goal Sunday through Thursdays). On day 4, the peripheral blood CD34+ cell count will be checked. If the CD34+ count is <5/μL, patients will undergo apheresis on day 4 followed by a fifth dose of G-CSF on day 5 and an additional apheresis on day 5. The product of these collections will be batched together. The combination of the two collections should be adequate for the rescue. If the CD34+ count is >10, one collection will be done on the afternoon of Day 5 (e.g., Thursdays). Using an Isolex 300 device, CD34+ progenitor cells will be isolated from the apheresis product as per manufacturer's instructions. These collections will be cryopreserved.

CT Scan of the Chest/Abdomen/Pelvis with Contrast Will be Done at Week 8
  If stable disease on or off chemotherapy, continue to conditioning regimen of fludarabine and fTBI followed by autologous hematopoietic and immune cell rescue.
  If progressive disease, initiate or add other chemotherapeutic agents [e.g., capecitabine and oxaliplatin (or irinotecan)+/−bevacizumab] for 3 cycles, then reassess with repeat CT scans at week 18. Appropriate chemotherapy regimens will be determined by the investigators.
  The risks and benefits of each chemotherapeutic or targeted agent will be reviewed at the time of informed consent, at treatment initiation, and whenever the patient has questions.

Week 18 Post-Chemotherapy Re-Staging CT Scans

If applicable, the patients will be assessed for response to the chemotherapy with a repeat contrast CT scan of the chest, abdomen, and pelvis during the rest week of cycle 3.

If re-staging CT scans of the chest, abdomen, and pelvis show complete response, partial response, or stable disease as defined by traditional RECIST criteria (1), the patients will proceed to fTBI followed by autologous hematopoietic and immune cell rescue with re-infusion of the unstimulated and mobilized T cells gathered from aphereses 2 and 3 (see section 4.1.8 & 4.1.9).

Patients, who have evidence of progressive disease on the week 18 re-staging CT scan will be considered for second line regimens such as cetuximab and irinotecan or whatever regimen is deemed most appropriate by the investigators while adhering to standard of care practices. If their performance status and organ function is inadequate for further chemotherapy, they will be discontinued from the trial. If second line therapy induces stabilization of disease or partial response, those patients can then undergo fTBI followed by autologous hematopoietic and immune cell rescue if they continue to meet the other eligibility criteria.

Autologous Hematopoietic and Immune Cell Rescue

Patients who have response on chemotherapy or stable disease on or off chemotherapy will then undergo an induction regimen of fludarabine 30 mg/m² IV daily over 45 minutes for 3 days followed by fTBI. The dose of the fTBI will be determined according to the cohort the patient enters into:

FTBI dose will be determined using a 3+3 dose escalation scheme with the following dose levels:
  Dose level #1: 400 cGy (administered as 200 cGy once daily for two days)
  Dose level #2: 600 cGy (administered as 200 cGy once daily for three days)
  Dose level #3: 800 cGy (administered as 200 cGy once daily for four days)

For example, for dose level #1, the conditioning regimen schedule would be:

| | |
|---|---|
| D-4 | Fludarabine |
| D-3 | Fludarabine |
| D-2 | Fludarabine |
| D-1 | fTBI |
| D 0 | fTBI followed by hematopoietic and immune cell transplant |

| Fludarabine | Fludarabine | Fludarabine | fTBI | fTBI + transplant |
|---|---|---|---|---|
| ↓ | ↓ | ↓ | ↓ | ↓ |
| ↓ | ↓ | ↓ | ↓ | ↓ |
| D-4 | D-3 | D-2 | D-1 | D0 |

At the higher dose levels, fludarabine would start 1 to 2 days earlier depending on the number of days of fTBI.

See section 6.3.1 for details on dose escalation scheme.

The target of T cell depletion at the time of transplant is an ALC<0.1

Patients will be hydrated prior to, during, or after fTBI as clinically indicated.

Most patients will require anti-emetics or sedatives to decrease nausea and vomiting. Furosemide may be utilized to maintain the patient's weight at or near the admission baseline weight.

If HSV-1 or -2 positive on screening, acyclovir 400 mg orally twice daily will be given starting the first day of fTBI until 1 year after the day of rescue (Day 0).

The frozen hematopoietic and immune cells will be transported to the outpatient Stanford Cancer Center BMT Infusion Treatment Area (ITA), thawed in a warm water bath, and infused through a central venous catheter as rapidly as possible. Patients will be pre-medicated with hydrocortisone 100 mg IV and diphenhydramine 50 mg IV 30 minutes prior to cell infusion.

Post-Transplant Vaccine Boost

If patients have adequate coagulation parameters, i.e., platelets >50, 000, INR <1.5, they will receive a vaccine boost at week 1 post-rescue. The boost will be a minimum of 7 days after transplant.

Post-Transplant Care

Patients will be prophylaxed against infection with the following:
  If HSV-1 or -2 positive, acyclovir 400 mg p.o. bid starting on first day of fTBI
  When ANC<500, ciprofloxacin 500 mg orally daily will be started.
  Days +30-60: Bactrim 160 mg/800 mg p.o. bid, Saturday and Sunday only.
    No PCP prophylaxis will be given prior to D+30 as may delay hematopoietic reconstitution
  Serum CMV monitoring q week until Day +60

Neupogen will not be given initially as there is some evidence that neupogen can induce a TH2 response in lymphocytes which may attenuate our CTL anti-tumor effect. Yet, if more than 2 of the first 6 patients experience neutropenic fever requiring hospital admission beyond 7 days or prolonged neutropenia beyond 2 weeks, the investigators can either decrease the fTBI dose according to the protocol or add neupogen 5 mcg/kg sc daily starting day +6 until wbc>5000.

If admitted to the hospital, patients will be followed by the Bone Marrow and Transplantation (BMT) service following standard of practice for post-autologous transplantation care.

If not admitted to the hospital, patients will be followed in the BMT Day Hospital for signs of infection. CBCs and BMT panels will be performed a minimum or three times per week during the first 35 days. Weekly chest radiographs will be performed. A history and physical examination will occur at each visit.

Follow-Up after Hematopoietic Cell Reconstitution

After rescue, patients will be evaluated every month with physical exams including vital signs, basic laboratories, and CEA/CA 19-9 levels for 3 months then every 2-4 months as clinically indicated. Immune monitoring will be performed as described in section 4.1.15.3. CT scans of the chest/abdomen/pelvis will be done monthly for 2 months then every 2 months to evaluate for progression. Patients who withdraw from treatment due to progressive disease will be seen within four weeks of the determination of progressive disease for a final study visit. Patients who withdraw due to intolerance of treatment should be followed weekly until all toxicities have reverted to Grade ≤2 or have stabilized in the opinion of the Investigator, at which point they will undergo the final visit. All patients who withdraw for any reason other than progressive disease will be seen within 4 weeks of withdrawal for a final visit.

It is anticipated that several months will be required for the CTLs to exhibit antitumor activity. Patients with "symptomatic" disease progression after rescue will be treated with best available systemic therapy. But when clinically appropriate, chemotherapy will be held for at least 3 months post-transplant to allow for the CTLs to proliferate and act.

Monthly for 3 months post-rescue then every 2-4 months as clinically indicated
    Physical exam including vital signs
    Laboratories: CBC with differential, complete metabolic panel, and if appropriate
    CEA and CA 19-9
    Contrast CT chest/abdomen/pelvis if creatinine within normal limits in month 1 and 2 then every 2 months
Final Visit
    At the Final Visit, the following procedures will be performed:
    Elicitation of adverse events and toxicity grading according to the NCI CTC
    Recording of concomitant medications
    Complete physical exam including vital signs and ECOG performance status
    Laboratories:
        CBC with differential and platelet count
        Comprehensive metabolic panel
        CEA and CA 19-9 if appropriate

| Immune monitoring protocol | | | | | | | | | | | | | |
|---|---|---|---|---|---|---|---|---|---|---|---|---|---|
| Test | Screen | A1 | A2 | A3 | Start Cond. | D0 | Daily Post-rescue | Week +2 | +1 mo | +3 mo | +6 mo | +12 mo | +18 mo | Term. |
| CBC with Differential | X | X | X | X | X | X | X until ANC > 500 | | X | X | X | X | | X |
| Absolute # of CD3+/CD4+/CD8+[a] | | X | | | | | | X* | X | X | X | | | |
| In vitro resp. to recall antigens[b] | | X | X | | | | | | | X | X | X | | |
| IL-7, IL-15[c] | | X | X | | X | X | | X | X | X | X | X | | |
| % Proliferating T cells[d] | | X | X | | | | | | X* | X | X | X | | |
| CEA, CA 19-9[e] | X | X | | | X | | | | X | X | X | X | | X |
| In vitro antitumor immune resp.[f] | | X | X | | | | | | X* | X | X | X | | |
| Auto-immunity panel[g] | X | | | | | | | | | X | X | X | | |

[a]CD3+/CD4+/CD8+: absolute numbers/percentages including naive (CD62L+CCR7+CD45RA+), central memory (CD62L+CCR7+CD45RO+), and effector memory (CD62L−CCR7−CD45RO+) subsets.
[b]In vitro responses to recall antigens: tetanus toxoid, HSV, Varicella, CMV
[c]Serum IL-7 and IL-15: assessment of cytokine-associated homeostatic expansion of T cells
[d]% Proliferating T cells: Ki-67, TREC
[e]CEA, CA 19-9: q month × 3 after transplant then q2-4 months as clinically indicated and only if baseline level was high.
[f]Anti-tumor immune responses will assessed in vitro: purified total T cells or purified CD4+ and purified CD8+ T cells (and their memory subsets) will be used as responder cells ($50 \times 10^3$/well). Stimulator cells will be irradiated (5,000 cGy in vitro) single cell suspensions of tumor cells ($50 \times 10^3$) or purified dendritic cells pulsed with the tumor cell lysate obtained by sonication and freeze/thaw. Measurements of responses include proliferation ($^3$H-thymidine incorporation) and production of the cytokines IL-2, IFN-γ, TNF-α, and IL-10 assayed by intracellular staining or in triplicate culture well supernatants by ELISA.
[g]Autoimmunity panel: ANA, anti-ds-DNA antibodies, anti-thyroid antibodies, anti-microsomal antibodies, anti-thyroglobulin antibodies, anti-cardiolipin antibodies, rheumatoid factor, thyroid stimulating hormone, thyroxine, and triiodothyronine levels
*if ALC > 1500
Key:
A: Apheresis;
Screen: Screening;
D: Day;
Flud: Fludarabine;
D0: Day of hematopoietic and immune cell rescue;
Mo: month Screening
CBC with differential (ALC, ANC, platelets)
CEA, CA 19-9
Autoimmunity panel
Apheresis 1
CBC with differential (ALC, ANC, platelets)
CEA, CA 19-9 if applicable
T cell subsets
Assessment of in vitro response to recall antigens
IL-7, IL-15
Proliferating T cell indices: Ki-67, TREC
Assessment of in vitro antitumor immune response
Apheresis 2
CBC with differential (ALC, ANC, platelets)
Assessment of in vitro response to recall antigens
IL-7, IL-15
Proliferating T cell indices: Ki-67, TREC
Assessment of in vitro antitumor immune response
Apheresis 3
CBC with differential (ALC, ANC, platelets)
Start of conditioning: Day 1 of fludarabine
CBC with differential (ALC, ANC, platelets)
CEA, CA 19-9 if applicable
IL-7, IL-15
Day of autologous hematopoietic and immune cell rescue (Day 0)
CBC with differential (ALC, ANC, platelets)
IL-7, IL-15 Daily after rescue until ALC>500, ANC>500, platelets>20,000
CBC with differential (ALC, ANC, platelets)
Week +2 post-rescue
IL-7, IL-15
Month +1
CBC with differential (ALC, ANC, platelets)
T cell subsets (if ALC>1500)
CEA, CA 19-9 if clinically indicated
IL-7, IL-15
Proliferating T cell indices: Ki-67, TREC
Assessment of in vitro antitumor immune response
Month +3
CBC with differential (ALC, ANC, platelets)
CEA, CA 19-9 if applicable
T cell subsets
Assessment of in vitro response to recall antigens
IL 7, IL-15
Proliferating T cell indices: Ki-67, TREC
Assessment of in vitro antitumor immune response
Month +6
CBC with differential (ALC, ANC, platelets)
CEA, CA 19-9 if applicable
T cell subsets
Assessment of in vitro response to recall antigens
IL-7, IL-15
Proliferating T cell indices: Ki-67, TREC
Assessment of in vitro antitumor immune response
Autoimmunity panel
Month +12
CBC with differential (ALC, ANC, platelets)
CEA, CA 19-9 if applicable
T cell subsets
Assessment of in vitro response to recall antigens
IL-7, IL-15
Proliferating T cell indices: Ki-67, TREC
Assessment of in vitro antitumor immune response
Autoimmunity panel
Month +18
Autoimmunity panel
Study termination
CBC with differential (ALC, ANC, platelets)
CEA, CA 19-9 if applicable
As needed based on symptoms (Per the discretion of the investigator)
Imaging
Laboratory assessment
General Concomitant Medication and Supportive Care Guidelines
Supportive Medications
Nausea, vomiting, or both may be controlled with antiemetic therapy.
Mild to moderate allergic or hypersensitivity reactions can be treated with antihistamines such as diphenhydramine.
Unacceptable Concomitant Medications
The following medications may not be administered to study patients during the treatment period of the trial:
  Pentastatin will be avoided during fludarabine administration given the high incidence of pulmonary toxicity when given concomitantly
  Chemotherapy, biological therapy or radiotherapy other than specified in the protocol.
  Any investigational treatments
All other medical conditions should be treated according to current standards of care at the discretion of the Investigator. All concomitant medications and therapies must be recorded on the appropriate CRF (Case Report Forms), with indication, dose, route, frequency and date of administration. In general, concomitant medication should be stabilized before screening and should remain constant during the course of the study, whenever possible. Any change must be documented on the CRF.

Duration of Active Therapy

From baseline apheresis to the vaccine boost 7 days after transplant, the various therapies (e.g. resection, vaccinations, chemotherapy, fTBI, autologous hematopoietic and immune cell rescue) will take approximately 11 weeks if no chemotherapy is required to 28 or more weeks if chemotherapy is required.

Duration of Follow Up

All patients, including those who discontinue protocol therapy early, will be followed clinically for 3 years after transplant for response and progression; and if necessary after 3 years for survival information.

Please refer to 4.1.15 for follow-up procedures on patients who completed all study treatments. In brief, they will be followed with monthly visits x3 then every 2-4 months for 3 years.

For those patients that discontinued the protocol early, follow-up will be every 2-4 months after their final study visit for updates on initiation of subsequent-line therapy and overall survival until the final analysis. Patients discontinuing the study due to a drug-related adverse event must be followed for four weeks or until resolution of stabilization of the event.

Criteria for Removal from Study

Patients will be removed from the study if:
  Progressive disease compromises organ function or performance status making them ineligible for total body radiation or autologous hematopoietic and immune cell rescue
  Patient withdraws consent
  Lost to follow-up
  Death A genuine effort must be made to determine the reason(s) why a patient fails to return for the necessary visits or is discontinued from the trial. It will be documented whether or not each patient completed the clinical study. If for any patient, study treatment or observations were discontinued the reason will be recorded on the appropriate case report form.

Alternatives

Alternatives to this Study Include:

Standard of care treatment with systemic chemotherapy and resection or radiation of specific tumor sites as clinically indicated Another clinical trial Best supportive care Planned Procedures for Protecting Against and Minimizing all Potential Risks Acquisition of tumor specimens for preparation of vaccine will be performed by oncologic surgeons. Preferred sites will be intraperitoneal metastases, liver metastases, pulmonary disease, or in rare cases, the extraluminal portion of a bulky primary.

The patients will be closely monitored throughout the trial with frequent physician visits and AE monitoring.

Investigational Agent and Procedure Information

Aphereses

Apheresis is not a routine part of colon cancer management and is thus considered an investigational component. This procedure will enable us to collect the unstimulated immunized cytotoxic T lymphocytes (CTLs) (apheresis 2), and the G-CSF stimulated hematopoietic progenitor cells (apheresis 3) as well as perform immune monitoring (apheresis 1, 2, &3). Cells from aphereses 2 and 3 will be transplanted back into the lymphodepleted patient with the autologous hematopoietic and immune cell rescue. The re-infused immunized CTLs will undergo homeostatic expansion which will ideally induce regression in residual tumor. The re-infused hematopoietic progenitor cells will aide in cell recovery after the fractionated TBI, reducing the duration of cytopenia.

Risks

Complications are rare. Life-threatening complications are extremely rare.

Potential risks and/or discomforts of apheresis include:

Nervousness, light-headedness, fainting

Infection

Bruising

Blood loss

Air embolism

Potential problems with the anticoagulant(s) used during the apheresis process include:

Muscle cramping

Numbness, tingling sensations

Chills

Feelings of anxiety

Nausea, vomiting

Bleeding

Supportive Care

Adverse effects will be treated symptomatically as clinically indicated.

Vaccine

Tumor Cell Processing

Vaccine preparation requires extensive handling of resected tumor to generate single cell suspensions. In addition, the cells are combined with recombinant enzymes and CpG during processing. Release testing of the product to ensure its safety for injection will be according to the following schedule.

| Assay | Test sample | Method | Release criteria |
|---|---|---|---|
| Sterility | Resected tumor suspension | Tryptic Soy Broth Fluid Thioglycolate Medium | No growth |
| Sterility | Biosafety cabinet settle plates | Blood agar | No growth |
| Endotoxin | Resected tumor suspension | LAL Kinetic Chromagenic Assay | <5 EU/ml |
| Cell count | Pre-freeze | Manual (hemocytometer) | >5 × $10^7$ cells |
| Cell count | Post-thaw | Manual (hemocytometer) | >1 × $10^7$ cells |
| Cell viability | Post-thaw | Trypan blue exclusion | >50% viable |
| Sterility | Final formulation | Tryptic Soy Broth Fluid Thioglycolate Medium | No growth |

Sterility testing will use the BioMerieux BactAlert system with both Fluid Thioglycollate Medium and Tryptic Soy Broth. This system has been validated within the Clinical Microbiology Laboratory at Stanford Hospital and Clinics and has been shown to be at least as sensitive to microbial contaminants as standard USP compliant assays. Vaccines showing evidence of microbial contamination either by detectable growth in sterility cultures or endotoxin levels above the stated limit will not be released for injection.

Vaccines showing evidence of microbial contamination either by detectable growth in sterility cultures or endotoxin levels above the stated limit will not be released for injection.

CpG

Agent Accountability

The CpG will be kept in a secured location within the Blood and Marrow Transplantation Lab where only the investigators will have access to it.

Procedure

Injections will be administered by a person designated by the investigator (e.g., study nurses, physicians) in response to written orders from the investigator.

Risks

The most frequent adverse events seen with CpG agents have been those related to the expected immunomodulatory pharmacologic effects. These include local injection reactions, systemic flu-like symptoms, and hematologic changes.

Local injection site reactions: pain, erythema, edema, inflammation

Flu-like symptoms: fever, myalgia, arthralgia, fatigue, headache, rigors, and/or musculoskeletal pain Neutropenia and neutropenic fever Thrombocytopenia Infrequent hypersensitivity reactions Rare possibility of autoimmune disorders: e.g. autoimmune thyroiditis, Sjogren's syndrome Potential for seroconversion for anti-single stranded and double-stranded DNA antibodies, ANA, rheumatoid factor (can be asymptomatic)

Sepsis and Sepsis-related adverse events

Rare cardiac ischemia, cardiac arrhythmia (most had a cardiac history or recognized risk factors)

Supportive Care

For local injection site reactions:

Treat symptomatically with hot or cold compresses at the site, acetaminophen for pain or inflammation, antihistamines for pruritis.

Options for future injections: splitting injection into more than one site, rotating the site of injection, avoiding injection into a site with an existing local reaction, using small gauge needles.

Symptomatic treatment to alleviate flu-like symptoms, e.g. acetaminophen

Because of small risk of hypersensitivity reaction, patients will be observed in the Oncology or BMT infusion center for 60 minutes after each injection.

Patients with significant cardiac disease or EF<40% will be excluded from the study Patients will be monitored closely for neutropenia, NF, and sepsis Conditioning Regimen Fludarabine Pharmacology Fludarabine monophosphate is a purine analogue used extensively in the treatment of lymphoid malignancies, particularly CLL and low grade NHL. Fludarabine is phosphorylated intracellularly in several steps to its active form 2-fluoroadenosine arabinoside triphosphate (93). Although fludarabine functions primarily as an antimetabolite it does affect both dividing and non-dividing cells. Fludarabine may function as a radiosensitizer (94), which may enhance the immunosuppressive properties of our regimen but also the toxicity.

Procedure

Total doses of 90 mg/m$^2$ to 240 mg/m2 have been used as part of minitransplant regimens with well-characterized and acceptable toxicity (95-3). In this trial, patients will be given 30 mg/m$^2$ IV over 45 minutes in the outpatient BMT infusion center for 3 days prior to the start of fTBI.

Toxicities

At the doses used in this study the main side effects will be immunosuppression and myelosuppression.

Other adverse reactions that occur in >10% of cases include:

Cardiovascular: Edema

Central nervous system: Fever (60-70%), fatigue, pain, chills

Dermatologic: rash

Gastrointestinal: mild nausea/vomiting, anorexia, diarrhea, gastrointestinal bleeding (3-13%)

Genitourinary: urinary tract infection

Hematologic: myelosuppression (nadir 10-14 days; recovery 5-7 weeks), anemia, neutropenia (grade 4: 59%; nadir: ~13 days), thrombocytopenia (50-55N; nadir: ~16 days)

Neuromuscular & skeletal: generalized weakness, myalgia, paresthesia

Ocular: visual disturbance; rare blindness

Respiratory: cough, pneumonia, dyspnea, upper respiratory infection

Infection

Diaphoresis

Rare: autoimmune hemolytic anemia

Supportive Care

Anti-emetics, blood and platelet transfusions will be given as clinically indicated.

Other toxicities will be managed symptomatically as they arise.

No concurrent pentastatin will be administered given the high incidence of fatal pulmonary toxicity when given in combination with fludarabine.

Fractionated Total Body Irradiation fTBI is not a normal part of clinical management for colon cancer. However, its use as part of a hematopoietic cell preparatory regimen is longstanding and we will follow our institution's well-established guidelines.

Procedure

TBI will be given in 200 cGy fractions daily using up to a 15 mV linear accelerator at a rate of <15 cGy/minute. Dosimetry calculations will be performed by the radiation physicist. Patient positioning and treatment planning procedures will be performed according to institutional standard practice.

fTBI will be initiated the day after the last dose of fludarabine which depending on the dose cohort will either be day −1 if in the 400 cGy cohort, day −2 if in the 600 cGy cohort or day −3 if in the 800 cGy cohort.

Supportive Care

Beginning the day prior to irradiation, patients may receive intravenous fluids as clinically indicated on an outpatient basis. Most patients will require anti-emetics and/or sedatives to decrease nausea and vomiting. Furosemide will be utilized to maintain the patients' weight at or near the admission baseline weight.

Toxicities Associated with FTBI Include:

Nausea and vomiting

Temporary alopecia

Cytopenias with resultant risk of life-threatening infections and/or hemorrhage

Risk lasts until hematopoietic reconstitution

Parotid swelling with elevation of serum amylase (rare)

Radiation pneumonitis

Diarrhea

Oral mucositis

Probable permanent sterility in all patients

Long term survivors may develop cataracts; some may require corrective surgery and the use of soft lenses Rare cases of second malignancies Skin irritation Supportive Care Diuretics, anti-pyretics and other agents will be given to manage the toxicities as clinically indicated.

Toxicities During the Infusion should be Minimal

Volume overload

Fever, chills

DMSO odor: DMSO will be infused along with the cells. It is excreted through the lungs. Its characteristic odor may be noticeable for 2-3 days after the infusion.

Risks after the Rescue

Infection during the period of cytopenia. The period of cytopenia is expected to be short as this is not a fully myeloablative conditioning regimen. Even without re-infusion of cells, period of cytopenia is not expected to be more than 10 days.

Due to the nature of autologous hematopoietic cell transplantation, hospitalizations for febrile neutropenia are common and most often easily managed. There are no baseline data with which to estimate the risk of hospitalization with the above dose levels though they are considerably lower than that which is routinely used in myeloablative transplantation regimens for hematolymphoid malignancies.

Dosing Delays/Dose Modifications

Vaccine Dose

Potential AE's

If greater than grade 1 skin reaction occurs at the injection site, subsequent injections should be given in a different site or adjacent to the first injection site.

Patients who experience toxicity according to that described in Table 6-1 may have their doses held or discontinued. If any grade 3 injection site reaction or systemic reaction occurs as characterized by hypotension, anaphylaxis, laryngeal edema, or hospitalization, no further vaccinations will be given.

TABLE 6-1

Autologous tumor cell-CpG 7909 Vaccine Dose Modifications

| CTC Grade Toxicity | During Any Treatment Cycle |
|---|---|
| Grade 3 injection site reaction or anaphylaxis | No subsequent vaccinations |
| Other Grade 3 or 4[a] | Omit dose until toxicity ≤ Grade 2, then resume dose |

Fludarabine

No dose modifications possible.

fTBI

Dose Escalation Rules

No dose modifications possible at each level but the dosing will be according to a 3+3 dose escalation theme:

The first three patients will be accrued to cohort #1 sequentially with no more than one accrued every 4 weeks.

If none of the 3 patients require hospital admission for >7 days for any reason or develop grade 4 non-hematologic toxicity, then the next three patients will accrue to dose level #2.

If one of the 3 patients has a hospitalization >7 days or grade 4 non-hematologic toxicity, then 3 more patients will be accrued sequentially to dose level #1. If 2 of 6 patients require hospitalization for >7 days or have grade 4 non-hematologic toxicity, accrual will be discontinued and amendments to the study considered. If the subsequent three patients do not require hospitalization for >7 days or develop grade 4 non-hematologic toxicity, then the next three patients will escalate to dose level #2.

The above rules also apply to escalation from dose level #2 to #3.

If two or more of the six patients accrued to dose level #2 or #3 require hospitalization for >7 days or develop grade 4 non-hematologic toxicity, then accrual will continue at the lower dose level (i.e. 800 cGy decreased to 600 cGy or 600 cGy decreased to 400 cGy) until 9 patients have been treated.

Autologous Hematopoietic and Immune Cell Transplant

No dose modifications possible.

Adverse Events and Reporting Procedures

Definitions of Adverse Events

Adverse Events

An Adverse Event (AE) is the development of an undesirable medical condition or the deterioration of a pre-existing medical condition following or during exposure to a pharmaceutical product, whether or not considered causally related to the product. An undesirable medical condition can be symptoms (e.g., nausea, chest pain), signs (e.g., tachycardia, enlarged liver) or the abnormal results of an investigation (e.g., laboratory findings, ECG). In clinical studies, an AE can include an undesirable medical condition occurring at any time, including run-in or washout periods, even if no study treatment has been administered.

Any detrimental change in a patient's condition subsequent to them entering the study and during the follow-up period should be considered an AE. When there is a deterioration in the condition for which the study treatment is being used, there may be uncertainty as to whether this is lack of efficacy or an AE. In such cases, unless the reporting physician considers that study treatment contributed to the deterioration or local regulations state to the contrary, the deterioration should be considered a lack of efficacy. Signs and symptoms of disease progression are therefore not considered AEs.

The development of a new cancer should be regarded as an AE. New cancers are those that are not the primary reason for administration of study treatment and have been identified after inclusion of the patient into the clinical study.

Serious Adverse Event

A Serious Adverse Event (SAE) is an AE occurring during any study phase (i.e., run-in, treatment, washout, follow-up), and at any dose of the investigational product, comparator or placebo, that fulfills one or more of the following criteria:

Results in death

Is immediately life-threatening

Requires inpatient hospitalization or prolongation of existing hospitalization

Results in persistent or significant disability or incapacity

Is a congenital abnormality or birth defect

Is an important medical event that may jeopardize the patient or may require medical intervention to prevent one of the outcomes listed above.

Any event or hospitalization that is unequivocally due to progression of disease, as determined by the investigator, must not be reported as an SAE. The causality of SAEs (their relationship to all study treatment) will be assessed by the Investigator.

Reporting of Adverse Events

Adverse events will be recorded at each visit, which is the first day of each cycle. If an adverse event occurs mid-cycle requiring medical attention, this will be recorded as well. The variables to be recorded for each adverse event include, but are not limited to, onset, resolution, intensity, action taken, outcome, causality rating, and whether it constitutes an SAE or not.

The intensity of the adverse event should be captured using CTCAE criteria, version 3.0, when possible.

Pregnancy should be excluded before enrollment. Should a pregnancy occur, it must be reported in accordance with the procedures described in Section 8.2. Pregnancy in itself is not regarded as an AE unless there is a suspicion that an investigational product may have interfered with the effectiveness of a contraceptive medication.

All non-serious adverse events will be reported to the FDA, IRB, and SRC.

If needed for progressive disease during this trial, chemotherapy will not be considered investigational. Unless unusual for the particular chemotherapy, Grade 3 or 4 AEs attributed to standard chemotherapy (when applicable) will not be considered reportable AEs.

Reporting of Serious Adverse Events

Investigators and other site personnel must inform the FDA, via a MedWatch form, of any serious or unexpected adverse events that occur in accordance with the reporting obligations of 21 CFR 312.32, and will concurrently forward all such reports to the FDA, IRB, and SRC. It is the responsibility of the investigator to compile all necessary information and ensure that the FDA receives a report according to the FDA reporting requirement timelines and to ensure that these reports are also submitted to the IRB and SRC at the same time.

A cover page should accompany the MedWatch form indicating the following:

Investigator Sponsored Study (ISS)

The investigator IND number assigned by the FDA

The investigator's name and address

The trial name/title

The SAE report will designate the causality of events in relation to all study medications and if the SAE is related to disease progression, as determined by the principal investigator.

If a non-serious AE becomes serious, this and other relevant follow-up information will also be provided to the FDA, IRB, and SRC.

All SAEs will be documented. The investigator is responsible for informing the IRB and/or the Regulatory Authority of the SAE as per local requirements.

All serious adverse events will be reported within 24 hours of first knowledge of the event's occurrence, the "Serious Adverse Event Report" must also be sent whether or not complete information is available at the time. If complete information is unavailable the Investigator must provide follow-up information to the FDA, IRB, and SRC as soon as it is known. In particular, the Investigator must inform these groups by phone and fax within 24 hours of occurrence of immediately life-threatening SAEs or SAEs with fatal outcome.

Correlative Studies
   Laboratory Correlative Studies
   All patient samples required for the studies detailed above will be collected and in both the overall study calendar and the immune monitoring study calendar. The BMT lab will handle the preservation and shipping of specimens.

STUDY CALENDAR

| | Pre-study | Sx. | Wk 1 V1 | Wk 2 V2 | Wk 4 CT | Wk 7 A2 | Wk 8 A3 | Cond. (Flud. + fTBI) $1^{st}$ day | Day of HICR (Day 0) | Day of Boost | Wk +2 | Mo +1 | Mo +2 | Mo +3 | Q 2-4 Mo. after Month +3 | Final Study visit |
|---|---|---|---|---|---|---|---|---|---|---|---|---|---|---|---|---|
| Informed consent | X | | | | | | | | | | | | | | | |
| Demographics | X | | | | | | | | | | | | | | | |
| History | X | | | | | | | | | | | | | | | |
| Concurrent meds$^a$ | X | X | | | | | | | X | | | X | X | X | X | X |
| Physical exam$^b$ | X | | | | X | | | X | | | | X | X | X | X | X |
| Vital signs$^c$ | X | X | | | | | | X | X | | | X | X | X | X | X |
| Height | X | | | | | | | | | | | | | | | |
| Weight$^d$ | X | | | | | | | | X | | | | | | | X |
| Performance status$^e$ | X | | | | | | | X | | | | | | | | X |
| CBC with Diff, Plts | X | | | | X | X | X | X | X | | | X | X | X | X | X |
| CMP | X | | | | | | | X | | | | X | X | X | X | X |
| PT, INR | X | | | | | | | | | | | | | | | |
| Infectious disease screen$^g$ | X | | | | | | | | | | | | | | | |
| Autoimmunity panel$^h$ | X | | | | | | | | | | | | | | | X |
| Serum/urine pregnancy test$^i$ | X | | | | | | | X | | | | | | | | |
| Central line placement | X | | | | | | | | | | | | | | | |
| Apheresis$^j$ | X | | | | X | X | | | | | | | | | | |
| Tumor resection | | X | | | | | | | | | | | | | | |
| Tumor measurements$^k$ | X | | | | X | | X | X | | | | X | X | | X | |
| Radiologic eval: CT scan C/A/P or MRI$^l$ | X | | | | X | | X | | | | | X | X | | X | |
| TTE or MUGA, PFTs$^m$ | X | | | | | | | | | | | | | | | |
| Standard chemotherapy as needed$^o$ | | | | | X | | X | | | | | | | X | | |
| Adverse event evaluation$^p$ | | | X | X | X | X | X | X | X | X | | X | X | X | X | X |
| Fludarabine$^q$ | | | | | | | | X | | | | | | | | |
| fTBI$^r$ | | | | | | | | X | | | | | | | | |
| Auto HICR$^s$ | | | | | | | | | X | | | | | | | |
| Acyclovir ppx$^t$ | | | | | | | | X | | | | | | | | |
| Bacterial ppx$^u$ | | | | | | | | X | | | | | | | | |
| CMV monitoring$^v$ | | | | | | | | | | | X | | | | | |
| Immune monitoring$^w$ | X | | | | X | X | X | | | | X | X | | X | X$^l$ | X |
| Other tests, as appropriate$^x$ | | | | | | | | | | | | | | | | |
| Survival assessment$^y$ | | | | | | | | | | | | | | | | X |

Key:
CT: computed tomography,
C/A/P: chest/abdomen/pelvis,
CMP: complete metabolic panel;
Cond: conditioning;
D: day,
Flud.: fludarabine;

-continued

STUDY CALENDAR

| | Pre-study | Wk 1 Sx. | Wk 2 V1 | Wk 4 V2 | Wk 7 CT | Wk 8 A2 | Cond. (Flud. + fTBI) A3 | Day of HICR (Day 1st day | Day of 0) Boost | Wk +2 | Mo +1 | Mo +2 | Mo +3 | Q 2-4 Mo. after Month +3 | Final Study visit |
|---|---|---|---|---|---|---|---|---|---|---|---|---|---|---|---| fTBI: fractionated total body irradiation,
HICR: hematopoietic and immune cell rescue,
Mo.: month,
MRI: magnetic resonance imaging,
ppx: prophylaxis,
Q: every,
Sx: surgery/resection of tumor;
Wk: week
$^a$Concurrent medications will be assessed by an investigator or ITA nurse at each visit or procedure
$^b$Complete physical examination including neurologic assessment will be done at screening, 1-2 days prior to resection and fTBI, day of autologous HSCT, and at termination visit. Otherwise, brief disease- and adverse event-focused history and focused physical exam will be done.
$^c$Blood pressure, heart rate, and temperature at screening, day of resection/autologous HSCT. Blood pressure and heart rate will be assessed before and 30 minutes after vaccinations.
$^d$Weight will be assessed at screening, day of resection/vaccinations/autologous HSCT, and at monthly clinic visits.
$^e$Performance status will be assessed using the criteria of the Eastern Cooperative Oncology Group (ECOG).
$^f$CEA and CA 19-9 will only continue to be checked if high on initial screening
$^g$Infectious disease screen: hepatitis panel (HepBsAgA, HepB total core Ab, Hep total Ab, Hep C Ab, qualitative Hep C PCR), HIV-1 Ag, HIV 1 &2 antibody, HIV PCR, HSV 1 & 2 Ab, HTLV-1 & 2 Ab, RPR, VZV Ab, CMV IgG & IgM
$^h$Autoimmunity panel: ANA, anti-ds-DNA antibodies, anti-thyroid antibodies, anti-microsomal antibodies, anti-thyroglobulin antibodies, anti-cardiolipin antibodies, rheumatoid factor, thyroid stimulating hormone, thyroxine, and triiodothyronine levels
$^i$For women of childbearing potential only. For all other women, document rationale in their medical history that confirms why patient is not of childbearing potential.
$^j$Aphereses: Pre-study: apheresis within 7 days prior to surgery for baseline immune markers Wk 7: apheresis for unstimulated cytotoxic killer lymphocytes (CTLs) Wk 8: G-CSF stimulated apheresis for hematopoietic progenitor cells (HPCs)
$^k$Tumor measurements: clinically for palpable lesions and radiographically using RECIST criteria; Also to be done at week 18 if still on chemotherapy.
$^l$Tumor assessment for all lesions will be evaluated according to RECIST criteria.
$^m$Within 4 weeks of the baseline apheresis, pulmonary function testing with spirometry and diffusing capacity, and transthoracic echo or MUGA scan will be performed to ensure adequate cardiac and pulmonary reserve.
$^n$Vaccinations will be performed subcutaneously at a minimum of seven days after tumor resection and after hematopoietic and immune cell rescue. The second vaccination will be given a minimum of 7 days after the first vaccination.
$^o$Standard chemotherapy will be given only if needed for progressive disease. The regimen will be at the discretion of the investigator.
$^p$All adverse events and grade ≥3 laboratory toxicities will be recorded at each visit.
$^q$Fludarabine 30 mg/m$^2$ IV daily over 45 minutes for 3 days followed by fTBI.
$^r$The dose of the fTBI will be determined according to the cohort the patient enters into and will be given once daily for 2-4 days
$^s$Autologous hematopoietic and immune cell rescue (HICR): thawed cells will be transfused as rapidly as possible. Patients will be pre-medicated with diphenhydramine 50 mg IV and hydrocortisone 100 mg IV 30 minutes before the transfusion.
$^t$Acyclovir prophylaxis: if HSV-1 or-2 positive, Acyclovir 400 mg p.o. bid starting on the first day of fTBI
$^u$Bacterial prophylaxis: When ANC <500, start Ciprofloxacin 500 mg orally daily. Days +30-60: Bactrim 160 mg/800 mg p.o. bid, Saturday and Sunday only for *pneumocystis carinii* prophylaxis.
$^v$Serum CMV monitoring once weekly for 1 year
$^w$Immune monitoring: See separate schedule in section 4.1.16.3. Immune monitoring will be done at month +1, +3, +6, +12, +18, and at termination of the study.
$^x$Routine laboratory monitoring per institution's standard practice for safety or as mandated by patients co-morbidities.
$^y$After study termination, patients will be followed for survival data approximately every 3 months. When possible, subsequent treatment history will be recorded.

Measurement of Effect

Anti-Tumor Effect

Patients will undergo re-staging CT scans of the chest/abdomen/pelvis at week 4 and week 8 to decide if standard chemotherapy is needed. If chemotherapy is initiated or continued at week 8, then the patient will then have a repeat CT scan of the chest/abdomen/pelvis after completion of at least 3 cycles of standard chemotherapy. After transplant, patients will undergo monthly CT scans of the chest/abdomen/pelvis for 2 months then every 2 months and as needed per the Investigators' discretion to assess for progressive disease or response. The post-transplant month 2 CT scan will be considered the confirmatory response scan.

Patients will be evaluable for toxicity from day 1 of baseline apheresis.

Patients will be evaluable for objective response by CT imaging at several time points:

1. Week 8 if not on chemotherapy.
2. One, 2, and 4 months after autologous hematopoietic and immune cell rescue.

The post-rescue CT scans will be compared to both the pre-conditioning and screening CT scans. Responses from the pre-conditioning scans (week 8 or 18) as compared to the post-rescue scans will be the primary assessment of response to our investigational therapy as the comparison to the study entry (screening) scan may be biased by any chemotherapy intervention.

Efficacy assessment will be done using Response Evaluation Criteria in Solid Tumors (RECIST) (1).

Disease Parameters

Accurate estimation of the overall tumor burden at baseline is necessary to assess objective response with treatment. Measurable disease is defined by the presence of at least one measurable lesion.

All measurements will be recorded in metric notation by use of ruler, calipers or computer-assisted measurement tools. The same method of assessment and the same technique should be used to characterize each identified lesion at baseline and during follow-up. All baseline evaluations should be performed no more than four weeks before registration.

Definition of Measurable Disease

Lesions that can be accurately measured in at least one dimension (longest dimension to be recorded) as ≥20 mm (2.0 cm) with conventional techniques or as ≥10 mm (1.0 cm) with a spiral CT scan.

For measurable disease existing as a solitary lesion, confirmation of malignant nature should be performed with cytology/histology if there is reasonable doubt in the investigator's opinion about the origin of the lesion.

Definition of Non-Measurable Disease

All lesions not considered measurable by the definition above, including small lesions (longest diameter ≤20 mm with conventional techniques or ≤10 mm with spiral CT) and truly non-measurable lesions. Truly non-measurable lesions include: bone lesions, leptomeningeal disease, malignant ascites, malignant pleural or pericardial effusion, inflammatory breast disease, lymphangitic spread of tumor, and abdominal masses that are not pathologically confirmed metastases and followed solely by imaging techniques.

Previously irradiated lesions are considered non-measurable.

Methods for Evaluation of Measurable Disease

CT and Mill: CT and Mill scans are currently the best available and most reproducible methods for measuring target lesions. Conventional CT and MM should be performed with contiguous cuts of 10 mm or less in slice thickness. Spiral CT should be performed using a 5 mm contiguous reconstruction algorithm.

Chest X-ray: lesions on chest X-ray are acceptable as measurable lesions when they are clearly defined and surrounded by aerated lung.

Clinical examination: clinically detected lesions will only be considered measurable if they are superficial and readily palpable on repeated clinical examination.

Response Criteria

Evaluation of Target Lesions

Target lesions will be defined as all measurable lesions up to a maximum of five lesions per organ and 10 lesions in total, representative of all involved organs. Target lesions should be selected based on the largest size and best suitability for accurate repeated measurements.

The sum of the longest diameters of all target lesions will be calculated at baseline and reported as the baseline sum longest diameter. This baseline sum longestdiameter will be used as the reference to characterize objective tumor response. For lesions measurable in 2 or 3 dimensions, the longest diameter at the time of assessment will be reported.

Using RECIST criteria, target lesions will be evaluated:

Complete response (CR): The disappearance of all target and non-target lesions, and no new lesions. If any tumor markers were elevated prior to therapy they must be normal for the patient to be declared a CR.

Partial response (PR): At least a 30% decrease in the sum of the longest diameters of target lesions, taking as reference the baseline sum longest diameter.

Progressive disease (PD): At least a 20% increase in the sum of the longest diameters of the target lesions, taking as reference the smallest sum longest diameter recorded since the baseline measurements, or the appearance of one or more new lesions.

Stable disease (SD): Neither sufficient shrinkage to qualify for partial response nor sufficient increase to qualify for progressive disease. To be assigned a status of stable disease, measurements must have met the stable disease criteria at least once after study entry at a minimum interval of six weeks.

Symptomatic deterioration: Patients with global deterioration of health status requiring discontinuation of treatment without objective evidence of disease progression at that time should be classified as having symptomatic deterioration.

Evaluation of Best Overall Response

The best overall response is the best response recorded from registration until disease progression/recurrence.

| Target Lesions | Nontarget Lesions | New Lesions | Overall Response |
|---|---|---|---|
| CR | CR | No | CR |
| CR | PR/SD | No | PR |
| PR | No PD | No | PR |
| SD | No PD | No | SD |
| PD | Any | Yes or No | PD |
| Any | PD | Yes or No | PD |
| Any | Any | Yes | PD |

CR = complete response;
PR = partial response;
SD = stable disease;
PD = progressive disease To be assigned a status of stable disease, measurements must have met the stable disease criteria at least once after study entry at a minimum interval of six weeks.

Duration of Response

Duration of overall response is the period measured from the time that measurement criteria are met for complete or partial response (whichever status is recorded first) until the first date that recurrent or progressive disease is objectively documented, taking as reference the smallest measurements recorded since treatment started.

Other Efficacy Parameters

First documentation of Response: The time between initiation of therapy and first documentation of PR or CR.

Duration of Stable Disease: Duration of stable disease is the measurement from registration until the criteria for disease progression is met, taking as reference the smallest measurements recorded since registration. To be assigned a status of stable disease, measurements must have met the stable disease criteria at least once after study entry at a minimum interval of six weeks.

Overall Survival (OS): Time from the date of enrollment to the date of death due to any cause or the last date the patient was known to be alive (censored observation) at the date of data cutoff for the final analysis Time to Progression (TTP): Time from the date of enrollment to the date of the first observation of documented disease progression or death to due cancer Other Response Parameters Tumor markers: Tumor markers alone cannot be used to assess response. However, if a tumor marker is initially above the upper limit of normal, it must normalize for a patient to be considered in complete CR when all tumor lesions have disappeared. The tumor markers that will be assessed in this study are CEA and CA 19-9.

Statistical Considerations

Endpoints

Primary Endpoint

To assess the feasibility of using an autologous tumor cell vaccine in combination with standard chemotherapy and investigational autologous hematopoietic and immune cell rescue in terms of acceptable clinical toxicity.

Secondary Endpoints

Ex vivo assessment of immune response

Response

TTP

Plan of Analysis

Background and Demographic Characteristics

Baseline demographic characteristics will be recorded on each patient including age, gender, race, ECOG performance status, location of primary cancer, location and number of metastases, presence or absence of primary tumor, dates of initial diagnosis and recurrence if applicable, and presence of other co-morbidities.

Evaluation of Safety

Any patient who receives the baseline apheresis will be included in the qualitative safety analysis irrespective of whether they receive vaccination.

Evaluation of Efficacy

The study will not be powered for efficacy but we will determine response according to RECIST criteria and PFS to qualitatively assess for therapeutic promise.

Methods for Handling Missing Data and Non-Adherence to Protocol

If missing data is discovered, genuine efforts will be taken to recover the data when possible. If protocol violations occur, they will be reported to the IRB, SRC, FDA, and Pfizer.

Interim Analyses

Weekly meetings of the investigative team will be held to review the patients on trial and to discuss all toxicities encountered. Safety data will be reviewed continuously. If the trial is not deemed feasible from a safety or financial standpoint or is not thought efficacious, it will be halted prior to complete accrual of the 10 patients if not already done.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

1. Finn, O. J. 2003. Cancer vaccines: between the idea and the reality. Nat Rev Immunol. 3:630-641.
2. Rosenberg, S. A., J. C. Yang, 2004. Cancer immunotherapy: moving beyond current vaccines. Nature Medicine 10: 909-915.
3. Rosenberg, S. A., N. P. Restifo, J. C. Yang, R. A. Morgan, and M. E. Dudley. 2008. Adoptive cell transfer: a clinical path to effective cancer immunotherapy. Nat Rev Cancer. 8: 299-308.
4. Huang, A. Y., P. H. Gulden, A. S. Woods, M. C. Thomas, C. D. Tong, W. Wang, V. H. Engelhard, G. Pasternack, R. Cotter, D. Hunt, D. M Rardoll, and E. M. Jaffee. 192. The immunodominant major histocompatibility complex class I-restricted antigen of a murine colon tumor derives from an endogenous retroviral gene product. Proc Natl Acad Sci USA. 93: 330-335.
5. Slansky, J. E., F. M. Rattis, L. F. Boyd, T. Fahmy, E. M. Jaffee, J. P. Schneck, D. H. Margulies, and D. M. Pardoll. 2000. Enhanced antigen-specific antitumor immunity with altered peptide ligands that stabilize the MHC-peptide-TCR complex. Immunity. 13:529-38.
6. McMahan, R. H., J. A., McWilliams, K. R. Jordan, S. W. Dow, D. B. Wilson, and J. E. Slansky. 2006. Relating TCR-peptide-MHC affinity to immunogenicity for the design of tumor vaccines. J Clin Invest. 116:2543-51.
7. McWilliams, J. A., Sullivan, R. T., Jordan, K. R., McMahan, R. H., Kemmler, C. B., McDuffie, M, and J. E. Slansky. 2008. Age-dependent tolerance to an endogenous tumor-associated antigen. Vaccine. 26:1863-73.
8. Corbett, T. H., Griswold, D. P., and B. J. Roberts. 135. Tumor induction relationships in development of transplantable cancers of the colon in mice for chemotherapy assays, with a note on carcinogen structure. Cancer Res. 35: 2434-2439.
9. Dutt, S., Ermann, J., Tseng, D, Liu, Y. P., George, T. I., Fathman, C. G., and S. Strober. 2005. L-selectin and beta7 integrin on donor CD4 T cells are required for the early migration to host mesenteric lymph nodes and acute colitis of graft-versus-host disease. Blood. 10:4009-4015.
10. Spangrude, G. J., Heimfeld, S., and I. L. Weissman, 1998. Purification and characterization of mouse hematopoietic stem cells. Science. 241:58-62.
11. Pillai A. B., T. I. George, S. Dutt, P. Teo, and S. Strober. 2007. Host NKT cells can prevent graft-versus-host disease and permit graft antitumor activity after bone marrow transplantation. J Immunol. 15; 178:6242-51.
12. Hemmi H., O. Takeuchi, T. Kawai, T. Kaisho, S. Sato, H. Sanjo, M. Matsumoto, K. Hoshino, H. Wagner, K. Takeda, S. Akira. 2000. A Toll-like receptor recognizes bacterial DNA. Nature 408:740-745.
13. Okano, F., M. Merad, K. Furumoto, and E. G Engleman. 2005. In vivo manipulation of dendritic cells overcomes tolerance to unmodified tumor-associated self antigens and induces potent antitumor immunity. J Immunol. 174: 2645-2652.
14. Yu P, Lee Y, Liu W, Krausz T, Chong A, Schreiber, H, and Fu YX. 2005. Intra-tumor depletion of CD4+ cells unmasks tumor immunogenicity leading to the rejection of late-stage tumors. J. Exp. Med. 201: 779-791.
15. Borrello, I., E. M. Sotomayor, F. Rattis, S. K. Cooke, L. Gu, and H. I. Levitsky. 2000. Sustaining the graft-versus-tumor effect through posttransplant immunization with granulocyte-macrophage colony-stimulating factor (GM-CSF)-producing tumor vaccines. Blood. 95: 3011-3019.
16. Mirmonsef, P., Tan, G, Zhou, G, Morino, T, Noonan, K, Borrello, I, and H. Levitsky, 2008. Escape from suppression: tumor-specific effector cells outcompete regulatory T cells following stem-cell transplantation. Blood. 111: 2112-2121.
17. Meunier, M. C., Delisle, J C, Bergeron, J, Rineau, V, Baron, C & Perreault, C. 2005. T cells targeted against a single minor histocompatibility antigen can cure solid tumors. Nature Medicine. 11:1222-1229.
18. Luznik, L., J. E. Slansky, S. Jalla, I. Borrello, H. I. Levitsky, D. M. Pardoll, and F. J. Fuchs. 2003. Successful therapy of metastatic cancer using tumor vaccines in mixed allogeneic bone marrow chimeras. Blood. 5:1645-1652.
19. Childs R., A. Chernoff, N. Contentin, E. Bahceci, D. Schrump, S. Lietman, E. J. Read, J. Tisdale, C. Dunbar, W M. Linehan, N. S. Young, and A. K. Barrett. 2000. Regression of metastatic renal-cell carcinoma after non-myeloablative allogeneic peripheral-blood stem-cell transplantation. N Engl J Med. 343:750-758.
20. Massenkeil, G., M., S. Nagy, S. Neuburger, I. Tamm, C. P. Lutz, O. le Coutre, O. Rosen, K.-D. Wernecke, B.

Dörken, and R. Arnold. 2005. Survival after reduced-intensity conditioning is not inferior to standard high-dose conditioning before allogeneic haematopoietic cell transplantation in acute leukaemias. Bone Marrow Transplantation 36:683-689.
21. Carnevale-Schianca, F., A. Cignetti, A. Capaldi, K. Vitaggio, A. Vallario, A. Ricchiardi, E. Sperti, R. Ferraris, M. Gatti, G. Grignan, D. Rota-Scalabrini, M. Geuna, Fizzotti, D. Sangiolo, A. Sottile, G. De Rosa, A. Bucci, G. Lambertenghi-Deliliers, E. Benedetti, R. Nash, and M. Aglietta. 2006. Allogeneic nonmyeloablative hematopoietic cell transplantation in metastatic colon cancer: tumor-specific T cells directed to a tumor-associated antigen are generated in vivo during GVHD. Blood 107:3795-3803.
22. Paulos, C. M., C. Wrzesinski, A. Kaiser, C. S. Hinrichs, M. Chieppa, L. Cassard, D. C. Palmer, A. Boni, P. Muranski, Z. Yu, L. Gattinoni, P. A. Antony, S. A. Rosenberg, and N. P. Restifo. 2007. Microbial translocation augments the function of adoptively transferred self/tumor-specific CD8+ T cells via TLR4 signaling. J Clin Invest 117:213-2204.
23. Wrzesinski, C., C. M. Paulos, L. Gattinoni, D. C. Palmer, A. Kaiser, Z. Yu, S. A. Rosenberg and N. P. Restifo. 2007. Hematopoietic stem cells promote the expansion and function of adoptively transferred antitumor CD8 T cells. J Clin Invest 117: 41-501.
24. Bevan, M. J. 2004. Helping the CD8(+) T-cell response. Nat Rev Immunol 4:595-602.
25. Jemal A, Siegel R, Ward E, et al. Cancer statistics, 2008. CA Cancer J Clin 2008; 58:71-2.
26. Goldberg R M, Sargent D J, Morton R F, et al. A randomized controlled trial of fluorouracil plus leucovorin, irinotecan, and oxaliplatin combinations in patients with previously untreated metastatic colorectal cancer. J Clin Oncol 2004; 22:23-30.
27. Cassidy J C S, Diaz-Rubio E, Scheithauer W, Figer A, Wong R, Koski S, Lichinitser M, Yang T, Saltz L B. XELOX vs. FOLFOX4: Efficacy results from XELOX-1/N01626, a randomized phase III trial in first-line metastatic colorectal cancer (MCRC). In: 2007 ASCO Gastrointestinal Cancer Symposium. p. Abstract 270.
28. Diaz-Rubio E, Tabernero J, Gomez-Espana A, et al. Phase III study of capecitabine plus oxaliplatin compared with continuous-infusion fluorouracil plus oxaliplatin as first-line therapy in metastatic colorectal cancer: final report of the Spanish Cooperative Group for the Treatment of Digestive Tumors Trial. J Clin Oncol 2007; 25:4224-30.
29. Ducreux M B J, Hebbar M, Ychou M, Lledo G, Conroy T, Adenis A, Faroux R, Rebischung C, Douillard J. Efficacy and safety findings from a randomized phase III study of capecitabine (X)+oxaliplatin (O) (XELOX) vs. infusional 5-FU/LV+O (FOLFOX-6) for metastatic colorectal cancer (MCRC). In: Journal of Clinical Oncology, 2007 ASCO Annual Meeting Proceedings Part I Vol 25, No 18S (June 20 Supplement), 2007: 4029.
30. Hochster H S H L, Ramanathan R K, Hainsworth J D, Hedrick E E, Childs B H. Safety and efficacy of oxaliplatin/fluoropyrimidine regimens with or without bevacizumab as first-line treatment of metastatic colorectal cancer (mCRC): Final analysis of the TREE-Study. In: Journal of Clinical Oncology, 2006 ASCO Annual Meeting Proceedings Part I Vol 24, No 18S (June 20 Supplement), 2006: 3510.
31. Hochster H S W L, Hart L, Ramanathan R K, Hainsworth J, Jirau-Lucca G, Shpilsky A, Griffing S, Mass R, Emanuel D. Safety and efficacy of bevacizumab (Bev) when added to oxaliplatin/fluoropyrimidine (O/F) regimens as first-line treatment of metastatic colorectal cancer (mCRC): TREE 1 & 2 Studies. In: Journal of Clinical Oncology, 2005 ASCO Annual Meeting Proceedings Vol 23, No 16S, Part I of II (June 1 Supplement), 2005: 3515.
32. Porschen R, Arkenau H T, Kubicka S, et al. Phase III study of capecitabine plus oxaliplatin compared with fluorouracil and leucovorin plus oxaliplatin in metastatic colorectal cancer: a final report of the AIO Colorectal Study Group. J Clin Oncol 2007; 25:4217-23.
33. Hurwitz H, Fehrenbacher L, Novotny W, et al. Bevacizumab plus irinotecan, fluorouracil, and leucovorin for metastatic colorectal cancer. N Engl J Med 2004; 350: 2335-42.
34. Saltz L B, Clarke S, Diaz-Rubio E, et al. Bevacizumab in combination with oxaliplatin-based chemotherapy as first-line therapy in metastatic colorectal cancer: a randomized phase III study. J Clin Oncol 2008; 26:2013-9.
35. Cunningham D, Humblet Y, Siena S, et al. Cetuximab monotherapy and cetuximab plus irinotecan in irinotecan-refractory metastatic colorectal cancer. N Engl J Med 2004; 351:337-45.
36. Jonker D J, O'Callaghan C J, Karapetis C S, et al. Cetuximab for the treatment of colorectal cancer. N Engl J Med 2007; 357:2040-8.
37. Van Cutsem E N M, Lang I, Cascinu S, Shchepotin I, Maurel J, Rougier P, Cunningham D, Nippgen J, Köhne C. Randomized phase III study of irinotecan and 5-FU/FA with or without cetuximab in the first-line treatment of patients with metastatic colorectal cancer (mCRC): The CRYSTAL trial. In: Journal of Clinical Oncology, 2007 ASCO Annual Meeting Proceedings Part I Vol 25, No 18S (June 20 Supplement), 2007: 4000.
38. Jennis A P J, Mitchell E, Badarinath S, Graham C, Chen T, Gustafson T, Langer C. Erbitux (Cetuximab) Plus FOLFOX for Colorectal Cancer (EXPLORE): Preliminary efficacy analysis of a randomized phase III trial. In: Journal of Clinical Oncology, 2005 ASCO Annual Meeting Proceedings Vol 23, No 16S, Part I of II (June 1 Supplement), 2005: 3574.
39. Maughan T obotCTMGaI. Cetuximab (C), oxaliplatin (Ox) and fluoropyrimidine (Fp): Toxicity during the first 12 weeks of treatment for the first 804 patients entered into the MRC COIN (CR10) trial. Journal of Clinical Oncology, 2007 ASCO Annual Meeting Proceedings Part I Vol 25, No 18S (June 20 Supplement), 2007: 4070.
40. Ciardiello F, Tortora G. EGFR antagonists in cancer treatment. N Engl J Med 2008; 358:1160-74.
41. Mitchell E P P J, Badarinath S, Jennis A, Labrosciano A, Awad M, Lu H, Langer C, Khambata-Ford S. Analysis of K-RAS mutation status and EGFR gene copy number in the EXPLORE study: FOLFOX4 vs. FOLFOX4/cetuximab in previously treated metastatic colorectal cancer (mCRC). In: ASCO Gastrointestinal Cancers Symposium; 2008; 2008. p. Abstract 308.
42. Van Cutsem E L I, D'haens G, Moiseyenko V, Zaluski J, Folprecht G, Tejpar S, Kisker O, Stroh C, Rougier P. KRAS status and efficacy in the first-line treatment of patients with metastatic colorectal cancer (mCRC) treated with FOLFIRI with or without cetuximab: The CRYSTAL experience. In: J Clin Oncol 26: 2008 (May 20 suppl; abstr 2).
43. Tabernero J, Van Cutsem E, Diaz-Rubio E, et al. Phase II trial of cetuximab in combination with fluorouracil, leucovorin, and oxaliplatin in the first-line treatment of metastatic colorectal cancer. J Clin Oncol 2007; 25:5225-32.

44. Corbett T H, Griswold D P, Jr., Roberts B J, Peckham J C, Schabel F M, Jr. Tumor induction relationships in development of transplantable cancers of the colon in mice for chemotherapy assays, with a note on carcinogen structure. Cancer Res 135; 35:2434-9.
45. Jain A, Slansky J E, Matey L C, Allen H E, Pardoll D M, Schulick R D. Synergistic effect of a granulocyte-macrophage colony-stimulating factor-transduced tumor vaccine and systemic interleukin-2 in the treatment of murine colorectal cancer hepatic metastases. Ann Surg Oncol 2003; 10:810-20.
46. Park J M, Terabe M, van den Broeke L T, Donaldson D D, Berzofsky J A. Unmasking immunosurveillance against a syngeneic colon cancer by elimination of CD4+ NKT regulatory cells and IL-13. Int J Cancer 2005; 114:80-7.
47. Slansky J E, Rattis F M, Boyd L F, et al. Enhanced antigen-specific antitumor immunity with altered peptide ligands that stabilize the MHC-peptide-TCR complex. Immunity 2000; 13:529-38.
48. Okano F, Merad M, Furumoto K, Engleman E G. In vivo manipulation of dendritic cells overcomes tolerance to unmodified tumor-associated self antigens and induces potent antitumor immunity. J Immunol 2005; 174:2645-52.
49. Berd D, Maguire H C, Jr., McCue P, Mastrangelo M J. Treatment of metastatic melanoma with an autologous tumor-cell vaccine: clinical and immunologic results in 64 patients. J Clin Oncol 1990; 8:1858-67.
50. Berd D, Maguire H C, Jr., Schuchter L M, et al. Autologous hapten-modified melanoma vaccine as post-surgical adjuvant treatment after resection of nodal metastases. J Clin Oncol 193; 15:2359-70.
51. Berd D, Sato T, Cohn H, Maguire H C, Jr., Mastrangelo M J. Treatment of metastatic melanoma with autologous, hapten-modified melanoma vaccine: regression of pulmonary metastases. Int J Cancer 2001; 94:531-9.
52. Chang A E, Li Q, Jiang G, Sayre D M, Braun T M, Redman B G. Phase I I trial of autologous tumor vaccination, anti-CD3-activated vaccine-primed lymphocytes, and interleukin-2 in stage IV renal cell cancer. J Clin Oncol 2003; 21:884-90.
53. Hoover H C, Jr., Brandhorst J S, Peters L C, et al. Adjuvant active specific immunotherapy for human colorectal cancer: 6.5-year median follow-up of a phase III prospectively randomized trial. J Clin Oncol 1993; 11:390-9.
54. Jocham D, Richter A, Hoffmann L, et al. Adjuvant autologous renal tumour cell vaccine and risk of tumour progression in patients with renal-cell carcinoma after radical nephrectomy: phase III, randomised controlled trial. Lancet 2004; 363:594-9.
55. Uyl-de Groot C A, Vermorken J B, Hanna M G, Jr., et al. Immunotherapy with autologous tumor cell-BCG vaccine in patients with colon cancer: a prospective study of medical and economic benefits. Vaccine 2005; 23:2379-87.
56. Copier J, Ward S, Dalgleish A. Cell based cancer vaccines: regulatory and commercial development. Vaccine 2007; 25 Suppl 2:B35-46.
57. Sahasrabudhe D M, deKernion J B, Pontes J E, et al. Specific immunotherapy with suppressor function inhibition for metastatic renal cell carcinoma. J Biol Response Mod 1986; 5:581-94.
58. Wei Y, Sticca R P, Holmes L M, et al. Dendritoma vaccination combined with low dose interleukin-2 in metastatic melanoma patients induced immunological and clinical responses. Int J Oncol 2006; 28:585-93.
59. Krieg A M, Yi A K, Matson S, et al. CpG motifs in bacterial DNA trigger direct B-cell activation. Nature 1995; 374:546-9.
60. Wilson H L, Dar A, Napper S K, Marianela Lopez A, Babiuk L A, Mutwiri G K. Immune mechanisms and therapeutic potential of CpG oligodeoxynucleotides. Int Rev Immunol 2006; 25:183-213.
61. Higgins D, Marshall J D, Traquina P, Van Nest G, Livingston B D. Immunostimulatory DNA as a vaccine adjuvant. Expert Rev Vaccines 2007; 6:747-59.
62. Krieg A M. Development of TLR9 agonists for cancer therapy. J Clin Invest 2007; 117:1184-94.
63. Krieg A M. The CpG motif: implications for clinical immunology. BioDrugs 1998; 10:341-6.
64. Brody J A W, Czerwinski D, Advani R, Horning S J, Ganjoo K N, Levy R Clinical and immunologic responses to a novel in situ lymphoma vaccine maneuver: Preliminary results of a phase II trial of intra-tumoral CpG 7909. J Clin Oncol 26: 2008 (May 20 suppl; abstr 3003) 2008.
65. Cooper C L, Davis H L, Morris M L, et al. CPG 7909, an immunostimulatory TLR9 agonist oligodeoxynucleotide, as adjuvant to Engerix-B HBV vaccine in healthy adults: a double-blind phase I/II study. J Clin Immunol 2004; 24:693-701.
66. Lowder J N F J, Kelly J, Freedman A S, Coffman R, Kanzler H, Sims P, Hwang J, Haining N. Dose Finding in Human Trials of TLR9 Agonists: Induction of Interferon-{alpha} Inducible Genes in Blood Mononuclear Cells as a Measure of Biologic Activity of 58 ISS. Blood (ASH Annual Meeting Abstracts), November 2007; 110: 3844
67. Witzig T E W G, Weiner G, Ansell S M, Micallef I, Habermann T M, Zent C S, Inwards D J, Shanafelt T, Porrata L, Maurer M J, Allmer C, Ballas Z. A Phase I Trial of CpG-7909, Rituximab Immunotherapy, and Y90 Zevalin Radioimmunotherapy for Patients (Pts) with Previously Treated CD20+ Non-Hodgkin Lymphoma (NHL). Blood (ASH Annual Meeting Abstracts), November 2007; 110: 124
68. Corringham R, Gilmore M, Prentice H G, Boesen E. High-dose melphalan with autologous bone marrow transplant. Treatment of poor prognosis tumors. Cancer 1983; 52:1783-7.
69. Einhorn L H, Williams S D, Chamness A, Brames M J, Perkins S M, Abonour R. High-dose chemotherapy and stem-cell rescue for metastatic germ-cell tumors. N Engl J Med 2007; 357:340-8.
70. Fish J D, Grupp S A. Stem cell transplantation for neuroblastoma. Bone Marrow Transplant 2008; 41:159-65.
71. Lazarus H M, Herzig R H, Graham-Pole J, et al. Intensive melphalan chemotherapy and cryopreserved autologous bone marrow transplantation for the treatment of refractory cancer. J Clin Oncol 1983; 1:359-67.
72. McElwain T J, Hedley D W, Burton G, et al. Marrow autotransplantation accelerates haematological recovery in patients with malignant melanoma treated with high-dose melphalan. Br J Cancer 139; 40:72-80.
73. Leff R S, Thompson J M, Johnson D B, et al. Phase I I trial of high-dose melphalan and autologous bone marrow transplantation for metastatic colon carcinoma. J Clin Oncol 1986; 4:1586-91.
74. Franchi F, Seminara P, Codacci Pisanelli G, Guazzugli Bonaiuti VP, Giovagnorio F, Gualdi G. Elevated doses of carmustine and mitomycin C, with lonidamine enhancement and autologous bone marrow transplantation in the 74. treatment of advanced colorectal cancer: results from a pilot study. Eur J Cancer 1994; 30A:1420-3.
75. Spitzer T R, Lazarus H M, Creger R J, Berger N A. High-dose melphalan, misonidazole, and autologous bone marrow transplantation for the treatment of metastatic colorectal carcinoma. A phase I study. Am J Clin Oncol 1989; 12:145-51.
76. Napolitano L A, Grant R M, Deeks S G, et al. Increased production of IL-7 accompanies HIV-1-mediated T-cell depletion: implications for T-cell homeostasis. Nat Med 2001; 7:73-9.
77. Bolotin E, Smogorzewska M, Smith S, Widmer M, Weinberg K. Enhancement of thymopoiesis after bone marrow transplant by in vivo interleukin-7. Blood 192; 88:1887-94.
78. Bolotin E, Annett G, Parkman R, Weinberg K. Serum levels of IL-7 in bone marrow transplant recipients: relationship to clinical characteristics and lymphocyte count. Bone Marrow Transplant 1999; 23:783-8.
79. Tang J, Nuccie B L, Ritterman I, Liesveld J L, Abboud C N, Ryan D H. TGF-beta down-regulates stromal IL-7 secretion and inhibits proliferation of human B cell precursors. J Immunol 193; 159:117-25.
80. Stephan R P, Reilly C R, Witte P L. Impaired ability of bone marrow stromal cells to support B-lymphopoiesis with age. Blood 1998; 91:75-88.
81. Jameson S C. Maintaining the norm: T-cell homeostasis. Nat Rev Immunol 2002; 2:547-56.
82. Roat E, Prada N, Lugli E, et al. Homeostatic Cytokines and Expansion of Regulatory T Cells Accompany Thymic Impairment in Children with Down Syndrome. Rejuvenation Res 2008.
83. Garrity M M, Burgart L J, Mahoney M R, et al. Prognostic value of proliferation, apoptosis, defective DNA mismatch repair, and p53 overexpression in patients with resected Dukes' B2 or C colon cancer: a North Central Cancer Treatment Group Study. J Clin Oncol 2004; 22:1572-82.
84. Livak F, Schatz D G. T-cell receptor alpha locus V(D)J recombination by-products are abundant in thymocytes and mature T cells. Mol Cell Biol 192; 16:609-18.
85. Douek D C, McFarland R D, Keiser P H, et al. Changes in thymic function with age and during the treatment of HIV infection. Nature 1998; 32:690-5.
86. Douek D C, Vescio R A, Betts M R, et al. Assessment of thymic output in adults after haematopoietic stem-cell transplantation and prediction of T-cell reconstitution. Lancet 2000; 355:1875-81.
87. Atkins M B, Mier J W, Parkinson D R, Gould J A, Berkman E M, Kaplan M M. Hypothyroidism after treatment with interleukin-2 and lymphokine-activated killer cells. N Engl J Med 1988; 318:1557-63.
88. Gogas H, Ioannovich J, Dafni U, et al. Prognostic significance of autoimmunity during treatment of melanoma with interferon. N Engl J Med 2006; 354:709-18.
89. Ribas A, Camacho L H, Lopez-Berestein G, et al. Antitumor activity in melanoma and anti-self responses in a phase I trial with the anti-cytotoxic T lymphocyte-associated antigen 4 monoclonal antibody CP-675,206. J Clin Oncol 2005; 23:828-77.
90. Weijl N I, Van der Harst D, Brand A, et al. Hypothyroidism during immunotherapy with interleukin-2 is associated with antithyroid antibodies and response to treatment. J Clin Oncol 1993; 11:1376-83.
91. Koon H, Atkins M. Autoimmunity and immunotherapy for cancer. N Engl J Med 2006; 354:758-60.
92. Therasse P, Arbuck S G, Eisenhauer E A, et al. New guidelines to evaluate the response to treatment in solid tumors. European Organization for Research and Treatment of Cancer, National Cancer Institute of the United States, National Cancer Institute of Canada. J Natl Cancer Inst 2000; 1:205-16.
93. Keating M J, O'Brien S, Plunkett W, et al. Fludarabine phosphate: a new active agent in hematologic malignancies. Semin Hematol 1994; 31:28-39.
94. Gregoire V, Hunter N, Brock W A, Milas L, Plunkett W, Hittelman W N. Fludarabine improves the therapeutic ratio of radiotherapy in mouse tumors after single-dose irradiation. Int J Radiat Oncol Biol Phys 1994; 30:363-71.
95. Giralt S, Estey E, Albitar M, et al. Engraftment of allogeneic hematopoietic progenitor cells with purine analog-containing chemotherapy: harnessing graft-versus-leukemia without myeloablative therapy. Blood 193; 89:4531-6.
96. Khouri I F, Keating M, Korbling M, et al. Transplant-lite: induction of graft-versus-malignancy using fludarabine-based nonablative chemotherapy and allogeneic blood progenitor-cell transplantation as treatment for lymphoid malignancies. J Clin Oncol 1998; 16:2817-24.
97. Slavin S, Nagler A, Naparstek E, et al. Nonmyeloablative stem cell transplantation and cell therapy as an alternative to conventional bone marrow transplantation with lethal cytoreduction for the treatment of malignant and nonmalignant hematologic diseases. Blood 1998; 91:756-63.

What is claimed is:

1. A method for treating a cancer in a recipient, the method comprising: providing a therapeutic cell composition for reducing a number of tumor cells in a recipient and formulated for administration to the recipient in need thereof, the composition comprising a plurality of immune cells and a plurality of hematopoietic cells, the plurality of immune cells and the plurality of hematopoietic cells being purified form a donor vaccinated with an effective dose of purified tumor cells, the plurality of immune cells further comprising CD4+ and CD8+ T cells, wherein the tumor cells in the recipient and the purified tumor cells used for vaccination of the donor are the same type of cancer and wherein the plurality of immune cells are a plurality of autologous immune cells and the plurality of hematopoietic cells are a plurality of autologous hematopoietic cells.

2. The method of claim 1, wherein the donor is vaccinated with an effective dose of purified tumor cells from the recipient.

3. The method of claim 2, wherein the donor is vaccinated with an effective dose of purified tumor cells in a vaccine formulation comprising an adjuvant.

4. The method of claim 1, wherein the hematopoietic cells further comprise CD34+ cells.

5. The method of claim 1, wherein the immune cells and hematopoietic cells are formulated for intravenous administration.

6. The method of claim 1, wherein the tumor cells are purified from a suspension of primary tumor cells or a suspension of metastatic tumor cells.

7. The method of claim 6, wherein the tumor cells are purified from stromal cells.

8. The method of claim 6, wherein the tumor cells are purified from immunosuppressive cells and immunosuppressive factors.

9. The method of claim 1, wherein the tumor cells are purified from a solid tumor.

10. The method of claim 1, wherein the tumor cells are purified from a non-solid tumor.

11. The method of claim 1, wherein the tumor cells are purified from blood.

12. The method of claim 1, wherein the tumor cells are purified to greater than 50%.

13. The method of claim 1, wherein the tumor cells are purified to greater than 90%.

14. The method of claim 1, wherein the tumor cells are irradiated.

15. The method of claim 3, wherein the adjuvant is an immunostimulant.

16. The method of claim 3, wherein the adjuvant is CpG or GM-CSF.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Syntehtic CpG oligonucleotide

<400> SEQUENCE: 1
tccatgacgt tcctgacgtt                                            20